(12) United States Patent
Borchardt et al.

(10) Patent No.: US 7,053,107 B2
(45) Date of Patent: May 30, 2006

(54) INDAZOLE COMPOUNDS AND PHARMACEUTICAL COMPOSITIONS FOR INHIBITING PROTEIN KINASES, AND METHODS FOR THEIR USE

(75) Inventors: Allen J. Borchardt, San Diego, CA (US); Robert Steven Kania, San Diego, CA (US); Cynthia L. Palmer, La Mesa, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 274 days.

(21) Appl. No.: 10/737,655

(22) Filed: Dec. 15, 2003

(65) Prior Publication Data

US 2004/0192735 A1  Sep. 30, 2004

Related U.S. Application Data

(60) Provisional application No. 60/434,902, filed on Dec. 19, 2002.

(51) Int. Cl.
*A61K 31/4439* (2006.01)
*A61K 31/416* (2006.01)
*C07D 213/06* (2006.01)
*C07D 237/26* (2006.01)

(52) U.S. Cl. .................. 514/333; 514/338; 514/406; 546/256; 546/275.7; 548/362.5

(58) Field of Classification Search ............... None
See application file for complete search history.

(56) References Cited

U.S. PATENT DOCUMENTS

| | | | |
|---|---|---|---|
| 5,476,511 A | 12/1995 | Gwon et al. | |
| 5,587,458 A | 12/1996 | King et al. | |
| 5,747,498 A | 5/1998 | Schnur et al. | |
| 5,773,019 A | 6/1998 | Ashton et al. | |
| 5,792,783 A | 8/1998 | Tang et al. | |
| 5,824,072 A | 10/1998 | Wong | |
| 5,834,504 A | 11/1998 | Tang et al. | |
| 5,861,510 A | 1/1999 | Piscopio et al. | |
| 5,863,949 A | 1/1999 | Robinson et al. | |
| 5,877,305 A | 3/1999 | Huston et al. | |
| 5,883,113 A | 3/1999 | Tang et al. | |
| 5,886,020 A | 3/1999 | Tang et al. | |
| 6,071,935 A | 6/2000 | Lyssikatos | |
| 6,080,769 A | 6/2000 | Lyssikatos et al. | |
| 6,150,377 A | 11/2000 | Lyssikatos et al. | |
| 6,194,438 B1 | 2/2001 | Yang et al. | |
| 6,258,824 B1 | 7/2001 | Yang | |
| 6,284,764 B1 | 9/2001 | Kath et al. | |
| 6,465,449 B1 | 10/2002 | Kath et al. | |
| 6,479,513 B1 | 11/2002 | Yang | |
| 6,495,564 B1 | 12/2002 | Lyssikatos et al. | |
| 6,511,993 B1 | 1/2003 | Dack et al. | |
| 6,531,491 B1 | 3/2003 | Kania et al. | |
| 6,534,524 B1 | 3/2003 | Kania et al. | |
| 6,586,447 B1 | 7/2003 | Lyssikatos et al. | |
| 6,682,736 B1 | 1/2004 | Hanson et al. | |
| 6,884,890 B1 * | 4/2005 | Kania et al. | 546/275.7 |
| 6,891,044 B1 * | 5/2005 | Kania et al. | 546/275.7 |
| 2003/0166675 A1 | 9/2003 | Yang | |

FOREIGN PATENT DOCUMENTS

| | | |
|---|---|---|
| EP | 606046 | 7/1994 |
| EP | 780386 | 6/1997 |
| EP | 0818442 | 1/1998 |
| EP | 0931788 | 7/1999 |
| EP | 1004578 | 5/2000 |
| EP | 1081137 | 3/2001 |
| EP | 1106612 | 6/2001 |
| WO | WO 90/05719 | 5/1990 |
| WO | WO 95/19970 | 7/1995 |
| WO | WO 95/21613 | 8/1995 |
| WO | WO 96/27583 | 3/1996 |
| WO | WO 96/14843 | 5/1996 |
| WO | WO 96/33172 | 10/1996 |
| WO | WO 97/13760 | 4/1997 |
| WO | WO 97/22596 | 6/1997 |
| WO | WO 97/32856 | 9/1997 |
| WO | WO 97/34876 | 9/1997 |
| WO | WO 98/02434 | 1/1998 |
| WO | WO 98/02437 | 1/1998 |
| WO | WO 98/02438 | 1/1998 |
| WO | WO 98/03516 | 1/1998 |
| WO | WO 98/07697 | 2/1998 |
| WO | WO 98/14451 | 4/1998 |

(Continued)

OTHER PUBLICATIONS

Alon, et al., "Vascular Endothelial Growth Factor Acts as a Survival Factor For Newly Formed Retinal Vessels and Had Implications for Retinopathy of Prematurity," *Nature Medicine*, 1995, 1024-1028, vol. 1, No. 10.

(Continued)

*Primary Examiner*—Cecilia Tsang
*Assistant Examiner*—Lexington Hoffman
(74) *Attorney, Agent, or Firm*—Edward D. Robinson; Bryan C. Zielinski

(57) ABSTRACT

Indazole compounds that modulate and/or inhibit the ophthalmic diseases and the activity of certain protein kinases are described. These compounds and pharmaceutical compositions containing them are capable of mediating tyrosine kinase signal transduction and thereby modulate and/or inhibit unwanted cell proliferation. The invention is also directed to the therapeutic or prophylactic use of pharmaceutical compositions containing such compounds, and to methods of treating ophthalmic diseases and cancer and other disease states associated with unwanted angiogenesis and/or cellular proliferation, such as diabetic retinopathy, neovascular glaucoma, rheumatoid arthritis, and psoriasis, by administering effective amounts of such compounds.

4 Claims, No Drawings

FOREIGN PATENT DOCUMENTS

| | | |
|---|---|---|
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 98/50356 | 11/1998 |
| WO | WO 98/54093 | 12/1998 |
| WO | WO 99/07675 | 2/1999 |
| WO | WO 99/10349 | 3/1999 |
| WO | WO 99/16755 | 4/1999 |
| WO | WO 99/24440 | 5/1999 |
| WO | WO 99/29667 | 6/1999 |
| WO | WO 99/35132 | 7/1999 |
| WO | WO 99/35146 | 7/1999 |
| WO | WO 99/52889 | 10/1999 |
| WO | WO 99/52910 | 10/1999 |
| WO | WO 99/61422 | 12/1999 |
| WO | WO 99/62890 | 12/1999 |
| WO | WO 00/37107 | 6/2000 |
| WO | WO 00/38665 | 7/2000 |
| WO | WO 00/38715 | 7/2000 |
| WO | WO 00/38716 | 7/2000 |
| WO | WO 00/38717 | 7/2000 |
| WO | WO 00/38718 | 7/2000 |
| WO | WO 00/38719 | 7/2000 |
| WO | WO 00/38730 | 7/2000 |
| WO | WO 00/38786 | 7/2000 |
| WO | WO 01 002369 | 1/2001 |
| WO | WO 01/40217 | 6/2001 |
| WO | WO 01 53268 | 7/2001 |
| WO | WO 03/015608 | 2/2003 |

OTHER PUBLICATIONS

Folkman, et al., "Angiogenesis in Cancer, Vascular, Rheumatoid and Other Disease," *Nature Medicine.*, 1995, 27-31, vol. 1, No. 1.

Jeffrey, Philip D., et al., "Mechanism of CDK Activation Revealed By the Structure of a CyclinA-CDK2 Complex," *Nature*, Jul. 27, 1995, 313-320, vol. 376.

Lee, et al., "New Synthetic Cluster Ligands for Galactose/N-Acetylgalactosamine-Specific Lectin of Mammalian Liver," *Biochemistry*, 1984, 4255-4261, vol. 23.

Lutty, et al., "A New Technique for Visualization of the Human Retinal Vasculature," *Arch. Ophthalmol.*, 1992, 267-276, vol. 110.

Merenmies, et al., "Receptor Tyrosine Kinase Signaling in Vascular Development," *Cell Growth & Differentiation*, 1997, 3-10, vol. 8.

Mohammadi, et al., "Identification of Six Novel Autophosphorylation Sites on Fibroblast Growth Factor Receptor 1 and Elucidation of Their Importance in Receptor Activation and Signal Transduction," *Molecular and Cellular Biology*, 1996, 977-989, vol. 16, No. 3.

Parsat, et al., "Characterization and Kinetic Mechanism of Catalytic Domain of Human Vascular Endothelial Growth Factor Receptor-2 Tyrosine Kinase (VEGFR2 TK), a Key Enzyme in Angiogenesis," *Biochemistry*, 1998, 16788-16801, vol. 37.

Penn, John S., et al., "The Range of $PaO_2$ Variation Determines the Severity of Oxygen-Induced Retinopathy in Newborn Rats," *Investigative Opthalmology & Visual Science*, 1995, 2063-2070, vol. 36, No. 10.

Still, et al., "Rapid Chormatographic Technique for Preparative Separations with Moderate Resolution," *J. Org. Chem.*, 1978, 2923-2925, vol. 43, No. 14.

Stone, J., et al., "Development of Retinal Vasculature is Mediated by Hypoxia-Induced Vascular Endothelial Growth Factor (VEGF) Expression by Neuroglia," *The Journal of Neuroscience*, 1995, 4738-4747, vol. 15, No. 7.

* cited by examiner

INDAZOLE COMPOUNDS AND PHARMACEUTICAL COMPOSITIONS FOR INHIBITING PROTEIN KINASES, AND METHODS FOR THEIR USE

CROSS-REFERENCE TO RELATED APPLICATIONS

This application claims the benefit of U.S. Provisional Patent Application No. 60/434,902, filed Dec. 19, 2002, herein incorporated by reference in its entirety for all purposes.

FIELD OF THE INVENTION

This invention is directed to indazole compounds that mediate and/or inhibit hyperproliferative disorders, such as cancer and ophthalmic diseases, and the activity of certain protein kinases, and to pharmaceutical compositions containing such compounds. The invention is also directed to the therapeutic or prophylactic use of such compounds and compositions, and to methods of treating hyperproliferative disorders, such as ophthalmic diseases and cancer as well as other disease states associated with unwanted angiogenesis and/or cellular proliferation, by administering effective amounts of such compounds.

BACKGROUND OF THE INVENTION

Hyperproliferative disorders and several diseases and conditions of the posterior segment of the eye threaten vision. Age related macular degeneration (ARMD or AMD), choroidal neovascularization (CNV), retinopathies (e.g., diabetic retinopathy, vitreoretinopathy, retinopathy of prematurity), retinitis (e.g., cytomegalovirus (CMV) retinitis), uveitis, macular edema, and glaucoma are several examples.

Age related macular degeneration (ARMD or AMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina. In the particular case of CNV in ARMD, two main methods of treatment are currently being developed, (a) photocoagulation and (b) the use of angiogenesis inhibitors.

However, photocoagulation can be harmful to the retina and is impractical when the CNV is in proximity of the fovea. Furthermore, photocoagulation often results in recurrent CNV over time.

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., *Cell Growth & Differentiation*, 8, 3–10 (1997). On the other hand, unwanted angiogenesis is a hallmark of several diseases, such as retinopathies, psoriasis, rheumatoid arthritis, age-related macular degeneration (AMD), and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

Oral administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Various implants have also been developed for delivery of anti-angiogenic compounds locally to the eye. Examples of such implants are disclosed in U.S. Pat. No. 5,824,072 to Wong, U.S. Pat. No. 5,476,511 to Gwon et al., and U.S. Pat. No. 5,773,019 to Ashton et al., each of which is herein incorporated by reference in their entireties for all purposes.

The compounds of the present invention are improved anti-angiogenic agents that can be used alone or in combination.

SUMMARY OF INVENTION

The present invention provides compounds having the following structures:

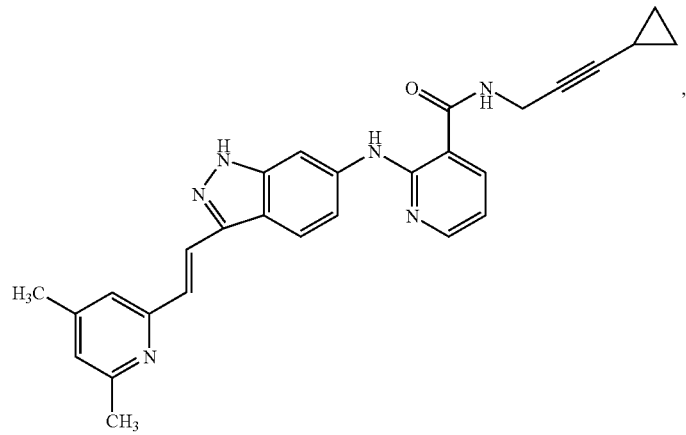

-continued
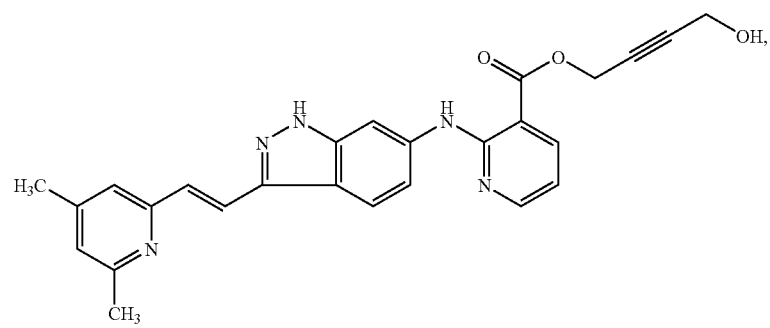
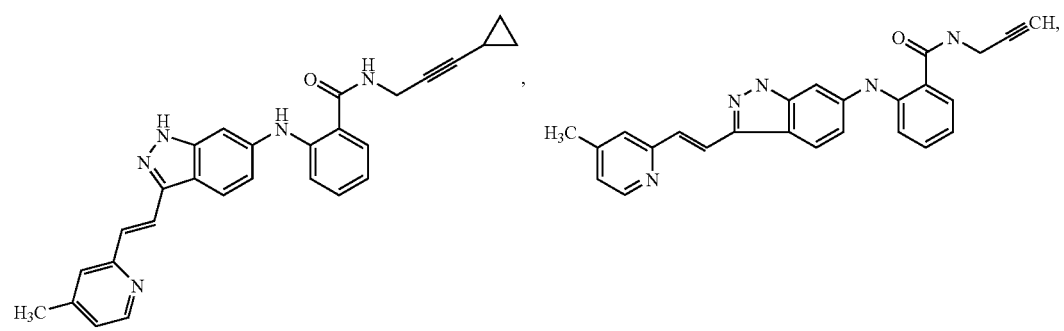
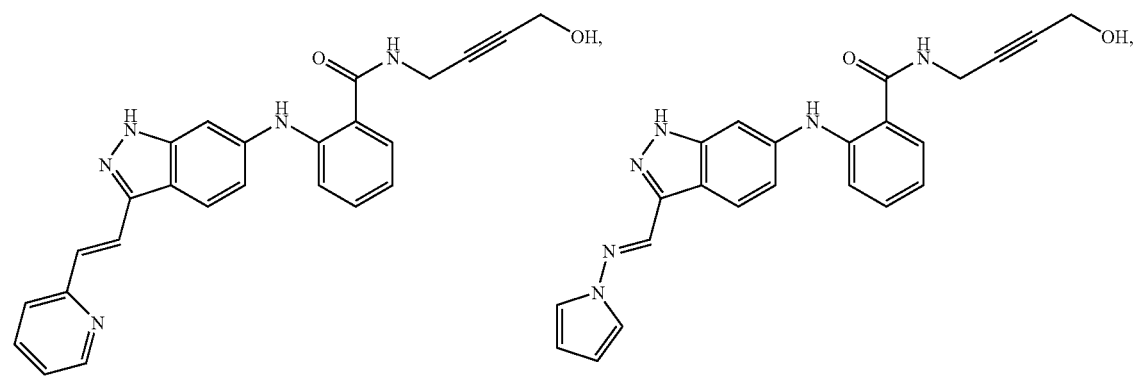
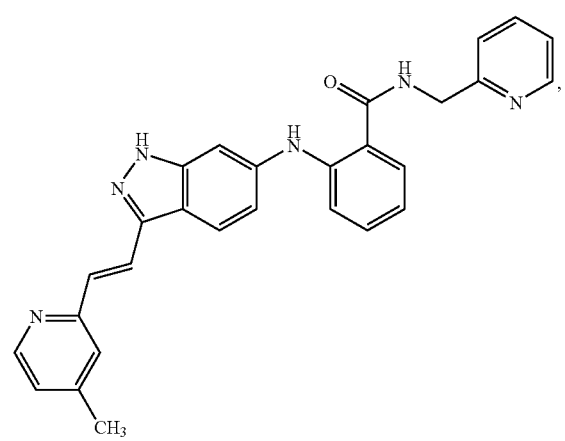

-continued
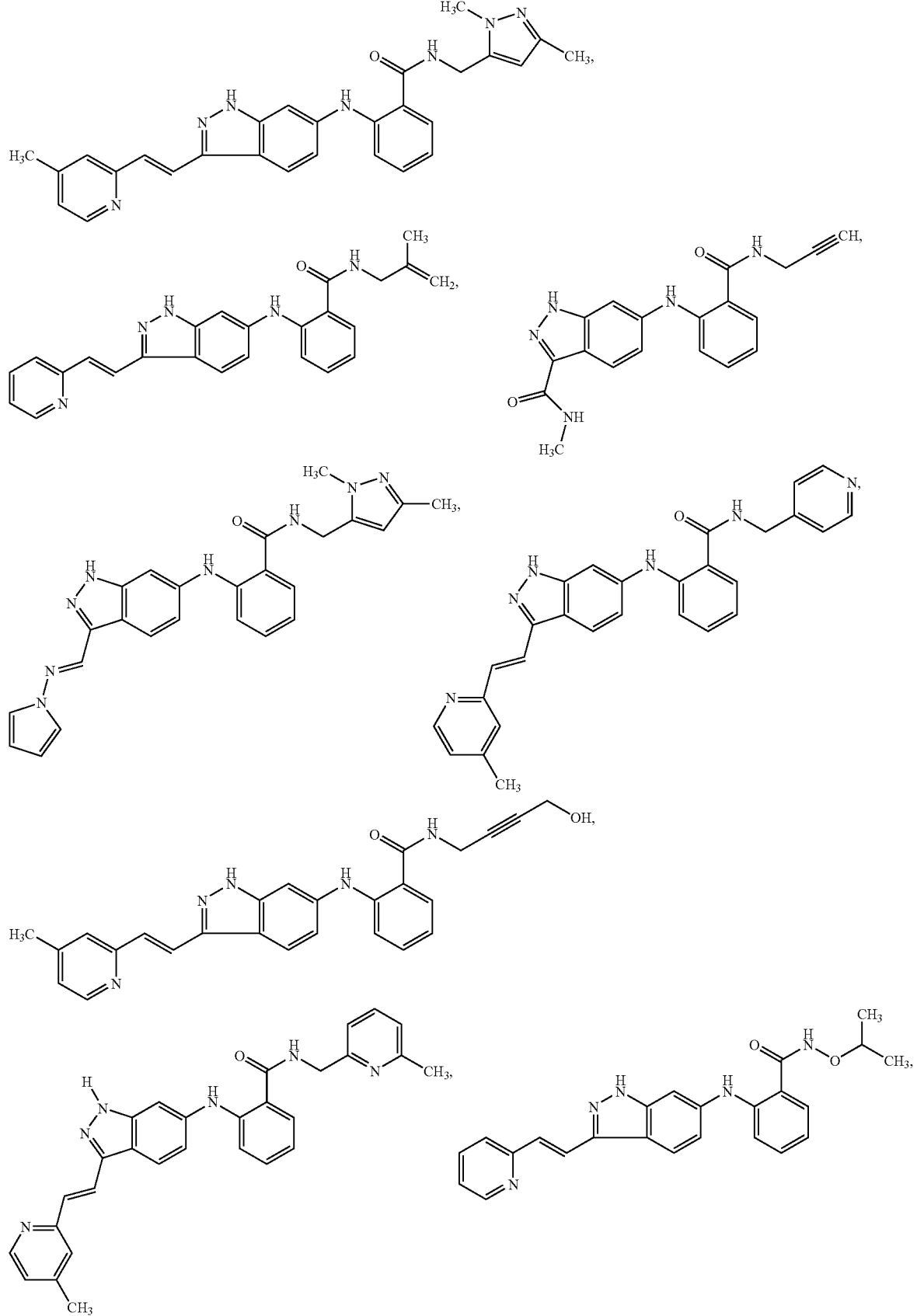

-continued
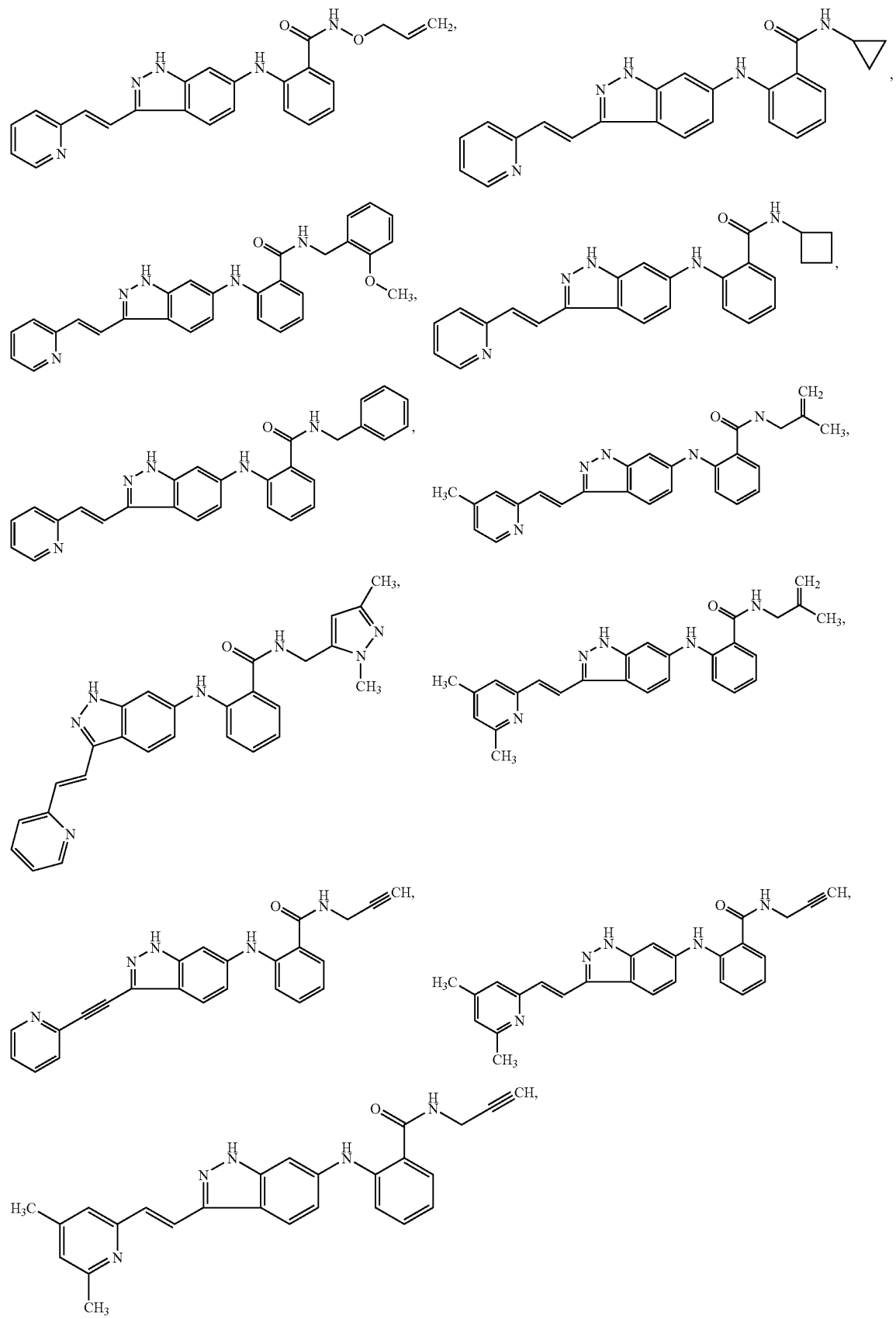

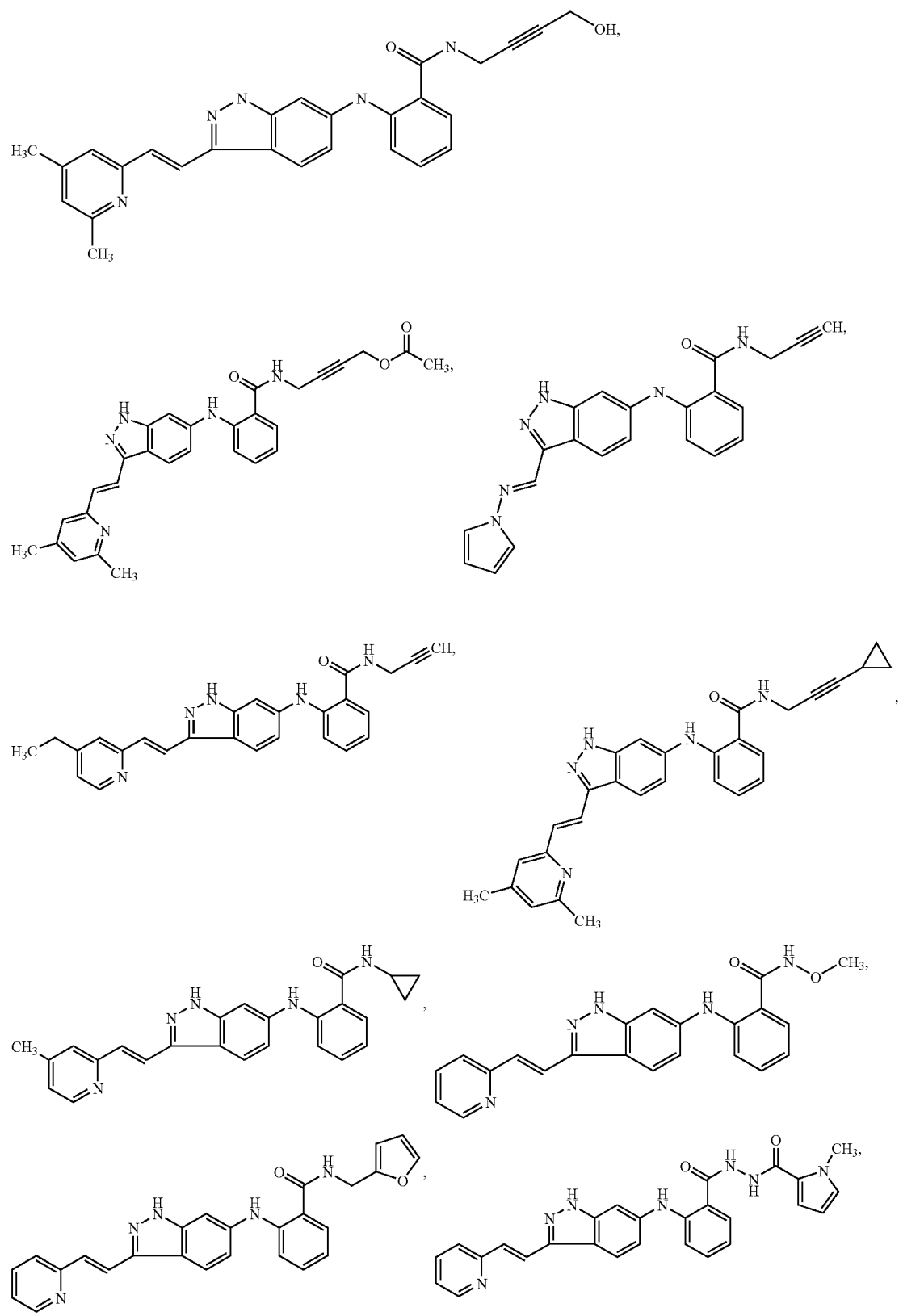

-continued
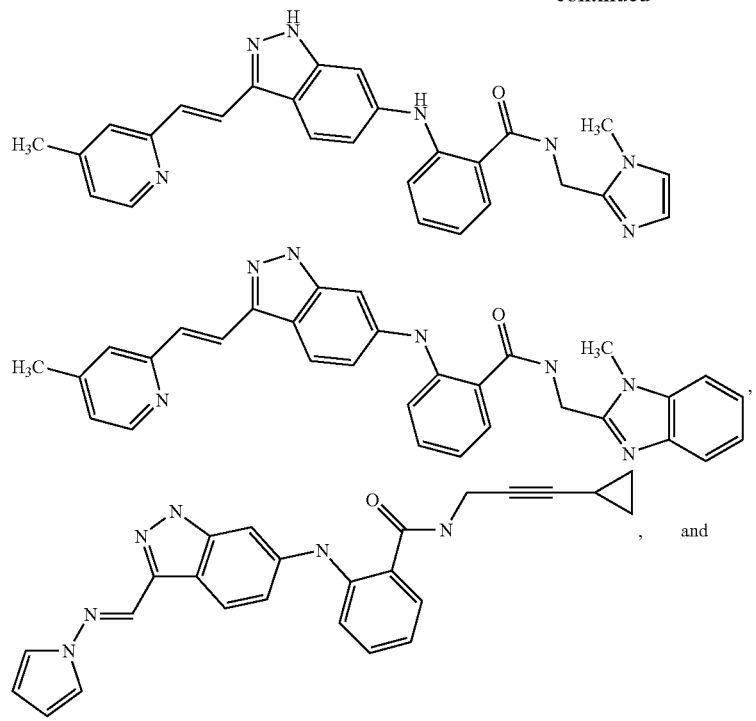
or a pharmaceutically acceptable salt or pharmaceutically acceptable solvate thereof.
In another embodiment, the present invention relates to a compound represented by the formula
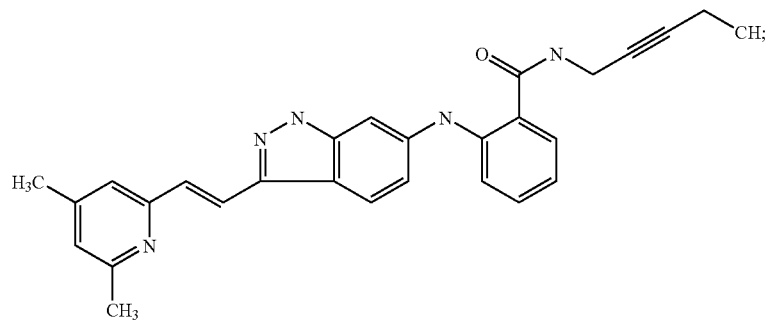
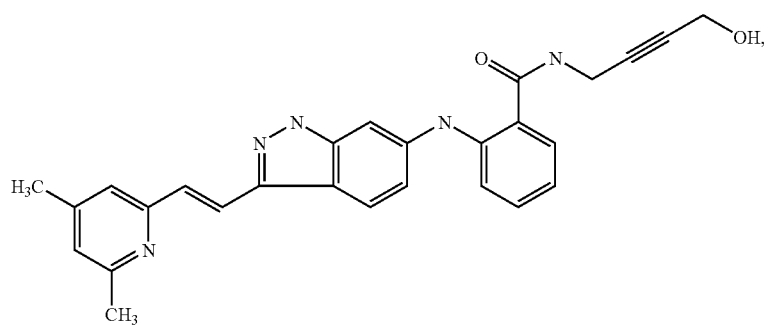
or a pharmaceutically acceptable salt or a pharmaceutically acceptable solvate thereof.

In another embodiment, the present invention relates to 6-(2-Prop-2-ynylcarbamoyl-phenylamino)-1H-indazole-3-carboxylic acid methylamide.

In another embodiment, the present invention relates to 2-{3-[2-(5-Ethyl-pyridin-2-yl)-vinyl]-1H-indazol-6-ylamino}-N-prop-2-ynyl-benzamide.

In another embodiment, the present invention relates to N-Cyclopropyl-2-{3-[(E)-2-(4-methyl-pyridin-2-yl)-vinyl]-1H-indazol-6-ylamino}-benzamide.

In another embodiment, the present invention relates to N-Methoxy-2-[3-((E)-2-pyridin-2-yl-vinyl)-1H-indazol-6-ylamino]-benzamide.

In another embodiment, the present invention relates to N-Allyloxy-2-[3-((E)-2-pyridin-2-yl-vinyl)-1H-indazol-6-ylamino]-benzamide.

In another embodiment, the present invention relates to N-Isopropoxy-2-[3-((E)-2-pyridin-2-yl-vinyl)-1H-indazol-6-ylamino]-benzamide.

In another embodiment, the present invention relates to N-Cyclopropyl-2-[3-((E)-2-pyridin-2-yl-vinyl)-1H-indazol-6-ylamino]-benzamide.

In another embodiment, the present invention relates to 1-Methyl-1H-pyrrole-2-carboxylic acid.

In another embodiment, the present invention relates to N'-(1-{2-[3-((E)-2-pyridin-2-yl-vinyl)-1H-indazol-6-ylamino]-phenyl}-methanoyl)-hydrazide.

In another embodiment, the present invention relates to N-Benzyl-2-[3-((E)-2-pyridin-2-yl-vinyl)-1H-indazol-6-ylamino]-benzamide.

In another embodiment, the present invention relates to N-(2-Methoxy-benzyl)-2-[3-((E)-2-pyridin-2-yl-vinyl)-1H-indazol-6-ylamino]-benzamide.

In another embodiment, the present invention relates to N-Furan-2-ylmethyl-2-[3-((E)-2-pyridin-2-yl-vinyl)-1H-indazol-6-ylamino]-benzamide.

In another embodiment, the present invention relates to N-Cyclobutyl-2-[3-((E)-2-pyridin-2-yl-vinyl)-1H-indazol-6-ylamino]-benzamide.

In another embodiment, the present invention relates to N-(2-Methyl-allyl)-2-[3-((E)-2-pyridin-2-yl-vinyl)-1H-indazol-6-ylamino]-benzamide.

In another embodiment, the present invention relates to N-Prop-2-ynyl-2-[3-((E)-2-pyridin-2-yl-vinyl)-1H-indazol-6-ylamino]-benzamide.

In another embodiment, the present invention relates to 2-{3-[(E)-2-(4,6-Dimethyl-pyridin-2-yl)-vinyl]-1H-indazol-6-ylamino}-N-(4-hydroxy-but-2-ynyl)-benzamide.

In another embodiment, the present invention relates to N-(prop-2-ynyl)-2-{3-[(E)-2-(2,4-dimethyl-pyridin-2-yl)-vinyl]-1H-indazol-6-ylamino}-benzamide.

In another embodiment, the present invention relates to 2-{3-[2-(4,6-Dimethyl-pyndin-2-yl)-vinyl]-1H-indazol-6-ylamino}-N-(2-methyl-allyl)-benzamide.

In another embodiment, the present invention relates to N-(3-Cycloprop-2-ynyl)-2-{3-[(E)-2-(4,6-dimethyl-pyridin-2-yl)-vinyl]-1H-indazol-6-ylamino}-benzamide.

In another embodiment, the present invention relates to Acetic acid 4-(2-{3-[(E)-2-(4,6-dimethyl-pyridin-2-yl)-vinyl]-1H-indazol-6-ylamino}-benzoylamino)-but-2-ynyl ester.

In another embodiment, the present invention relates to 2-{3-[(E)-2-(4,6-Dimethyl-pyridin-2-yl)-vinyl]-1H-indazol-6-ylamino}-N-(4-hydroxy-but-2-ynyl)-nicotinamide.

In another embodiment, the present invention relates to N-(3-Cyclopropyl-prop-2-ynyl)-2-{3-[(E)-2-(4,6-dimethyl-pyridin-2-yl)-vinyl]-1H-indazol-6-ylamino}-nicotinamide.

In another embodiment, the present invention relates to 2-{3-[(E)-2-(4-Methyl-pyridin-2-yl)-vinyl]-1H-indazol-6-ylamino}-N-prop-2-ynyl-benzamide.

In another embodiment, the present invention relates to N-(2-Methyl-allyl)-2-{[(E)-2-(4-methyl-pyridin-2-yl)-vinyl]-1H-indazol-6-ylamino}-benzamide.

In another embodiment, the present invention relates to N-(3-Cycloprop-2-ynyl)-2-{3-[(E)-2-(4-methyl-pyridin-2-yl)-vinyl]-1H-indazol-6-ylamino}-benzamide.

In another embodiment, the present invention relates to 2-{3-[2-(4-Methyl-pyridin-2-yl)-vinyl]-1H-indazol-6-ylamino}-N-pyridin-2-ylmethyl-benzamide.

In another embodiment, the present invention relates to 2-{3-[2-(4-Methyl-pyridin-2-yl)-vinyl]-1H-indazol-6-ylamino}-N-pyridin-4-ylmethyl-benzamide.

In another embodiment, the present invention relates to N-(6-Methyl-pyridin-2-ylmethyl)-2-{3-[2-(4-methyl-pyridin-2-yl)-vinyl]-1H-indazol-6-ylamino}-benzamide.

In another embodiment, the present invention relates to N-(2,5-Dimethyl-2H-pyrazol-3-ylmethyl)-2-{3-[(E)-2-(4-methyl-pyridin-2-yl)-vinyl]-1H-indazol-6-ylamino}-benzamide.

In another embodiment, the present invention relates to N-(1-Methyl-1H-benzoimidazol-2-ylmethyl)-2-{3-[(E)2-(4-methyl-pyridin-2-yl)-vinyl]-1H-indazol-6-ylamino}-benzamide.

In another embodiment, the present invention relates to N-(1-Methyl-1H-imidazol-2-ylmethyl)-2-{3-[2-(4-methyl-pyridin-2-yl)-vinyl]-1H-indazol-6-ylamino}-benzamide.

In another embodiment, the present invention relates to 2-{3-[(E)-2-(4-Methyl-pyridin-2-yl)-vinyl]-1H-indazol-6-ylamino}-N-(4-hydroxy-but-2-ynyl)-benzamide.

In another embodiment, the present invention relates to N-(3-Cyclopropyl-prop-2-ynyl)-2-[3-(pyrrol-1-yliminomethyl)-1H-indazol-6-ylamino]-benzamide.

In another embodiment, the present invention relates to N-(4-Hydroxy-but-2-ynyl)-2-[3-(pyrrol-1-yliminomethyl)-1H-indazol-6-ylamino]-benzamide.

In another embodiment, the present invention relates to N-(2,5-Dimethyl-2H-pyrazol-3-ylmethyl)-2-[3-(pyrrol-1-yliminomethyl)-1H-indazol-6-ylamino]-benzamide.

In another embodiment, the present invention relates to N-Prop-2-ynyl-2-[3-(pyrrol-1-yliminomethyl)-1H-indazol-6-ylamino]-benzamide.

In another embodiment, the present invention relates to N-(4-Hydroxy-but-2-ynyl)-2-[3-(2-pyridin-2-yl-vinyl)-1H-indazol-6-ylamino]-benzamide.

In another embodiment, the present invention relates to N-(2,5-Dimethyl-2H-pyrazol-3-ylmethyl)-2-[3-(2-pyridin-2-yl-vinyl)-1H-indazol-6-ylamino]-benzamide.

The compounds of the present invention may have asymmetric carbon atoms. The carbon-carbon bonds of the compounds of the present invention may be depicted herein using a solid line (—), a solid wedge (———), or a dotted wedge (·······). The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present. Solutions of individual stereoisomeric compounds of the present invention may rotate plane-polarized light. The use of either a "(+)" or "(−)" symbol in the name of a compound of the invention indicates that a solution of a particular stereoisomer rotates plane-polarized light in the (+) or (−) direction, as measured using techniques known to those of ordinary skill in the art.

The inventive compounds of the present invention relate to a method of modulating and/or inhibiting the kinase activity of VEGF-R, FGF-R, a CDK complex, CHK1, LCK, TEK, FAK, and/or phosphorylase kinase by administering a compound of the present invention, or a pharmaceutically acceptable salt or pharmaceutically acceptable solvate thereof. Preferred compounds of the present invention may have selective kinase activity—i.e., they possess significant activity against one or more specific kinases while possessing less or minimal activity against one or more different kinases.

The inventive compounds of the present invention are useful for treating hyperproliferative disorders, such as ophthalmic diseases and cancer, and mediating the activity of protein kinases. More particularly, the compounds are useful as anti-angiogenesis agents and as agents for modulating and/or inhibiting the activity of protein kinases, thus providing treatments for ophthalmic diseases and cancer or other diseases associated with cellular proliferation mediated by protein kinases.

The inventive compounds of the present invention relate to pharmaceutical compositions, each comprising an effective amount of an agent selected from compounds of the present invention and pharmaceutically acceptable salts or pharmaceutically acceptable solvates thereof; and a pharmaceutically acceptable carrier or vehicle for such agent. The invention further provides methods of treating ophthalmic diseases/conditions and cancer as well as other disease states associated with unwanted angiogenesis and/or cellular proliferation, comprising administering effective amounts of such an agent to a patient in need of such treatment.

The inventive compounds of the present invention are useful for treating ophthalmic diseases, for example, age related macular degeneration (ARMD or AMD), retrolental fibroblasia, choroidal neovascularization (CNV), corneal neovascularization, retinopathies (e.g., diabetic retinopathy, vitreoretinopathy, retinopathy of prematurity), retinitis (e.g., cytomegalovirus (CMV) retinitis), uveitis, macular edema, and glaucoma.

Thus, within one aspect of the present invention methods are provided for treating neovascular diseases of the eye such as corneal neovascularization (including corneal graft neovascularization), comprising the step of administering to a patient a therapeutically effective amount of an anti-angiogenic composition to the cornea. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Anti-angiogenic factors and compositions of the present invention are useful by blocking the stimulatory effects of angiogenesis promoters, reducing or inhibiting abnormal cell growth, reducing endothelial cell division, decreasing endothelial cell migration, and impairing the activity of the proteolytic enzymes secreted by the endothelium.

In a specific embodiment of any of the inventive methods described herein, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

In a particular aspect of this embodiment, the cancer is selected from gastrointestinal stromal tumors, renal cell carcinoma, breast cancer, colorectal cancer, non-small cell lung cancer, neuroendocrine tumors, thyroid cancer, small cell lung cancer, mastocytosis, glioma, sarcoma, acute myeloid leukemia, prostate cancer, lymphoma, and combinations thereof.

In further specific embodiments of any of the inventive methods described herein, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT publication nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties for all purposes.

Examples of anti-tumor agents include mitotic inhibitors, for example vinca alkaloid derivatves such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis (3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis (2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatves thereof such as N-[2-chloro-5-[[(2, 4-diamino-5-methyl-6-quinazolinyl)methyl]amino]benzoyl]-L-aspartic acid, N-[4-[[(2, 4-diamino-5-ethyl-6-quinazolinyl)methyl]amino]benzoyl]-L-aspartic acid, N -[2-chloro-4-[[(2,4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin- 6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R, 3R) 1-[4-(2-chloro-4-fluoro-benzyloxy) -benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2. 1 ]octane-3-carboxylic acid hydroxyamide; 3-endo-3-[4-(4-fluoro-phenoxy)-benzenesulfonylamino]-8-oxa-bicyclo[3.2. 1 ]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 6,534,524, issued Mar. 18, 2003, U.S. Pat. No. 6,531,491, issued Mar. 11, 2003, U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent applications: Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

The composition may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

Specific examples of combination therapy can be found in PCT Publication No. WO 03/015608 and U.S. Provisional Patent Application No. 60/426,386, filed Nov. 15, 2002, the disclosures of which are incorporated herein by reference in their entireties.

DETAILED DESCRIPTION OF INVENTION

Definitions

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; and (4) any tumors that proliferate by receptor tyrosine kinases.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "pharmaceutically acceptable salt(s)", as used herein, unless otherwise indicated, includes salts of acidic or basic groups which may be present in a compound. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "tolyl" represents $CH_3C_6H_5$—.

"DMF" represents dimethyl formamide.

"DIEA" represents di-isopropyl ethyl amine.

"Me" represents methyl or $CH_3$—.

"Et" represents ethyl or $CH_3CH_2$—.

"OAc" represents "—O—C(O)—$CH_3$".

"R-BINAP" represents (R)-(+)-2,2'-Bis(diphenylphosphiono)-1,1'-binaphthyl).

"Pd" represents palladium.

"Dba" represents dibenzanthracene.

"THF" represents tetrahydrofuran.

"TBDM" represents Dimethyl-tert-butyl silyl

"HATU" represents O-(7-Azabenzotriazol-1-yl)-N N,N', N'-tetramethyluronium hexafluorophosphate.

"Ts" represents tosyl.

"Ph" represents phenyl.

"THP" represents tetrahydropyran.

"TFA" represents trifluoroacetic acid.

"TES" represents triethylsilane.

"MTBE" represents tert butyl methyl ether.

"DBU" represents 1,8-Diazabicyclo [5.4.0] Undec-7-ene.
"DPPA" represents Diphenylphosphorylazide.
"DIBAL" represents Di-isobutyl aluminum hydride.
"IBX" represents 1-Hydroxy-1-oxo-benzo[d][1,2]iodoxol-3-one.

The term "h" or hr" represents hour(s).
The term "mg" represents milligrams.
The term "g" represents grams.
The term "μL" represents microliter.
The term "mL" represents milliliter.
The term "L" represents liter.
The term "mmol" represents millimole.
The term "M" represents molar.
The term "min" or "mins" represents minute(s).
The term "conc" represents "concentrated".
The term "Ar" represents aryl.

The terms "comprising" and "including" are used in an open, non-limiting sense.

The inventive agents may be prepared using the reaction routes and synthesis schemes as described below, employing the techniques available in the art using starting materials that are readily available.

In one general synthetic process, compounds of Formula I are prepared according to the following reaction Scheme 1:

6-Nitroindazole (compound V) is treated with iodine and base, e.g., NaOH, in an aqueous/organic mixture, preferably with dioxane. The mixture is acidified and the product isolated by filtration. To the resulting 3-iodo-6-nitroindazole in dichloromethane-50% aqueous KOH at 0° C. is added a protecting group ("Pg") reagent (wherein X=halo), preferably trimethylsilylethoxymethyl chloride (SEM-Cl), and a phase transfer catalyst, e.g., tetrabutylammonium bromide (TBABr). After 1–4 hours, the two phases are diluted, the organics are separated, dried with sodium sulfate, filtered and concentrated. The crude product is purified by silica gel chromatography to give compounds of formula VI. Treatment of compounds of formula VI in a suitable organic solvent with a suitable $R^1$-organometallic reagent, preferably an $R^1$-boronic acid, in the presence of aqueous base, e.g., sodium carbonate, and a suitable catalyst, preferably Pd(PPh$_3$)$_4$ gives, after extractive work-up and silica gel chromatography, compounds of formula VII. The $R^1$ substituent may be exchanged within compounds of formula VII or later intermediates throughout this scheme by oxidative cleavage (e.g., ozonolysis) followed by additions to the resulting aldehyde functionality with Wittig or condensation transformations (typified in Example 42(a–e)). Treatment of compounds of formula VII with a reducing agent, preferably

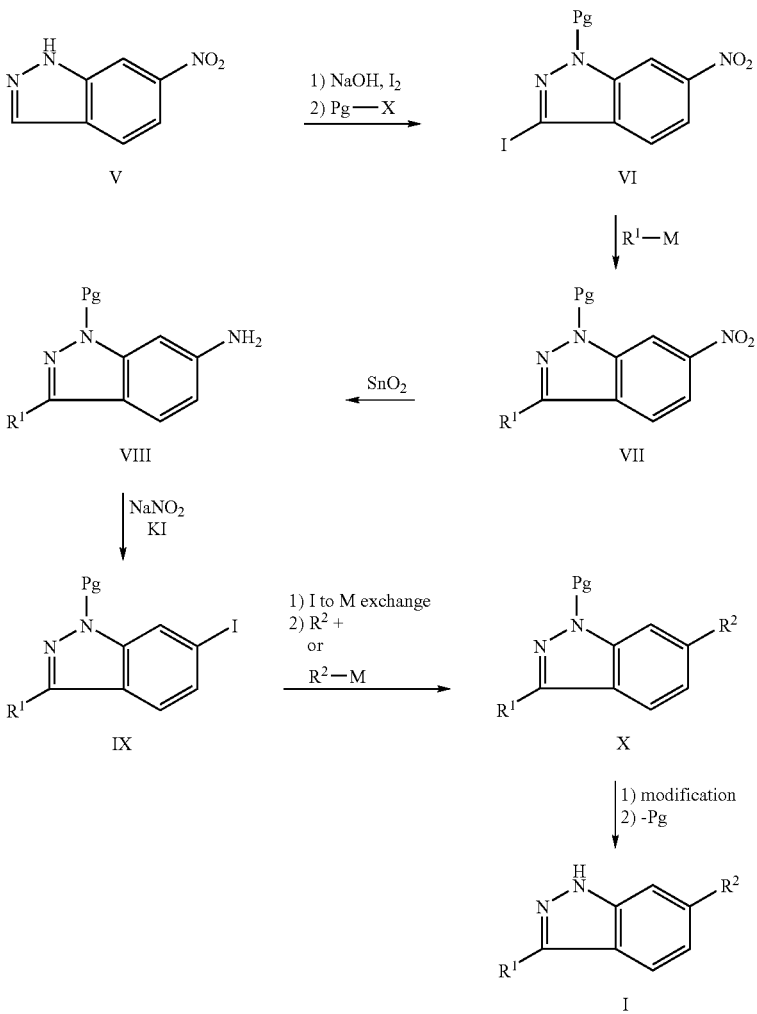

SnCl$_2$, provides, after conventional aqueous work up and purification, compounds of formula VIII. For the series of derivatives where Y=NH or N-lower alkyl, compounds of formula VIII may be treated with aryl or heteroaryl chlorides, bromides, iodides or triflates in the presence of a base, preferably Cs$_2$CO$_3$, and catalyst, preferably Pd-BINAP, (and where Y=N-lower alkyl, with a subsequent alkylation step) to provide compounds of formula X. To produce other Y linkages, sodium nitrite is added to compounds of formula VIII under chilled standard aqueous acidic conditions followed by the addition of potassium iodide and gentle warming. Standard work-up and purification produces iodide compounds of formula IX.

Treatment of compounds of formula IX with an organometallic reagent, e.g., butyllithium, promotes lithium halogen exchange. This intermediate is then reacted with an R$^2$ electrophile, e.g., a carbonyl or triflate, through the possible mediation of additional metals and catalysts, preferably zinc chloride and Pd(PPh$_3$)$_4$ to provide compounds of formula X. Alternatively, compounds of formula IX may be treated with an organometallic reagent such as an organoboronic acid in the presence of a catalyst, e.g., Pd(PPh$_3$)$_4$, under a carbon monoxide atmosphere to give compounds of formula X. Alternatively, for derivatives where Y=NH or S, compounds of formula IX may be treated with appropriate amines or thiols in the presence of base, preferably Cs$_2$CO$_3$ or K$_3$PO$_4$ and a catalyst, preferably Pd-BINAP or Pd-(bis-cyclohexyl) biphenylphosphine to provide compounds of formula X. Conventional functional group interchanges, such as oxidations, reductions, alkylations, acylations, condensations, and deprotections may then be employed to further derivatize this series giving final compounds of Formula I.

The inventive compounds of Formula I may also be prepared according general procedure shown in the following Scheme 2:

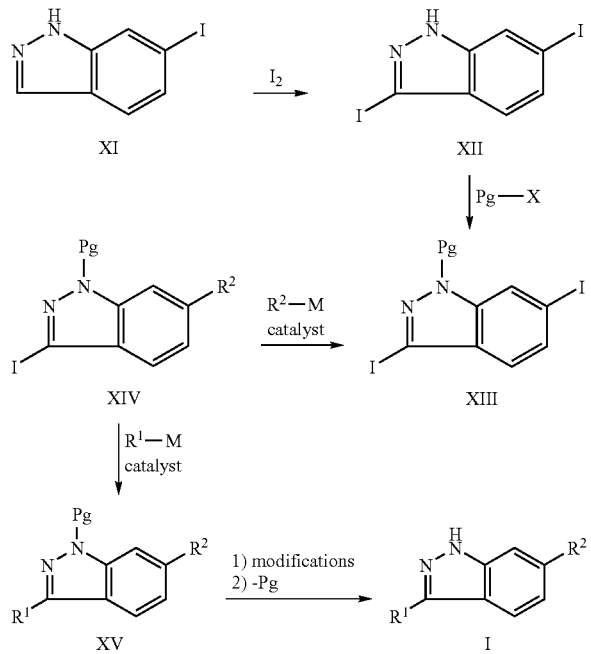

6-Iodoindazole (XI) is treated with iodine and base, e.g., NaOH, in an aqueous/organic mixture, preferably with dioxane. The mixture is acidified and the product XII is isolated by filtration. To the resulting 3,6 di-iodoindazole in dichloromethane-50% aqueous KOH at 0° C. is added a protecting group reagent, preferably SEM-Cl, and a phase transfer catalyst, e.g., TBABr. The two phases are diluted, the organics separated, dried with sodium sulfate, filtered and concentrated. The crude product is purified by silica gel chromatography to give compounds of the formula XIII. Treatment of compounds of formula XIII in a suitable organic solvent with a suitable R$^2$-organometallic reagent, e.g., R$^2$-ZnCl or boron R$^2$-boron reagent and a suitable catalyst, preferably Pd(PPh$_3$)$_4$ gives, after extractive work-up and silica gel chromatography, compounds of formula XIV. Treatment of compounds of formula XIV in a suitable organic solvent with a suitable R$^1$-organometallic reagent (e.g., boron R$^1$-boron reagent or R$^1$-ZnCl), in the presence of aqueous base, sodium carbonate, and a suitable catalyst, preferably Pd(PPh$_3$)$_4$ gives, after extractive work-up and silica gel chromatography, compounds of formula XV. Conventional functional group interchanges, such as oxidations, reductions, alkylations, acylations, condensations and deprotections may then be employed to further derivatize this series giving final compounds of Formula I.

Alternatively, compounds of Formula I where R$^2$ is a substituted or unsubstituted Y—Ar, where Y is O or S may be prepared according to the following general Scheme 3:

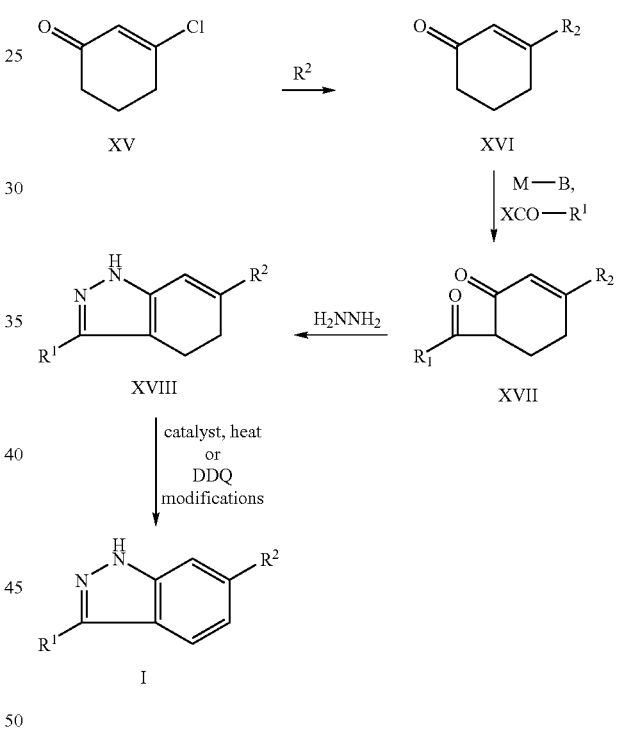

A stirred acetone solution of 3-chloro-cyclohex-2-enone (XV), H—R$^2$, and anhydrous potassium carbonate is refluxed for 15–24 hours, cooled, and filtered. Concentrating and chromatographing the filtrate on silica gel gives 3-R$^2$-cyclohex-2-enone (XVI).

The ketones of formula XVI may be reacted with a suitable base (M-B), preferably lithium bis(trimethylsily) amide, and reacted with R$^1$—CO—X (where X=halogen), which after standard acid work up and purification provides compounds of the formula XVII. This product, in HOAc/EtOH, combined with hydrazine monohydrate, is heated at a suitable temperature for an appropriate time period, preferably at 60–80° C. for 24 hours. After cooling, the mixture is poured into saturated sodium bicarbonate solution, extracted with an organic solvent, concentrated, and purified on silica gel to give compounds of formula XVIII. Compounds of formula XVIII may be oxidized using a variety of known methods, such as catalyst or heat, to give compounds of the Formula I.
An alternative process for synthesizing the compounds of the present invention follows:
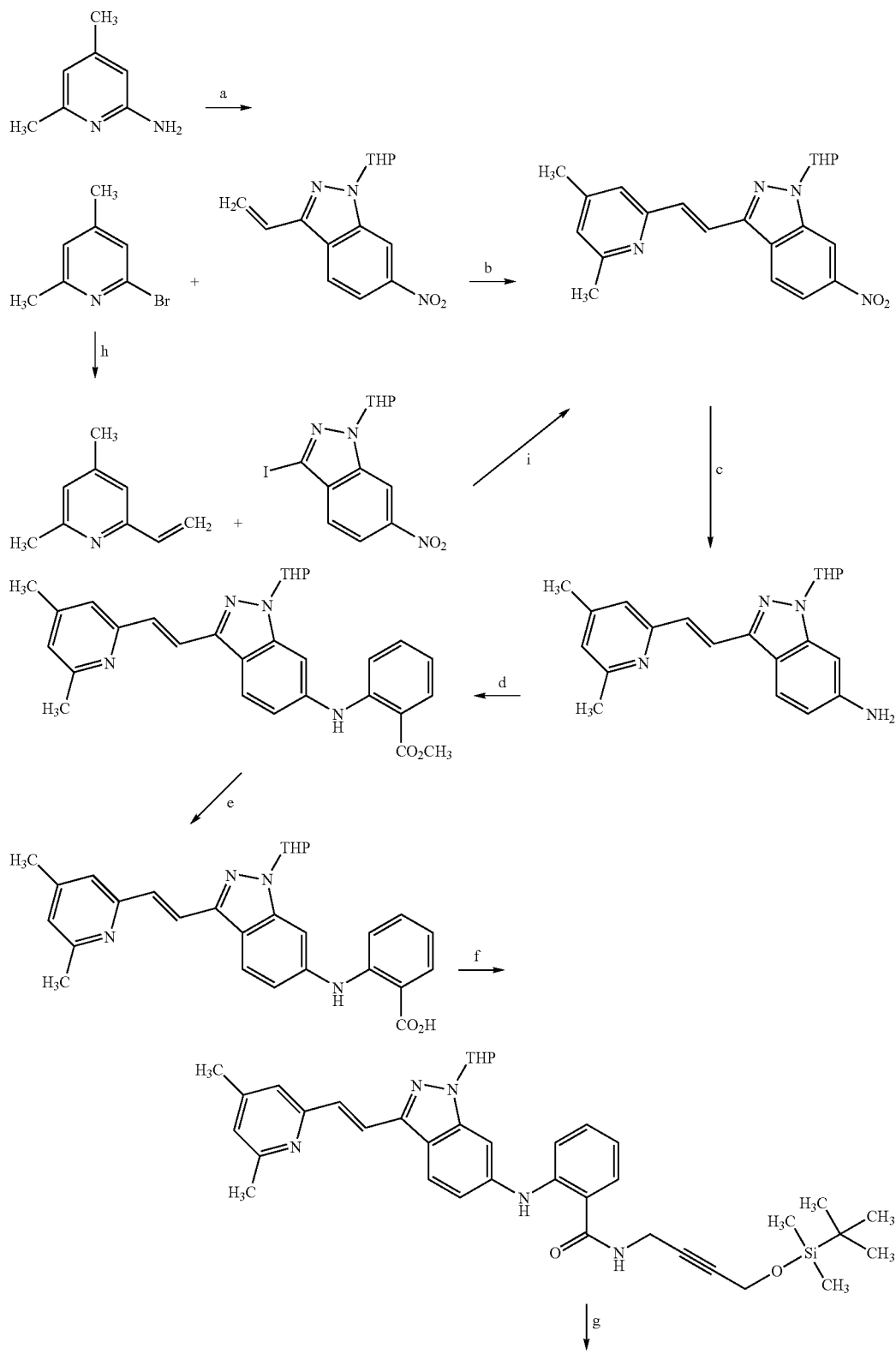

-continued

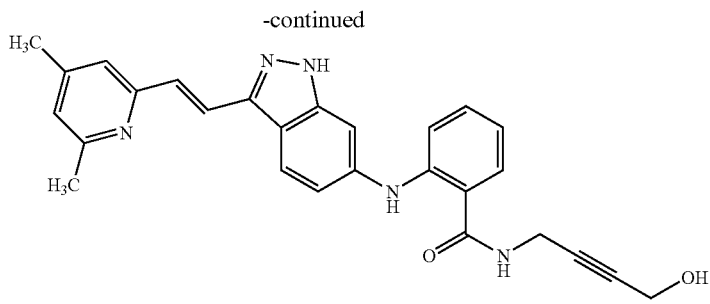

wherein the conditions of the steps a) through i) are as follows:
a) NaNO$_2$, Br$_2$, HBr, 0° C. to −5° C., 4 hours; 48% yield;
b) Pd(OCH$_3$)$_2$, Pd(o-tolyl)$_3$, DIEA, DMF, H$_2$O, degassed, microwave, 110° C., 1 hr; 68% yield;
c) Iron powder, saturated aqueous NH$_4$OH, CH$_3$CH$_2$OH, 45° C., 3 hours; 72% yield;
d) Methyl-2-bromobenzoate, R-BINAP, Pd$_2$(dba)$_3$, Cs$_2$CO$_3$, toluene, degassed, 110° C., overnight (18 hours); 74% yield;
e) KOH in CH$_3$OH:THF:H$_2$O (3:1:1) 70° C., 2–3 hours; quantitative;
f) TBDMS, HATU, NEt$_3$, DMF, room temperature for 2 hours; 80% yield;
g) TsOH (12% TsOH in acetic acid), EtOH (10% aqueous), 2 hours; 44% yield;
h) Tributylvinyltin, Pd(PPh$_3$)$_4$, 2,6-Di-t-butyl-4-methylphenol, toluene, degassed, 105° C., overnight (18 hours); 31% yield;
i) Pd(OAc)$_2$, Pd(o-tolyl)$_3$, DIEA, DMF, degassed, 100° C., overnight (18 hours); approximately 70% yield.

Reagents used in the above synthetic pathways may be commercially available, for example, from Aldrich.

Other compounds of the present invention may be prepared in manners analogous to the general procedures described above or the detailed procedures described in the examples herein. The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See, e.g., Lee et al., *Biochem*, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as bovine serum albumin (BSA) or HAS (human albumin from serum). a multiplicity of peptides including, for example, pentapeptides, decapeptides, pentadecapeptides, and the like. The peptides or proteins can contain the desired number of amino acid residues having free amino groups in their side chains; however, other functional groups, such as sulfhydryl groups or hydroxyl groups, can also be used to obtain stable linkages.

It is understood that while an inventive compounds may exhibit the phenomenon of tautomerism, the formula drawings within this specification expressly depict only one of the possible tautomeric forms. It is therefore to be understood that within the invention the formulae are intended to represent any tautomeric form of the depicted compound and is not to be limited merely to a specific tautomeric form depicted by the formula drawings.

Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

Alternatively, individual stereoisomeric compounds of the present invention may be prepared in enantiomerically enriched form by asymmetric synthesis. Asymmetric synthesis may be performed using techniques known to those of skill in the art, such as the use of asymmetric starting materials that are commercially available or readily prepared using methods known to those of ordinary skill in the art, the use of asymmetric auxiliaries that may be removed at the completion of the synthesis, or the resolution of intermediate compounds using enzymatic methods. The choice of such a method will depend on factors that include, but are not limited to, the availability of starting materials, the relative efficiency of a method, and whether such methods are useful for the compounds of the invention containing particular functional groups. Such choices are within the knowledge of one of ordinary skill in the art.

When the compounds of the present invention contain asymmetric carbon atoms, the derivative salts, prodrugs and solvates may exist as single stereoisomers, racemates, and/or mixtures of enantiomers and/or diastereomers. All such single stereoisomers, racemates, and mixtures thereof are intended to be within the scope of the present invention.

As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, the present invention includes compounds of the indicated structure in both hydrated and non-hydrated forms. Other examples of solvates include the structures in combination with isopropanol, ethanol, methanol, DMSO, ethyl acetate, acetic acid, or ethanolamine.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tryosine kinases. Thus, e.g., a therapeutically effective amount of a compound of the present invention, salt, solvate, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Compounds that potently regulate, modulate, or inhibit the protein kinase activity associated with receptors vascular endothelial growth factor (VEGF), fibrobalst growth factor (FGF), cyclin dependent kinase (CDK) complexes, Tie-2 kinase (TEK), CHK1, Lymphocyte specific kinase (LCK), Focal Adhesion Kinase (FAK), and phosphorylase kinase among others, and which inhibit angiogenesis and/or cellular profileration is desirable and is one preferred embodiment of the present invention. The present invention is further directed to methods of modulating or inhibiting protein kinase activity, for example in mammalian tissue, by administering an inventive agent. The activity of the inventive compounds as modulators of protein kinase activity, such as the activity of kinases, may be measured by any of the methods available to those skilled in the art, including in vivo and/or in vitro assays. Examples of suitable assays for activity measurements include those described in Parast C. et al., BioChemistry, 37, 16788–16801 (1998); Jeffrey et al., Nature, 376, 313–320 (1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of the present invention comprise an effective modulating, regulating, or inhibiting amount of a compound of the present invention and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent is administered in conventional dosage form prepared by combining a therapeutically effective amount of an agent (e.g., a compound of the present invention) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, drop, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the present invention is delivered in a pharmaceutically acceptable ophthalmic vehicle such that the compound is maintained in contact with the ocular surface for a sufficient time period to allow the compound to penetrate the cornea and/or sclera and internal regions of the eye, including, for example, the anterior chamber, posterior chamber, vitreous body, aqueous humor, vitreous humor, cornea, iris/cilary, lens, choroid/retina and sclera. The pharmaceutically acceptable ophthalmic vehicle may be an ointment, vegetable oil, or an encapsulating material. A compound of the invention may also be injected directly into the vitreous humor or aqueous humor.

Further, a compound may be also be administered by well known, acceptable methods, such as subtebnon and/or subconjunctival injections. The sclera and Tenon's capsule define the exterior surface of the globe of the eye. For treatment of ARMD, CNV, retinopathies, retinitis, uveitis, cystoid macular edema (CME), glaucoma, and other diseases or conditions of the posterior segment of the eye, it is preferable to dispose a depot of a specific quantity of an ophthalmically acceptable pharmaceutically active agent directly on the outer surface of the sclera and below Tenon's capsule. In addition, in cases of ARMD and CME it is most preferable to dispose the depot directly on the outer surface of the sclera, below Tenon's capsule, and generally above the macula.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) intramuscular injection or by the above mentioned subtenon or intravitreal injection.

Within particular embodiments of the invention, the compounds may be prepared for topical administration in saline (combined with any of the preservatives and antimicrobial agents commonly used in ocular preparations), and administered in eyedrop form. The anti-angiogenic factor solution or suspension may be prepared in its pure form and administered several times daily. Alternatively, anti-angiogenic compositions, prepared as described above, may also be administered directly to the cornea.

Within alternative embodiments, the composition is prepared with a muco-adhesive polymer which binds to cornea. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. Within further embodiments, the anti-angiogenic factors or anti-angiogenic compositions may b utilized as an adjunct to conventional steroid therapy.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of the compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a franisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel:crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

Example 1(a)

2-(4-Chloro-2-nitro-phenyl)-malonic acid dimethyl ester

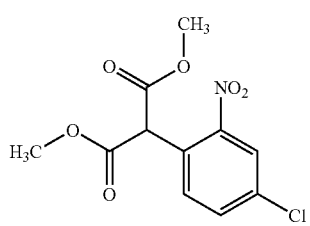

To a stirred slurry of NaH (36.0 g, 1500 mmol) in NMP (1.0 L) was added dimethyl malonate (137.4 mL, 1200 mmol) drop wise. The reaction was cooled as needed to keep the internal temperature below 30 degrees Celsius. After gas evolution ceased, 2,4-dichloronitrobenzene (192 g, 1000 mmol) was added to the reaction. It was carefully heated to 65 degrees Celsius until the reaction was complete as determined by HPLC. The reaction was cooled to room temperature, and then poured over 500 mL ice mixed with 150 mL conc. HCl. The pH of the aqueous layer was adjusted to neutral using 1 N NaOH. The solids were removed by filtering through a coarse fritted filter, and rinsed with water (3 L). The yellow solids were allowed to dry overnight. Yield 261.5 g, 91%.

Example 1(b)

(4-Chloro-2-nitro-phenyl)-acetic acid methyl ester

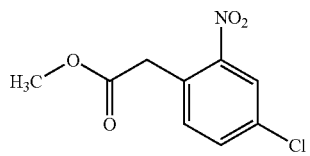

A solution of 2-(4-Chloro-2-nitro-phenyl)-malonic acid dimethyl ester (195 g, 679.4 mmol) in water (100 mL) and NMP (1000 mL) was heated to reflux for 3.5 hours. The solvent was removed by rotary evaporation to an oil. The oil was dissolved in EtOAc, and then washed with water (5×300 mL). The aqueous layer was then extracted with EtOAc (4×300 mL). The organic was washed with water. The organic layers were combined and dried over $MgSO_4$. After removing the solids by filtration, the solvent was evaporated to yield the desired product as a orange/brown solid (160.0 g, 95%).

Example 1(c)

(2-Acetylamino-4-chloro-phenyl)-acetic acid methyl ester

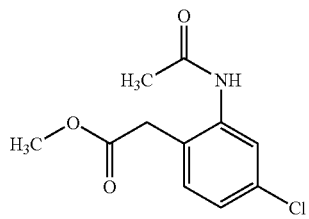

An argon filled flask was charged with (4-Chloro-2-nitrophenyl)-acetic acid methyl ester (40 g, 175 mmol), 10% Pd/C (2.5 g), acetic anhydride (64 mL, 677 mmol), water (9 mL) and acetic acid (150 mL). The flask was vacuum flushed with hydrogen gas at 30 PSI and shook vigorously. After 2 hours, more 10% Pd/C (2 g) was added, and the reaction was complete after a total of 4 hours reaction time. The 10% Pd/C was removed by filtration, and the solvent was removed by rotary evaporation.

Example 1(d)

6-Chloro-1H-indazole-3-carboxylic acid methyl ester

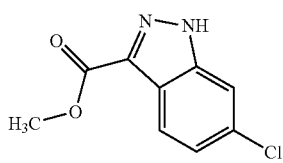

To a solution of (2-Acetylamino-4-chloro-phenyl)-acetic acid methyl ester )32.0 g, 133 mmol) in acetic acid (200 mL)

stirred at 90 degree Celsius was added tert-butyl nitrite (20.5 mL, 172.3 mmol) over 1 hour. The reaction was poured into water (1.4 L) and the solids were recovered by filtration. The yellow precipitate was dissolved in EtOAc, then washed with saturated NaCl. The organic was dried over $MgSO_4$, filtered, and concentrated to a solid. The solids were triturated with hexanes and filtered to afford the desired material (21.63 g, 77%).

Example 1(e)

6-Chloro-1-(tetrahydro-pyran-2-yl)-1H-indazole-3-carboxylic acid methyl ester

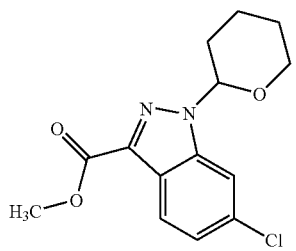

To a slurry of 6-Chloro-1H-indazole-3-carboxylic acid methyl ester (8.3 g, 39.5 mmol) in MeCN (200 mL) was added 3,4-Dihydro-2H-pyran (5.4 mL, 59.3 mmol) and p-toluenesulfonic acid (237 mg, 1.25 mmol). After letting the reaction stir for 10 minutes, saturated $NaHCO_3$ (1 mL) was added and the solvent was removed by rotary evaporation to a volume of 100 mL. The mixture was diluted with EtOAc and washed with water (50 mL) and then with saturated NaCl (50 mL). The organic layer was then dried over $Na_2SO_4$. After the solids were removed by filtration, the organic layer was concentrated to an oil by rotary evaporation. The product was precipitated from the oil using hexanes to yield the desired product (7.667 g, 66% yield).

Example 1(f)

6-(2-Methoxycarbonyl-phenylamino)-1-(tetrahydro-pyran-2-yl)-1H-indazole-3-carboxylic acid methyl ester

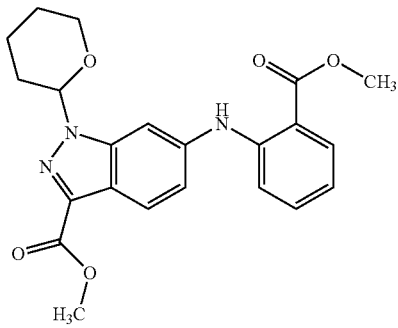

To a solution of 6-Chloro-1H-indazole-3-carboxylic acid methyl ester (2.94 g, 10.0 mmol) in 1,2-dimethoxyethane (30 mL) was added $K_3PO_4$ (5.32 g, 25.0 mmol), tris(dibenzylideneacetone)dipalladium (459 mg, 0.05 mmol), 2-(dicyclohexylphosphino) biphenyl (701 mg, 2.0 mmol), and methyl anthranilate (2.59 mL, 20.0 mmol). The solution was vacuum flushed with argon three times before being heated to 80 degrees Celsius for 18 hours. The reaction was cooled to room temperature and the solids were removed by filtration. After washing the solids with ethyl acetate, the solvent was removed by rotary evaporation. The residual oil was chromatographed (150 g silica gel, 10–30% EtOAc/Hex) to yield 1.23 g (51%) of the desired product.

Example 1(g)

6-(2-Methoxycarbonyl-phenylamino)-1-(tetrahydro-pyran-2-yl)-1H-indazole-3-carboxylic acid

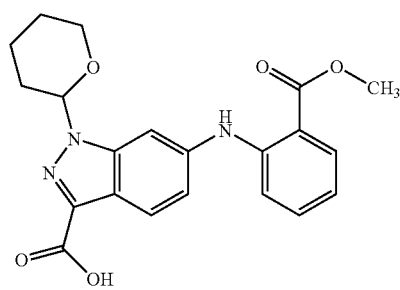

To a solution of 6-(2-Methoxycarbonyl-phenylamino)-1-(tetrahydro-pyran-2-yl)-1H-indazole-3-carboxylic acid methyl ester (2.05 g, 5 mmol) in methanol (18 mL) and tetrahydrofuran (8 mL), was added a solution of sodium hydroxide (0.30 g, 7.5 mmol) in water (2.7 mL). The reaction was stirred at room temperature for 3 hours and was then neutralized with 1 N HCl to a pH of 1. The mixture was diluted with EtOAc (25 mL) and water (25 mL). After separating the layers, the aqueous layer was washed with $CH_2Cl_2$ (3×25 mL). The combined organic extracts were washed with saturated NaCl (100 mL) and then dried over $Na_2SO_4$. The solids were filtered and the liquid was concentrated to an oil. The product was crystallized from EtOAc and Hexanes to yield the desired product (1.616 g, 82%).

Example 1(h)

2-[3-Methylcarbamoyl-1-(tetrahydro-pyran-2-yl)-1H-indazol-6-ylamino]-benzoic acid methyl ester

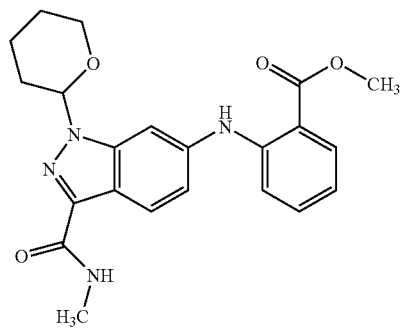

To a solution of 6-(2-Methoxycarbonyl-phenylamino)-1-(tetrahydro-pyran-2-yl)-1H-indazole-3-carboxylic acid (0.50 g, 1.27 mmol) in DMF was added triethylamine (0.42 mL, 3.04 mmol), methylamine (1.9 mL, 3.81 mmol), and HATU (0.578 g, 1.52 mmol). The reaction was stirred for 3 hours and then concentrated by rotary evaporation. The crude oil was chromatographed (50 g silica gel, 25–50% EtOAc/hexanes) to yield the desired product (214 mg, 42%).

Example 1(i)

2-[3-Methylcarbamoyl-1-(tetrahydro-pyran-2-yl)-1H-indazol-6-ylamino]-benzoic acid

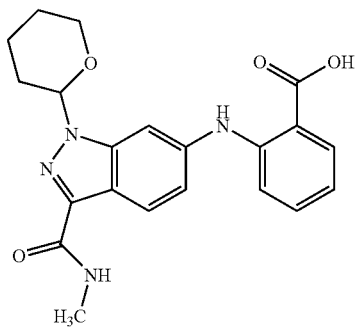

To a solution of 2-[3-Methylcarbamoyl-1-(tetrahydro-pyran-2-yl)-1H-indazol-6-ylamino]-benzoic acid methyl ester (0.20 g, 0.49 mmol) in methanol (1.4 mL) and tetrahydrofuran (0.6 mL) was added a solution of sodium hydroxide (59 mg, 1.47 mmol) in water (0.3 mL). The reaction was heated to 60 degrees Celsius for 1 hour and then was cooled to room temperature. The pH was adjusted with 2 N HCl to a pH of 2. EtOAc (30 mL) and water (30 mL) was added and the layers were separated. The aqueous was extracted with EtOAc (3×20 mL) and the organic layers were combined. After washing with water (15 mL), the organic layer was dried over $Na_2SO_4$. The solids were filtered away, and the organic was evaporated to yield a yellow solid (193 mg, 100%).

Example 1(j)

6-(2-Prop-2-ynylcarbamoyl-phenylamino)-1-(tetrahydro-pyran-2-yl)-1H-indazole-3-carboxylic acid methylamide

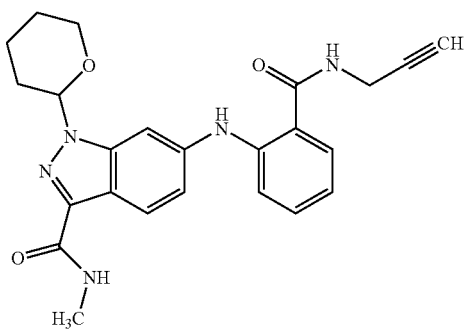

To a solution of 2-[3-Methylcarbamoyl-1-(tetrahydro-pyran-2-yl)-1H-indazol-6-ylamino]-benzoic acid (150 mg, 0.381 mmol) in DMF (3.6 mL) was added propargylamine (0.052 mL, 0.761 mmol), triethylamine(TEA) (0.264 mL, 1.90 mmol), and HATU (217 mg, 0.571 mmol). The reaction was stirred for 4 hours, and then was diluted with EtOAc (30 mL) and water (30 mL). The layers were separated, and the aqueous was extracted with EtOAc (2×20 mL). The combined organics were washed with saturated NaCl (15 mL) and then dried over $Na_2SO_4$. The solids were removed by filtration, and the liquid was concentrated by rotary evaporation to a yellow oil (164 mg, 100%).

Example 1(k)

6-(2-Prop-2-ynylcarbamoyl-phenylamino)-1H-indazole-3-carboxylic acid methylamide

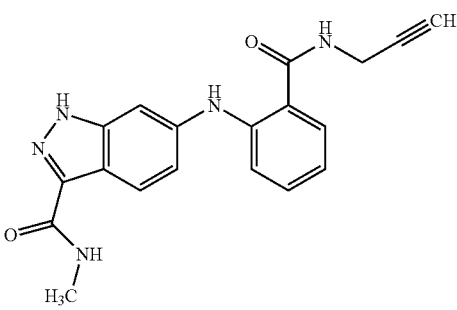

Dissolved 6-(2-Prop-2-ynylcarbamoyl-phenylamino)-1-(tetrahydro-pyran-2-yl)-1H-indazole-3-carboxylic acid methylamide (30 mg) in 1.5 mL of a 90:10:1 mixture of $CH_2Cl_2$:Trifluoroacetate TFA:triethyl silane and heat to reflux for 2 hours. Diluted the solution with toluene (40 mL) and concentrate by rotary evaporation to an oil. Dissolved the oil in DMF (1 mL), and filter using a 0.2-micron syringe filter. Used prep-HPLC to isolate the desired compound (12 mg, 50%). $^1$H NMR ($CDCl_3$-d) δ 9.96 (1H, s), 9.49 (1H, s), 8.28 (1H, d, J=8.85 Hz), 7.47 (1H, m), 7.34 (1H, m), 7.22 (1H, m), 7.15 (1H, dd, J1=8.76 Hz, J2=1.79 Hz), 6.99 (1H, m), 6.86 (1H, t, J=6.97 Hz), 6.31 (1H, m), 4.23 (2H, dd, J1=5.18 Hz, J2=2.54 Hz), 3.49 (3H, s), 2.29 (s,1H).

Anal. Calcd. For $C_{19}H_{17}N_5O_2 \cdot 1.0$ MeOH.0.1 TFA: C, 62.08; H, 5.44; N, 17.92. Found: C, 61.78; H, 5.45; N, 18.04.

Example 2(a)

[6Chloro-1-(tetrahydro-pyran-2-yl)-1H-indazol-3-yl]-methanol

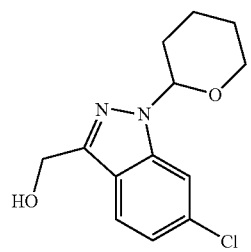

To a solution of 6-Chloro-1H-indazole-3-carboxylic acid methyl ester (2.94 g, 10.0 mmol) in dry $CH_2Cl_2$ (50 mL) cooled to −78 degrees Celsius was added DIBAL-H (3.56 mL, 20.0 mmol) slowly. After the addition was complete, the reaction was allowed to warm to room temperature, where HPLC showed that there was a remaining 10% starting material. Extra DIBAL-H (0.35 mL) was then added and stirred for 10 minutes. The reaction was diluted with EtOAc (1000 mL) and washed with 1 N HCl (2×100 mL). It was further washed with 1 N NaHCO₃ (100 mL), and then with saturated NaCl (100 mL). The organic was dried over MgSO₄, filtered, and then concentrated to a white solid (2.65 g, 99.5%).

Example 2(b)

6-Chloro-1-(tetrahydro-pyran-2-yl)-1H-indazole-3-carbaldehyde

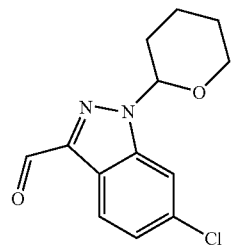

A solution of [6-Chloro-1-(tetrahydro-pyran-2-yl)-1H-indazol-3-yl]-methanol (1.75 g, 6.58 mmol), IBX (2.76 g, 9.87 mmol) and DMSO (27 mL) was stirred overnight. The reaction was diluted in EtOAc and water. The layers were separated, and the aqueous was extracted with EtOAc (3×100 mL). The organics were combined and washed with saturated NaCl (100 mL). The organic was dried over MgSO₄, filtered, and then concentrated to a solid. The solid was dissolved in CH₂Cl₂, and filtered. The organic was evaporated to yield the desired product (1.707 g, 92%).

Example 2(c)

1-(6-Chloro-1H-indazol-3-yl)-2-(5-ethyl-pyridin-2-yl)-ethanol

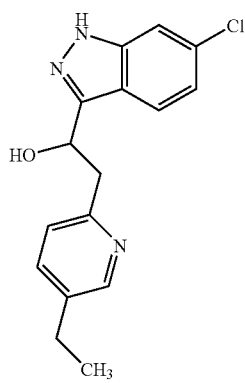

To a stirred solution of 4-ethyl-2-methylpyridine (0.458 g, 3.79 mmol) in THF (4mL) at −50 degrees Celsius, add butyl lithium (1.5 mL, 2.5 M, 3.79 mmol) slowly and stir for 10 minutes. To the reaction, slowly add a solution of 6-Chloro-1H-indazole-3-carbaldehyde (0.5 g, 1.89 mmol) in THF (4 mL). After stirring for 10 minutes, the reaction was quenched with 1 N citric acid (10 mL). The mixture was diluted with EtOAc (50 mL), water (20 mL), and saturated NaCl (10 mL). The layers were separated, and the aqueous was extracted with EtOAc (3×15 mL). The organics were combined and washed with saturated NaCl (20 mL). After drying the organic layer over Na₂SO₄, the solids were removed by filtration and the liquid was concentrated to an oil by rotary evaporation. Chromatography (40 g silica gel, 60–100% EtOAc/hex) yields the desired product (142 mg, 32%) and recovered 6-Chloro-1H-indazole-3-carbaldehyde (348 mg).

Example 2(d)

6-Chloro-3-[2-(5-ethyl-pyridin-2-yl)-vinyl]-1H-indazole

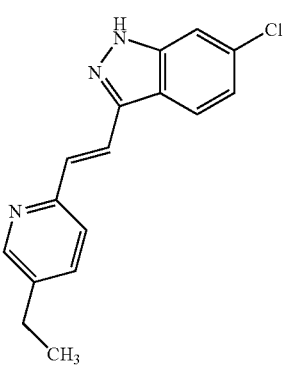

To a stirred solution of 1-(6-Chloro-1H-indazol-3-yl)-2-(5-ethyl-pyridin-2-yl)-ethanol (232 mg, 0.60 mmol) in CH₂Cl₂ was added TEA (0.25 mL, 1.81 mmol) and mesyl chloride (0.070 mL, 0.90 mmol). The reaction was stirred for 30 minutes, and then DBU (2 mL) was added. The reaction was refluxed for 18 hours and then quenched with 40 mL of 1 N citric acid. The layers were separated, and the aqueous was extracted with 20 mL CH₂Cl₂. The combined organics were dried over Na₂SO₄, filtered, and concentrated by rotary evaporation. Purification by chromatography (12 g silica gel, 50–70% EtOAc/hexanes) yielded the desired compound (135 mg, 71%).

Example 2(e)

2-{3-[2-(5-Ethyl-pyridin-2-yl)-vinyl]-1H-indazol-6-ylamino}-benzoic acid methyl ester

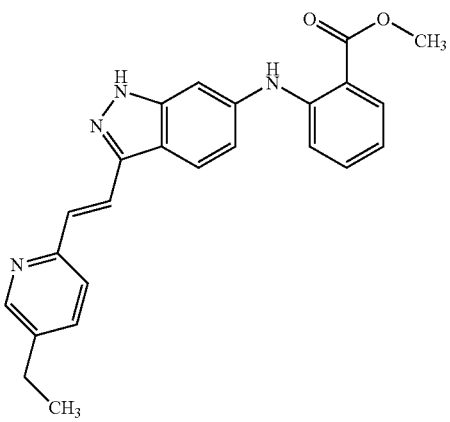

1,2-Dimethoxymethane (2 mL) was added to 6-Chloro-3-[2-(5-ethyl-pyridin-2-yl)-vinyl]-1H-indazole (130 mg, 0.354 mmol), tris(dibenzylideneacetone)dipalladium (16 mg, 0.018 mmol), -(dicyclohexylphosphino)biphenyl (25 mg, 0.071 mmol), $K_3PO_4$ (0.188 g, 0.885 mmol), and methyl anthranilate (0.092 mL, 0.71 mmol). The reaction was vacuum flushed with argon (4×) and then heated to 80 degrees Celsius for 19 hours. The reaction was diluted with EtOAc (20 mL) and filtered through a silica gel plug. After washing with EtOAc (50 mL), the solvent was removed by rotary evaporation. The crude oil was purified by chromatography (40 g silica gel, 30–40% EtOAc/hexanes) to yield the desired product (54 mg, 32%).

Example 2(f)

2-{3-[2-(5-Ethyl-pyridin-2-yl)-vinyl]-1H-indazol-6-ylamino}-benzoic acid

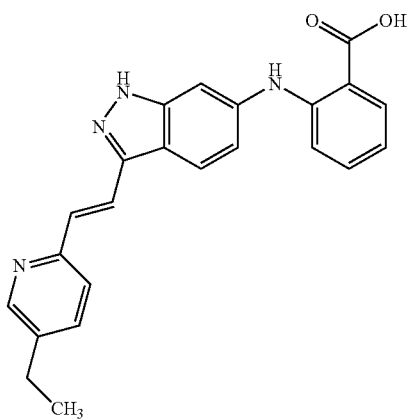

To a solution of 2-{3-[2-(5-Ethyl-pyridin-2-yl)-vinyl]-1H-indazol-6-ylamino}-benzoic acid methyl ester (50 mg, 0.104 mmol) in methanol (0.42 mL) and THF (0.10 mL) was added a solution of sodium hydroxide (12 mg, 0.311 mmol) in water (0.05 mL). The solution was heated to 60 degrees Celsius for 3.5 hours and then neutralized with saturated $NH_4Cl$. The reaction was diluted with water (20 mL), and then extracted with EtOAc (2×20 mL). The combined extracts were first dried over $Na_2SO_4$, and then the solids were removed by filtration. The desired product (48.7 mg, 100%) was recovered after rotary evaporation to remove the solvents.

Example 2(g)

2-{3-[2-(5-Ethyl-pyridin-2-yl)-vinyl]-1H-indazol-6-ylamino}-N-prop-2-ynyl-benzamide

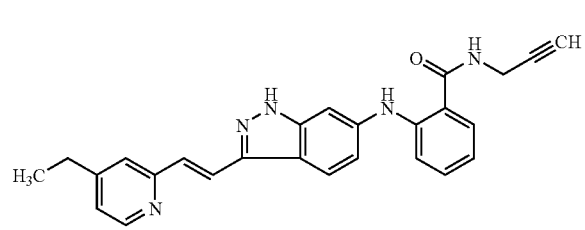

To 2-{3-[2-(5-Ethyl-pyridin-2-yl)-vinyl]-1H-indazol-6-ylamino}-benzoic acid (49 mg, 0.105 mmol) was added 2 mL of a 90:10:1 mixture of $CH_2Cl_2$:TFA:TES. The reaction was stirred at reflux for 1 hour, and then diluted with toluene (20 mL). The solvent was removed by rotary evaporation to yield a thick oil. The oil was dissolved in DMF (1 mL) and to this solution was added TEA (0.072 mL, 0.52 mmol), propargyl amine (0.014 mL, 0.208 mmol), and HATU (59 mg, 0.156 mmol). The reaction was stirred for 3 hours, and then purified by preparatory HPLC to yield the desired product (29 mg, 66%). $^1$H NMR (CDCL$_3$-d): δ 9.83 (1H, s), 8.63 (2H, s), 8.04 (2H, m), 7.68 (2H, s), 7.47 (1H, m), 7.32 (1H, d, J=1.51 Hz), 7.10 (1H, dd, J1=8.67 Hz, J2=1.88 Hz), 6.93 (1H, m), 6.07 (2H, dd, J1=5.09 Hz, J2=2.26 Hz), 3.15 (1H, t, J=2.35 Hz), 2.97 (2H, s), 2.74 (1H, s), 2.29 (1H, s), 1.27 (3H, t, J=7.44 Hz)

Anal. Calcd. for $C_{26}H_{23}N_5O$·0.3 $H_2O$·1.2 TFA: C, 60.51; H, 4.43; N, 12.42. Found: C, 60.38; H, 4.73; N, 12.44.

Example 2(h)

N-Cyclopropyl-2-{3-[(E)-2-(4-methyl-pyridin-2-yl)-vinyl]-1H-indazol-6-ylamino}-benzamide

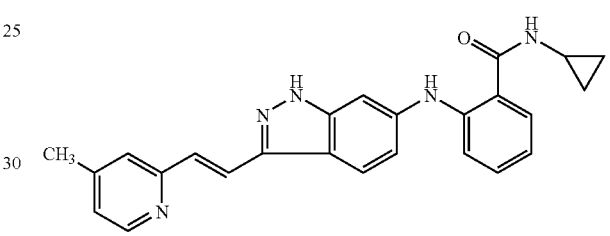

The title compound was prepared analogously to 2-{3-[2-(5-Ethyl-pyridin-2-yl)-vinyl]-1H-indazol-6-ylamino}-N-prop-2-ynyl-benzamide described above, substituting 2,4-dimethyl-pyridine for 4-ethyl-2-methyl-pyridine in the step where 1-(6-Chloro-1H-indazol-3-yl)-2-(5-ethyl-pyridin-2-yl)-ethanol was prepared, and substituting cyclopropyl amine in place of propargyl amine in the final step of the sequence. $^1$H NMR (DMSO-d$_6$): δ 9.85 (1H, s), 8.56 (2H, m), 8.20 (3H, m), 7.53 (5H, m), 7.35 (1H, s), 7.2 (1H, d, J=6.5 Hz), 7.0 (1H, s), 2.83 (1H, m), 0.70 (2H, m), 0.56 (2H, m). ESIMS (M+H$^+$): 410.3.

Example 3(a)

N-Methoxy-2-[3-((E)-2-pyridin-2-yl-vinyl)-1H-indazol-6-ylamino]-benzamide

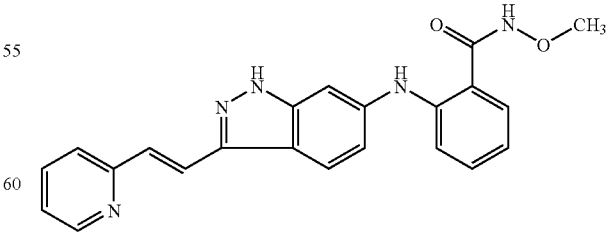

A solution of 2-[3-(2-Pyridin-2-yl-vinyl)-1H-indazol-6-ylamino]-benzoic acid (50.0 mg, 0.084 mmol), O-methylhydroxylamine hydrochloride (15 mg, 0.17 mmol), triethylamine(58 μl, 0.42 mmol), dissolved in DMF (0.8 mL), was treated with HATU (48 mg, 0.13 mmol). The mixture was stirred overnight, then purified by reverse phase HPLC yielding 21.6 mg (67%) of the title compound as a yellow solid. $^1$H NMR (DMSO-d$_6$): δ 9.23 (1H, s), 8.71 (1H, d, J=2.2), 8.05 (4H, m), 7.51 (5H, m), 7.25 (1H, s), 7.10 (1H, d, J=7.7 Hz), 6.91 (1H, m), 5.98 (1H, m), 4.31 (1H, d, J=14.3), 7.20 (1H, d, J=7.3), 4.42 (2H, d, J=3.2). ESIMS (M+H$^+$): 412.1.

Example 3(b)

N-Allyloxy-2-[3-((E)-2-pyridin-2-yl-vinyl)-1H-indazol-6-ylamino]-benzamide

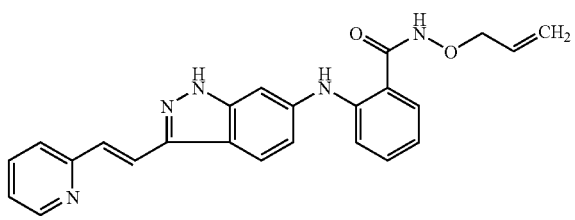

A solution of 2-[3-(2-Pyridin-2-yl-vinyl)-1H-indazol-6-ylamino]-benzoic acid (50.0 mg, 0.084 mmol), O-allyl-hydroxylamine hydrochloride (18.3 mg, 0.17 mmol), triethylamine(58 μl, 0.42 mmol), dissolved in DMF (0.8 mL), was treated with HATU (48 mg, 0.13 mmol). The mixture was stirred overnight, then purified by reverse phase HPLC yielding 25.5 mg (74%) of the title compound as a yellow solid. $^1$H NMR (DMSO-d$_6$): δ 9.28 (1H, s), 8.67 (2H, d, J=3.4), 8.05 (4H, m), 7.48 (5H, m), 7.23 (1H, s), 7.04 (1H, d, J=7.6 Hz), 6.91 (1H, m), 3.69 (3H, s). ESIMS (M+H$^+$): 386.1.

Example 3(c)

N-Isopropoxy-2-[3-((E)-2-pyridin-2-yl-vinyl)-1H-indazol-6-ylamino]-benzamide

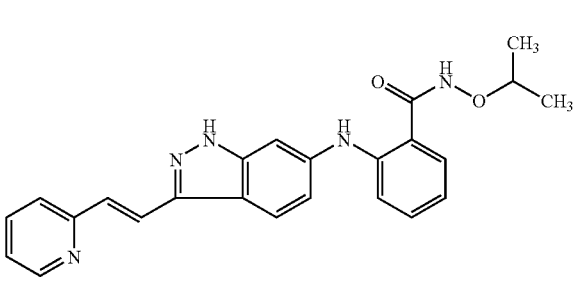

A solution of 2-[3-(2-Pyridin-2-yl-vinyl)-1H-indazol-6-ylamino]-benzoic acid (50.0 mg, 0.084 mmol), O-isopropyl-hydroxylamine hydrochloride (18.7 mg, 0.17 mmol), triethylamine(58 μl, 0.42 mmol), dissolved in DMF (0.8 mL), was treated with HATU (48 mg, 0.13 mmol). The mixture was stirred overnight, then purified by reverse phase HPLC yielding 17.4 mg (50%) of the title compound as a yellow solid. $^1$H NMR (DMSO-d$_6$): δ 9.23 (1H, s), 8.69 (H, d, J=2.1), 8.03 (4H, m), 7.50 (5H, m), 7.23 (1H, s), 7.04 (1H, d, J=6.7 Hz), 6.92 (1H, m), 5.98 (1H, m), 4.13 (1H, m), 1.29 (6H, d, J=8.1). ESIMS (M+H$^+$): 414.1.

Example 3(d)

N-Cyclopropyl-2-[3-((E)-2-pyridin-2-yl-vinyl)-1H-indazol-6-ylamino]-benzamide

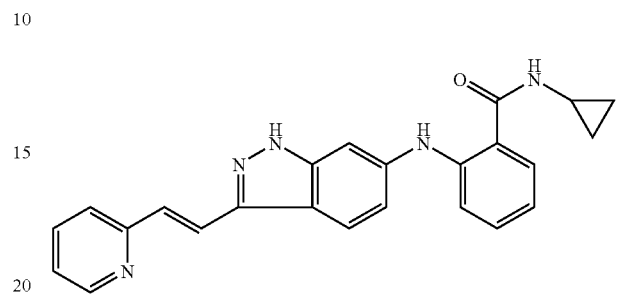

A solution of 2-[3-(2-Pyridin-2-yl-vinyl)-1H-indazol-6-ylamino]-benzoic acid (50.0 mg, 0.084 mmol), cyclopropyl amin (11.6 μL, 0.17 mmol), triethylamine (58 μl, 0.25 mmol), dissolved in DMF (0.8 mL), was treated with HATU (48 mg, 0.13 mmol). The mixture was stirred overnight, then purified by reverse phase HPLC yielding 11.7 mg (35%) of the title compound as a yellow solid. $^1$H NMR (DMSO-d$_6$): δ 9.81 (1H, s), 8.68 (1H, d, J=1.7), 8.51 (1H, s), 8.01 (4H, m), 7.50 (5H, m), 7.24 (1H, s), 7.03 (1H, d, J=5.3), 6.89 (1H, t, J=4.2), 2.84 (1H, m), 0.72 (2H, m), 0.56 (2H, m). ESIMS (M+H$^+$): 396.1.

Example 3(f)

1-Methyl-1H-pyrrole-2-carboxylic acid N'-(1-{2-[3-((E)-2-pyridin-2-yl-vinyl)-1H-indazol4-ylamino]-phenyl}-methanoyl)-hydrazide

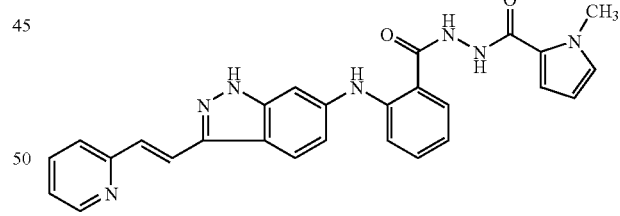

A solution of 2-[3-(2-Pyridin-2-yl-vinyl)-1H-indazol-6-ylamino]-benzoic acid (50.0 mg, 0.084 mmol), 1-methyl-1H-pyrrole-2-carboxylic acid hydrazide (23.3 mg, 0.17 mmol), triethylamine(58 μl, 0.42 mmol), dissolved in DMF (0.8 mL), was treated with HATU (48 mg, 0.13 mmol). The mixture was stirred overnight, then purified by reverse phase HPLC yielding 16.1 mg (40%) of the title compound as a yellow solid. $^1$H NMR (DMSO-d$_6$): δ 10.39 (1H, s), 10.00 (1H, s), 9.52 (1H, s), 8.67 (1H, d, J=2.4), 8.07 (4H, m), 7.77 (1H, d, J=5.2), 7.51 (4H, m), 7.32 (1H, s), 7.09 (1H, d, J=6.3), 6.98 (3H, m), 6.13 (1H, m), 3.87 (3H, s). ESIMS (M+H$^+$):478.1.

Example 3(g)

N-Benzyl-2-[3-((E)-2-pyridin-2-yl-vinyl)-1H-indazol6-ylamino]-benzamide

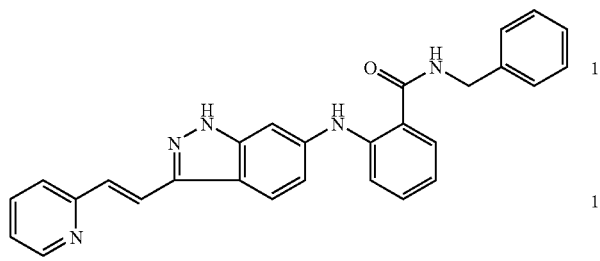

A solution of 2-[3-(2-Pyridin-2-yl-vinyl)-1H-indazol-6-ylamino]-benzoic acid (50.0 mg, 0.084 mmol), benzylamine (18.2 µL, 0.17 mmol), triethylamine (58 µl, 0.42 mmol), dissolved in DMF (0.8 mL), was treated with HATU (48 mg, 0.13 mmol). The mixture was stirred overnight, then purified by reverse phase HPLC yielding 45.2 mg (76%) of the title compound as a TFA salt (1.5 $H_2O$, 2.1 TFA, effective MW=711.98). $^1$H NMR (DMSO-$d_6$): δ 9.86 (1H, s), 9.14 (1H, t, J=5.4), 8.73 (1H, d, J=4.8), 8.29 (4H, m), 7.56 (1H, d, J=7.0), 7.74 (2H, m), 7.89 (2H, m), 7.31 (5H, m), 7.16 (1H, d, J=7.8), 6.93 (1H, t, J=7.3), 4.46 (2H, d, J=6.1). ESIMS (M+H$^+$): 446.5.

Example 3(h)

N-(2-Methoxy-benzyl)-2-[3-((E)-2-pyridin-2-yl-vinyl)-1H-indazol-6-ylamino]-benzamide

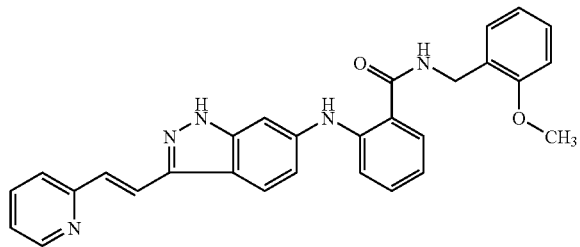

A solution of 2-[3-(2-Pyridin-2-yl-vinyl)-1H-indazol-6-ylamino]-benzoic acid (50.0 mg, 0.084 mmol), o-methoxy-benzylamine (21.8 µL, 0.17 mmol), triethylamine (58 µl, 0.42 mmol), dissolved in DMF (0.8 mL), was treated with HATU (48 mg, 0.13 mmol). The mixture was stirred overnight, then purified by reverse phase HPLC yielding 46 mg (81%) of the title compound as a TFA salt (1.5 $H_2O$, 1.5 TFA, effective MW=673.59). $^1$H NMR (DMSO-$d_6$): δ 9.83 (1H, s), 9.03 (1H, t, J=3.4), 8.70 (1H, d, J=3.7), 8.08 (4H, m), 7.82 (1H, d, J=7.4), 7.49 (4H, m), 7.21 (3H, m), 6.96 (4H, m), 4.48 (2H, d, J=6.3). ESIMS (M+H$^+$): 476.1.

Example 3(i)

N-Furan-2-ylmethyl-2-[3-((E)-2-pyridin-2-yl-vinyl)-1H-indazol-6-ylamino]-benzamide

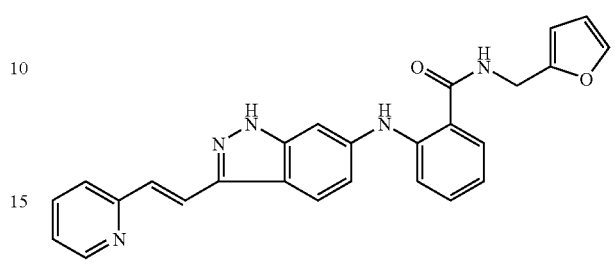

A solution of 2-[3-(2-Pyridin-2-yl-vinyl)-1H-indazol-6-ylamino]-benzoic acid (50.0 mg, 0.084 mmol), C-furan-2-yl-methylamine (19 µL, 0.17 mmol), triethylamine (58 µl, 0.42 mmol), dissolved in DMF (0.8 mL), was treated with HATU (48 mg, 0.13 mmol). The mixture was stirred overnight, then purified by reverse phase HPLC yielding 45 mg (85%) of the title compound as a TFA salt (1.5 $H_2O$, 1.5 TFA, effective MW=633.52). $^1$H NMR (DMSO-$d_6$): δ 9.82 (1H, s), 9.05 (1H, t, J=2.6), 8.73 (1H, d, J=3.7), 8.13 (4H, m), 7.73 (1H, d, J=6.8), 7.57 (2H, m), 7.26 (1H, s), 7.03 (1H, d, J=7.5), 6.40 (1H, m), 6.28 (1H, m), 4.48 (2H, d, J=6.5). ESIMS (M+H$^+$): 436.1.

Example 3(j)

N-Cyclobutyl-2-[3-((E)-2-pyridin-2-yl-vinyl)-1H-indazol-6-ylamino]-benzamide

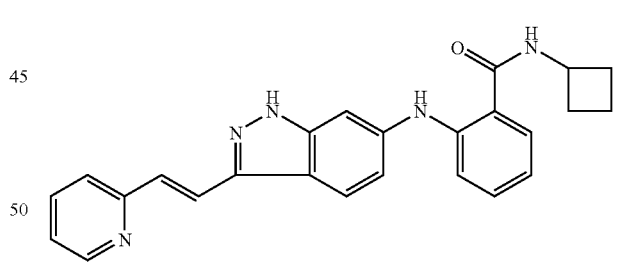

A solution of 2-[3-(2-Pyridin-2-yl-vinyl)-1H-indazol-6-ylamino]-benzoic acid (50.0 mg, 0.084 mmol), cyclobutylamine (18.2 µL, 0.17 mmol), triethylamine (58 µl, 0.42 mmol), dissolved in DMF (0.8 mL), was treated with HATU (48 mg, 0.13 mmol). The mixture was stirred overnight, then purified by reverse phase HPLC yielding 43.2 mg (92%) of the title compound as a TFA salt (1.5 $H_2O$, 1.1 TFA, effective MW=561.92). $^1$H NMR (DMSO-$d_6$): δ 9.78 (1H, s), 8.72 (2H, m), 8.13 (4H, m), 7.70 (1H, d, J=7.1), 7.58 (2H, m), 7.41 (2H, m), 7.27 (1H, s), 6.89 (1H, t, J=4.2), 2.84 (1H, m), 0.72 (2H, m), 0.56 (2H, m). ESIMS (M+H$^+$): 396.1.

Example 3(k)

N-(2-Methyl-allyl)-2-[3-((E)-2-pyridin-2-yl-vinyl)-1H-indazol-6-ylamino]-benzamide

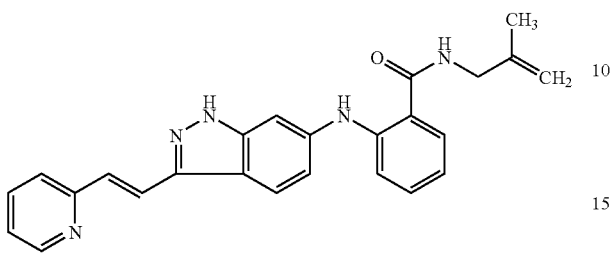

A solution of 2-[3-(2-Pyridin-2-yl-vinyl)-1H-indazol-6-ylamino]-benzoic acid (50.0 mg, 0.084 mmol), 2-methyl-allylamine (16.4 μL, 0.17 mmol), triethylamine (58 μl, 0.42 mmol), dissolved in DMF (0.8 mL), was treated with HATU (48 mg, 0.13 mmol). The mixture was stirred overnight, then purified by reverse phase HPLC yielding 45 mg (91%) of the title compound as a TFA salt (1.6 H$_2$O, 1.3 TFA, effective MW=586.53). $^1$H NMR (DMSO-d$_6$): δ 9.78 (1H, s), 8.72 (2H, m), 8.13 (4H, m), 7.70 (1H, d, J=7.1), 7.58 (2H, m), 7.41 (2H, m), 7.27 (1H, s), 7.06 (1H, d, J=7.1), 6.91 (1H, t, J=7.5), 4.42 (1H, m), 2.22 (2H, m), 2.08 (2H, m), 1.68 (2H, m). ESIMS (M+H$^+$): 410.1.

Example 3(l)

6-Nitro-3-pyridin-2-ylethynyl-1-(2-trimethylsilanyl-ethoxymethyl)-1H-indazole

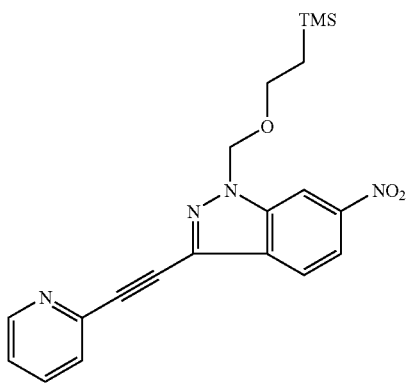

A mixture of 3-Iodo-6-nitro-1-(2-trimethylsilanyl-ethoxymethyl)-1H-indazole (838 mg, 2.0 mmol), 2-ethynyl-pyridine (242 μL, 2.4 mmol), and triethylamine (6.0 mL), were degassed and flushed with argon, then treated with CuI (8 mg, 0.042 mmol), and Pd(PPh$_3$)$_2$Cl$_2$ (16 mg, 0.023 mmol). The resulting mixture was stirred overnight at room temperature, at which time HPLC indicated all starting material had been consumed. The mixture was purified by stripping of volatiles under high vacuum, then passing through a plug of silica eluted with ethyl acetate. The resulting product was used in the next step without further purification. ESIMS (M+H$^+$): 395.1.

Example 3(m)

3-Pyridin-2-ylethynyl-1-(2-trimethylsilanyl-ethoxymethyl)-1H-indazol-6-ylamine

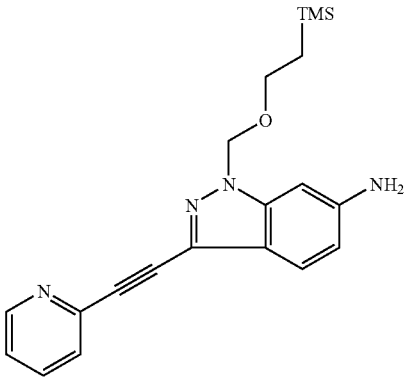

A mixture of 6-Nitro-3-pyridin-2-ylethynyl-1-(2-trimethylsilanyl-ethoxymethyl)-1H-indazole (2 mmol), SnCl$_2$ (1.37 g, 6.0 mmol), water (0.5 mL), and MeOH (10 mL), were stirred in a 60 deg C oil bath for 30 min at which time HPLC indicated complete reduction. The resulting mixture was stripped of methanol, suspended in EtOAc (50 mL) and diluted with 1M NaOH (18 mL). The resulting emulsion was gently extracted EtOAc (10×25 ml). The combined organics were extracted with 1M Na$_2$CO$_3$, brine, dried over MgSO$_4$, concentrated and filtered through a pad of silica eluted with EtOAc. The yield of crude product for two steps was 701 mg, 96% mass recovery. ESIMS (M+H$^+$): 365.1.

Example 3(n)

2-[3-Pyridin-2-ylethynyl-1-(2-trimethylsilanyl-ethoxymethyl)-1H-indazol-6-ylamino]-benzoic acid methyl ester

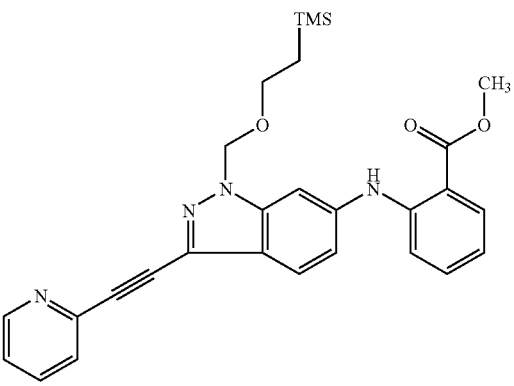

A mixture of 3-Pyridin-2-ylethynyl-1-(2-trimethylsilanyl-ethoxymethyl)-1H-indazol-6-ylamine (560 mg, 1.54 mmol), 2-bromomethylbenzoate (647.5 μL, 4.61 mmol), biphenyl-2-yl-dicyclohexyl-phosphane (107.8 mg, 0.308 mmol), Pd$_2$(dba)$_3$ (70.5 mg, 0.0768 mmol), K$_3$PO$_4$ (816 mg, 3.844 mmol), and dimethoxyethane (1.7 ml), were vacuum flushed with nitrogen, then heated in an oil bath at 70 degrees C. for 24 h. The black mixture was diluted with methylene chloride, and filtered, concentrated, and chromatographed (20% to 40% ethylacetate/hexanes). Yield of yellow/orange oil was 260 mg, 35% for three steps.

Example 3(o)

2-[3-Pyridin-2-ylethynyl-1-(2-trimethylsilanyl-thoxymethyl)-1H-indazol-6-ylamino]-benzoic acid

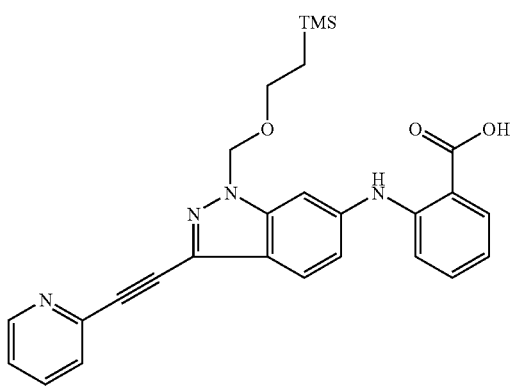

2-[3-Pyridin-2-ylethynyl-1-(2-trimethylsilanyl-ethoxymethyl)-1H-indazol-6-ylamino]-benzoic acid methyl ester (253 mg, 0.517 mmol), was added to a solution of NaOH (62 mg, 1.55 mmol), dissolved in THF (1.0 mL), MeOH (2.25 mL), and water (0.5 mL). The reaction was stirred at room temperature for 1 h, at which time HPLC indicated that all starting material had been consumed. The reaction was neutralized with 1N HCl, extracted with ethylacetate, which was then washed with brine and dried with MgSO$_4$. After concentrating under vacuum, 249 mg of yellow solid was obtained (99% mass recovery). This material was used without further purification. ESIMS M–H$^-$): 483.0.

Example 3(p)

2-[3-Pyridin-2-ylethynyl-1H-indazol6-ylamino]-benzoic acid

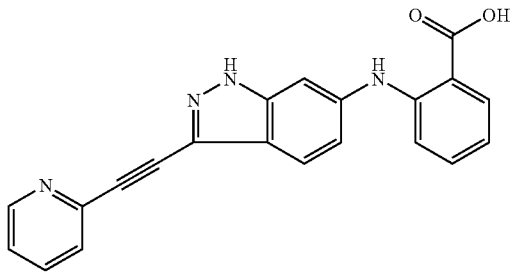

A solution of 2-[3-Pyridin-2-ylethynyl- -(2-trimethylsilanyl-ethoxymethyl)-1H-indazol-6-ylamino]-benzoic acid (231 mg, 0.477), 1M tetrabutylammonium fluoride in THF (3.8 mL, 3.816 mmol), and ethylenediamine (127 μL, 1.908 mmol), were stirred in an oil bath at 80 deg C. for 6 h. The reaction was quenched with acetic acid (218 μL, 3.816 mmol), diluted with water, and extracted with EtOAc (10× 50 mL). The combined organics were washed with brine and dried over MgSO$_4$. After concentrating a solid forms which was triturated with CH$_2$Cl$_2$, giving the product as a yellow powder (124 mg, 73%). ESIMS M–H$^-$): 353.0.

Example 3(q)

N-Prop-2-ynyl-2-[3-((E)-2-pyridin-2-yl-vinyl)-1H-indazol-6-ylamino]-benzamide

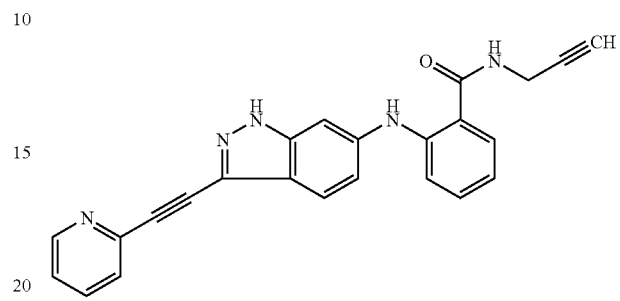

A solution of 2-(3-Pyridin-2-ylethynyl-1H-indazol-6-ylamino)-benzoic acid (41 mg, 0.117 mmol), propargylamine (24 μL, 0.35 mmol), triethylamine (81 μl, 0.58 mmol), dissolved in DMF (0.5 mL), was treated with HATU (89 mg, 0.233 mmol). The mixture was stirred overnight, then purified by reverse phase HPLC yielding 27 mg (59%) of the title compound as a yellow solid. $^1$H NMR (DMSO-d$_6$): δ 9.78 (1H, s), 8.99 (1H, m), 8.61 (1H, d, J=2.1), 7.88 (1H, s), 7.72 (3H, m), 7.43 (4H, m), 7.29 (1H, s), 7.04 (1H, d, J=7.3), 6.91 (1H, t, J=5.2), 4.04 (2H, s), 3.04 (1H, s). ESIMS (M+H$^+$): 392.1.

Example 4(a)

2-Bromo-4,6-dimethyl-pyridine

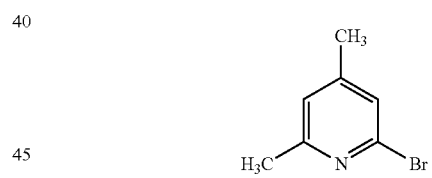

A solution of 48% HBr (aq) (Aldrich, 65 mL, 1.2 mol, 10 eq) was cooled to –5° C. and treated with 4,6-dimethyl-pyridin-2-ylamine (Aldrich, 15.0 g, 0.12 mol. 1.0 eq). The thick white salt mixture was stirred with a mechanical stirrer while bromine (Aldrich, 19.7 mL, 0.38 mol, 3.1 eq) was added dropwise. The resultant red mixture was treated with an aqueous solution (32 mL H$_2$O) of NaNO$_2$ (Aldrich, 22.1 g, 0.32 mol, 2.6 eq) over one hour. The temperature was maintained below 5° C. during the nitrite addition, and then gradually warmed to 20° C. over 2 hours. The reaction mixture was adjusted to pH 14 with NaOH (aq), and extracted with MTBE. The organic extracts were washed with water, brine, dried over magnesium sulfate, filtered and concentrated under reduced pressure. The crude product (29 g of a red oil) was purified by flash chromatography (silica, 350 g) and eluted with 2–7% ethyl acetate-cyclohexane, which gave an orange oil (11.0 g, 48%). $^1$H NMR (DMSO-d$_6$, 300 MHz) δ 7.30 (1H, s), 7.13 (1H, s), 2.39 (3H, s), 2.26 (3H, s). $^{13}$C NMR (DMSO-d$_6$, 75 MHz) δ 159.4, 151.3, 140.9, 125.7, 124.0, 23.7, 20.3. ESI m/z 186/188 (M +H)$^+$.

Example 4(b)

3-[2-(4,6-Dimethyl-pyridin-2-yl)-vinyl]-6-nitro-1-(tetrahydro-pyran-2-yl)-1H-indazole

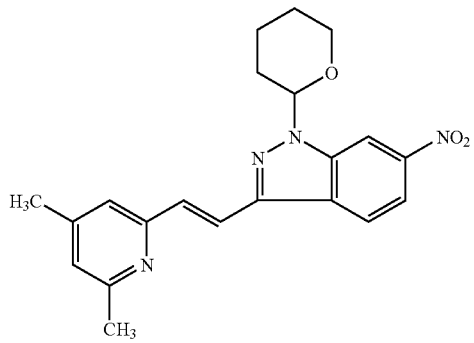

A suspension of 2-bromo-4,6-dimethylpyridine (2.42 g, 13 mmol), 3-vinyl-6-nitro-1-(tetrahydro -pyran-2-yl)-1H-indazole (2.37 g, 8.67 mmol), palladium acetate (0.145 g, 0.65 mmol), tri-ortho-tolylphosphine (0.791 g, 2.6 mmol), and diisopropylethylamine (2.4 mL, 13.8 mmol) in aqueous DMF (85%, 34.5 mL) was degassed with Argon bubbling for 5 minutes followed by sonication for 5 minutes before heating in microwave apparatus (300 watts, 10% power) at 110° C. for 40 minutes. After cooling, the mixture was dropped into cold water. The resulting yellow ppt was collected by filtration. The solids were dissolved in ethyl acetate, dried (sodium sulfate), and concentrated under reduced pressure. The residue was purified on silica gel using a gradient of 0 to 20% ethyl acetate in a mixture of chloroform and hexanes (1:1) as eluent. Product from chromatography was triturated with MTBElhexanes to obtain clean product as yellow solid. Mother liquor was repurified in a similar fashion on silica gel followed by trituration to obtain product in a 68% yield. $^1$H NMR (CDCl$_3$): δ 8.54 (1H, s), 8.15 (1H, d, J=9.4 Hz), 8.08 (1H, dd, J=9.04,1.9 Hz), 7.87 (1H, d, J=16.6 Hz), 7.55 (1H, d, J=16.6 Hz), 7.14 (1H, s), 6.90 (1H, s), 5.82 (1H, dd, J=9.0, 3.0 Hz), 4.08–4.01 (1H, m), 3.84–3.76 (1H, m), 2.56 (3H, s), 2.62–2.54 (1H, m), 2.34 (3H, s), 2.24–2.10 (2H, m), 1.88–1.68 (3H, m).

Example 5

3-[2-(4,6-Dimethyl-pyridin-2-yl)-vinyl]-1-(tetrahydro-pyran-2-yl)-1H-indazol-6-ylamine

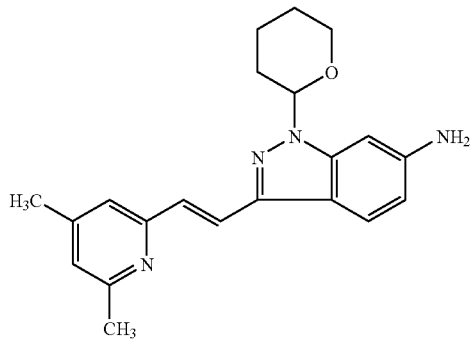

A suspension of 3-[2-(4,6-Dimethyl-pyridin-2-yl)-vinyl]-6-nitro-1-(tetrahydro-pyran-2-yl)-1H-indazole (4.22 g, 11.16 mmol), iron powder (2.719, 48.51 mmol) and sat. aq. NH$_4$Cl (25 ml) in 25 ml of ethanol was heated at 45° C. for 18 hr. The reaction was cooled and filtered through filter paper washing with methanol. The solvents were removed under reduced pressure and the aqueous layer was extracted with EtOAc (2×). The combined organic layers were washed with brine, dried (MgSO$_4$) and concentrated under reduced pressure to give 4.02 g (quantitative) of a rust colored solid and was used without further purification.

$^1$H NMR (DMSO-d6) δ 7.79 (1H, s), 7.74 (1H, d, J=16.4 Hz), 7.35 (1H, d, J=16.4 Hz), 7.29 (1H, s), 6.96 (1H, s), 6.63 (2H, m), 5.57 (1H, dd, J=2.4, 9.5 Hz), 5.44 (2H, broad s), 3.88 (1H, m), 3.67 (1H, m), 2.45 (3H, s), 2.37 (1H, m), 2.29 (3H, s), 1.99 (2H, m), 1.73 (1H, m), 1.57 (2H, m).

Example 6

2-[3-[2-(4,6-Dimethyl-pyridin-2-yl)-vinyl]-1-(tetrahydro-pyran-2-yl)-1H-indazol-6-ylamino]-benzoic acid methyl ester

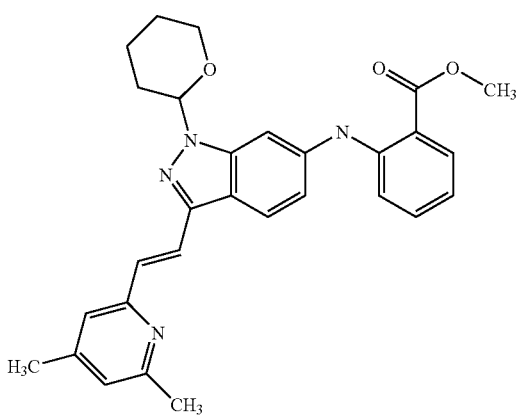

A stirred suspension of 3-[2-(4,6-Dimethyl-pyridin-2-yl)-vinyl]-1-(tetrahydro-pyran-2-yl) -1H-indazol-6-ylamine (870 mg, 2.5 mmol), 2-Bromo-benzoic acid methyl ester (0.44 ml, 3.12 mmol), R-BINAP (78 mg, 0.125 mmol), Pd$_2$(dba)$_3$ (29 mg, 0.03 mmol) and Cesium Carbonate (1.22 g, 3.75 mmol) in toluene( 6 ml) was degassed and heated at 100° C. for 18 hr. The reaction mixture was cooled, poured into sat. NaHCO$_3$ and extracted with EtOAc (2×). The combined organic layers were washed with brine, dried (MgSO$_4$) and concentrated under reduced pressure. The residue was flash chromatographed on silica gel eluting a gradient of 5–10% EtOAc in CH$_2$Cl$_2$ to give 964 mg (80%) of a yellow foam.

$^1$H NMR (DMSO-d$_6$) δ 9.49 (1H, s), 8.13 (1H, d, J=8.7 Hz), 7.94 (1H, dd, J=1.5, 8.0 Hz), 7.85 (1H, d, J=16.4 Hz), 7.58 (1H, d, J=1.5 Hz), 7.48 (1H, d, J=16.4 Hz), 7.47 (1H, m), 7.37 (1H, d, J=7.7 Hz), 7.34 (1H, s), 7.19 (1H, dd, J=1.7, 8.7 Hz), 6.99 (1H, s), 6.89 (1H, t, J=8.1 Hz), 5.83 (1H, d, J=7.2 Hz), 3.88 (3H, s), 3.75 (1H, m), 2.48 (3H, s), 2.41 (2H, m), 2.31 (3H, s), 2.02 (2H, m), 1.75 (1H, m), 1.59 (2H, m). Anal. Calcd for C$_{29}$H$_{30}$N$_4$O$_3$.0.15 EtOAc: C, 71.71; H, 6.34; N, 11.30. Found: C, 71.60; H, 6.14; N, 11.37.

Example 7

2-[3-[2-(4,6-Dimethyl-pyridin-2-yl)-vinyl]-1-(tetrahydro-pyran-2-yl)-1H-indazol-6-ylamino]-benzoic acid

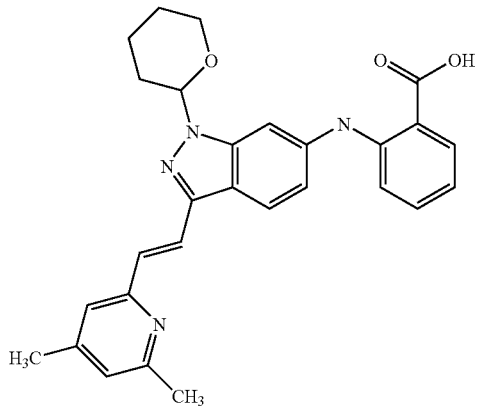

To a stirred solution of 2-[3-[2-(4,6-Dimethyl-pyridin-2-yl)-vinyl]-1-(tetrahydro-pyran-2-yl)-1H-indazol-6-ylamino]-benzoic acid methyl ester (1.98 g, 4.11 mmol) in THF:MeOH (12 ml, 3:1) was added Potassium hydroxide (1.15 g, 20.5 mmol) dissolved in $H_2O$ (3 ml). The reaction was heated at 70° C. for 2 hr, cooled, concentrated under reduced pressure to about 5 ml and diluted with more water. The solution was neutralized with 2N HCl and the precipitate was collected by filtration and washed with water to give 2.00 g (quantitative) of a bright yellow solid. $^1$H NMR (DSMO-$d_6$) δ 513.12 (1H, broad s), 9.82 (1H, s), 8.13 (1H, d, J=8.7 Hz), 7.95 (1H, dd, J=1.5, 8.0 Hz), 7.89 (1H, d, J=16.4 Hz), 7.60 (1H, s), 7.50 (1H, d, J=16.4 Hz), 7.46 (1H, d, J=6.9 Hz), 7.37 (1H, d, J=7.7 Hz), 7.20 (1H, d, J=8.7 Hz), 7.06 (1 H, s), 6.86 (1H, t, J=6.9 Hz), 5.85 (1H, d, J=7.3 Hz), 3.82 (2H, m), 2.50 (3H, s, obscured by dmso), 2.48 (2H, m), 2.34 (3H, s), 2.03 (2H, m), 1.76 (1H, m), 1.59 (2H, m). Anal. Calcd for $C_{28}H_{28}N_4O_3 \cdot 0.5$ KOH: C, 67.72; H, 5.79; N, 11.28.

Found: C, 67.65; H, 5.88; N, 11.07.

Example 8

2-{3-[2-(4,6-Dimethyl-pyridin-2-yl)-vinyl]-1H-indazol-6-ylamino}-benzoic acid p-toluene sulfonate

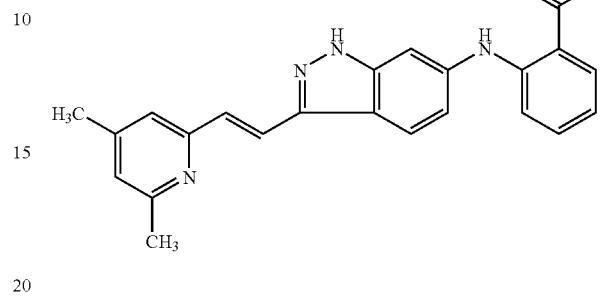

A mixture of 2-[3-[2-(4,6-Dimethyl-pyridin-2-yl)-vinyl]-1-(tetrahydro-pyran-2-yl) -1H-indazol-6-ylamino]-benzoic acid (2 mmol) and p-toluene sufonic acid (10 mmol) in aqueous methanol (90%, 20 mL) was stirred at 70 C. for 18 hr. After cooling, the resulting thick yellow slurry was filtered and the solids washed with methanol to give 2-{3-[2-(4,6-Dimethyl-pyridin-2-yl)-vinyl]-1H-indazol-6-ylamino}-benzoic acid as the tosylate salt in 85% yield as a pale yellow solid. $^1$H NMR (DMSO-$d_6$): δ 13.43 (1H, s), 9.78 (1H, s), 8.24–8.19 (2H, m), 8.09 (1H, d, J=9.04 Hz), 7.95 (1H, dd, J=7.9, 1.1 Hz), 7.62–7.55 (2H, m), 7.49–7.38 (5H, m), 7.20 (1H, dd, J=9.0, 1.9 Hz), 7.09 (2H, d, J=8.3 Hz), 6.86 (1H, dt, J=7.9, 1.1 Hz), 2.67 (3H, s), 2.54 (3H, s), 2.27 (3H, s).

Example 9

N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide

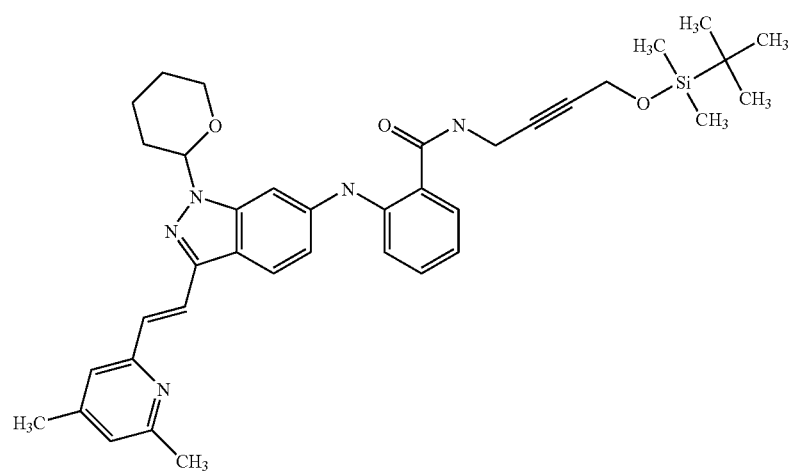

Prepared in a similar manner to that described for Example 33(a) step (v), in U.S. Pat. No. 6,531,491, issued Mar. 11, 2003, herein incorporated by reference in its entirety for all purposes, except using 4-(tert-Butyl-dimethyl-silanyloxy)-but-2-ynylamine and 2-[3-[2-(4,6-Dimethyl-pyridin-2-yl)-vinyl]-1-(tetrahydro-pyran-2-yl)-1H-indazol-6-ylamino]-benzoic acid. $^1$H NMR (DMSO-$d_6$) δ 9.56 (1H, s), 9.01 (1H, t, J=5.7 Hz), 8.06 (1H, d, J=8.7 Hz), 7.81 (1H, d, J=16.4 Hz), 7.66 (1H, d, J=7.5 Hz), 7.41 (4H, m), 7.32 (1H, s), 7.09 (1H, dd, J=1.8, 8.7 Hz), 6.98 (1H, s), 6.89 (1H, t, J=8.0 Hz), 5.79 (1H, dd, J=2.4, 9.2 Hz), 4.28 (2H, s), 4.09 (2H, m), 3.86(1H,m), 3.72 (1H, m), 2.46 (3H, s), 2.42 (1H, m), 2.30 (3H, s), 2.08 (2H, m), 1.74 (1H, m), 1.57 (2H, m), 0.80 (9H, s), 0.03 (6H, s). Anal. Calcd for $C_{38}H_{47}N_5O_3Si$. 0.7 $H_2O$: C, 68.89; H, 7.36; N, 10.57. Found: C, 68.99; H, 7.36; N, 10.21.

Example 10

2-{3-[(E)-2-(4,6-Dimethyl-pyridin-2-yl)-vinyl]-1H-indazol-6-ylamino}-N-(4-hydroxy-but-2-ynyl)-benzamide

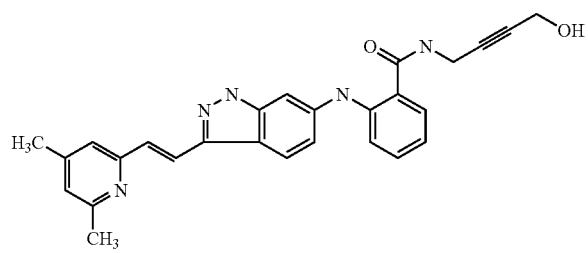

A stirred solution of N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide (737 mg, 1.13 mmol) and p-Toluene-sulfonic acid (8.2 ml, 12% in HOAc) was heated at 70° C. for 2 hr. The reaction was cooled, and cautiously poured into sat. NaHCO$_3$ and extracted with EtOAc (2×). The combined organic layers were washed with brine (2×), dried (MgSO$_4$) and concentrated under reduced pressure. The residue was flash chromatographed on silica gel eluting CH$_2$Cl$_2$:EtOAc:MeOH (1:1:0.1) to give 225 mg (44%) of a white solid. $^1$H NMR (DMSO-$d_6$) δ 12.91 (1H, s), 9.84 (s, 1H), 9.01 (1H, t, J=5.3 Hz), 8.07 (1H, d, J=8.7 Hz), 7.84 (1H, d, J=16.4 Hz), 7.70 (1H, d, J=7.2 Hz), 7.43 (3H, m), 7.31 (1H, s), 7.26 (1H, s), 7.02 (1H, dd, J=1.6, 8.7 Hz), 6.97 (1H, s), 6.89 (1H, t, J=6.7 Hz), 5.12 (1H, t, J=5.8 Hz), 4.10 (2H, d, J=5.3 Hz), 4.07 (2H, d, J=5.8 Hz), 2.47 (3H, s), 2.31 (3H, s).

Anal. Calcd for $C_{27}H_{25}N_5O_2$.1.1 $H_2O$: C, 68.80; H, 5.82; N, 14.86. Found: C, 68.72; H, 5.81; N, 14.65.

Example 11

4-(tert-Butyl-dimethylsilanyloxy)-but-2-ynylamine

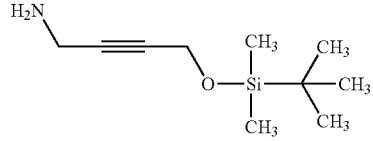

To an ice cold, stirred solution of the known 4-(tert-Butyl-dimethyl-silanyloxy)-but-2-yn-1-ol (3.14 g, 15.7 mmol) in THF (50 ml) was added DBU (2.6 ml, 17.4 mmol) and DPPA (3.8 ml, 17.6 mmol). The solution was warmed to room temperature and stirred under an inert atmosphere overnight. The reaction was poured into sat. NaHCO$_3$ and the layers separated. The aqueous layer was re-extracted with EtOAc (2×) and the combined organic layers were dried (Na$_2$SO$_4$), and concentrated under vacuum. Triphenylphosphine (4.61 g, 17.6 mmol) was added to this crude azide dissolved in THF (50 ml), followed by addition of H$_2$0 (0.44 ml). The resultant solution was stirred overnight at room temperature, concentrated under reduced pressure and the residue was slurried in a 1:1 mixture of Et$_2$O/pet ether. The solids were removed and the filtrate was concentrated and purified by flash chromatography on silica gel eluting CH$_2$Cl$_2$/MeOH (19:1) to give an amber oil. $^1$H NMR (CDCl$_3$) δ 4.19 (2H, t, J=1.9 Hz), 3.33 (2H, t, J=1.9 Hz), 0.79 (9H, s), 0.00 (6H, s).

Example 12

2-[3-[2-(4,6-Dimethyl-pyridin-2-yl)-vinyl]-1-(tetrahydro-pyran-2-yl)-1H-indazol-6-ylamino]-N-prop-2-ynyl-benzamide

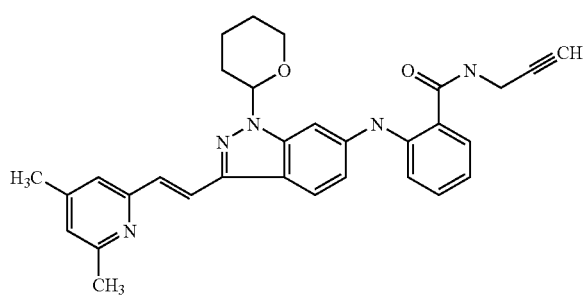

Prepared in a similar manner to that described for Example 6 above, except using 2-[3-[2-(4,6-Dimethyl-pyridin-2-yl)-vinyl]-1-(tetrahydro-pyran-2-yl)-1H-indazol-6-ylamino]-benzoic acid and propargyl amine. $^1$H NMR (DMSO-$d_6$) δ 9.87 (1H, s), 9.04 (1H, t, J=5.8 Hz), 8.08 (1H, d, J=8.7 Hz), 7.83 (1H, d, J=16.4 Hz), 7.69 (1H, d, J=7.5 Hz), 7.44 (4H, m), 7.34 (1H, s), 7.12 (1H, dd, J=1.7, 8.7 Hz), 6.99 (1H, s), 6.91 (1H, t, J=5.8 Hz), 5.81 (1H, dd, J=2.4, 9.2 Hz), 4.07 (2H, dd, J=2.5, 5.7 Hz), 3.88 (1H,m), 3.74 (1H, m), 3.12 (1H, t, J=2.5 Hz), 2.48 (3H, s), 2.43 (1H, m), 2.31 (3H, s), 2.01 (2H, m), 1.74 (1H, m), 1.58 (2H, m).

Anal. Calcd for $C_{31}H_{31}N_5O_2$.1.1 $H_2O$.0.3 TBME: C, 70.73; H, 6.72; N, 12.69. Found: C, 70.56; H, 6.45; N, 12.49.

Example 13

N-(prop-2-ynyl)-2-{3-[(E)-2-(2,4-dimethyl-pyridin-2-yl)-vinyl]-1H-indazol-6-ylamino}-benzamide

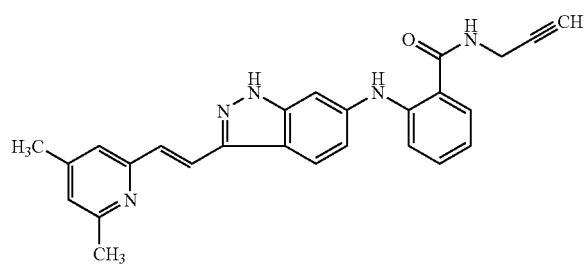

Prepared in a similar manner to that described for Example 7 except using N-(3-Cyclopropyl-prop-2-ynyl)-2-[3-[2-(4,6-dimethyl-pyridin-2-yl)-vinyl]-1-(tetrahydro-pyran-2-yl)-1H-indazol-6-ylamino]-benzamide instead of N-[4-(tert-butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-$d_6$): δ 12.90 (1H, s), 9.78 (1H, s), 9.01 (1H, t, J=5.3 Hz), 8.06 (1H, d, J=8.3 Hz), 7.84 (1H, d, J=16.2 Hz), 7.68 (1H, dd, J=7.9, 1.1 Hz), 7.45–7.36 (3H, m), 7.30 (1H, s), 7.25 (1H, d, J=1.5 Hz), 7.01 (1H, dd, J=8.7, 1.9 Hz), 6.96 (1H, s), 6.88 (1H, dt, J=6.8, 1.9 Hz), 4.04 (2H, dd, J=5.6, 2.6 Hz), 3.11 (1H, t, J=2.6 Hz), 2.46 (3H, s), 2.29 (3H, s).

Example 14

2-[3-[2-(4,6-Dimethyl-pyridin-2-yl)-vinyl]-1-(tetrahydro-pyran-2-yl)-1H-indazol-6-ylamino]-N-(2-methyl-allyl)-benzamide

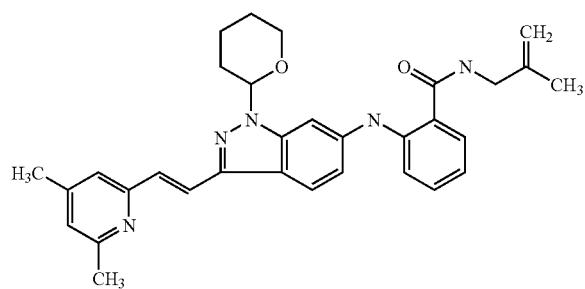

Prepared in a similar manner to that described for Example 6 above, except using 2-[3-[2-(4,6-Dimethyl-pyridin-2-yl)-vinyl]-1-(tetrahydro-pyran-2-yl)-1H-indazol-6-ylamino]-benzoic acid and 2-Methyl-allylamine. $^1$H NMR (DMSO-$d_6$) δ 9.87 (1H, s), 8.82 (1H, t, J=5.8 Hz), 8.07 (1H, d, J=8.7 Hz), 7.82 (1H, d, J=16.4 Hz), 7.74 (1H, d, J=7.3 Hz), 7.43 (4H, m), 7.33 (1H, s), 7.10 (1H, d, J=8.7 Hz), 6.99 (1H, s), 6.92 (1H, t, J=7.8 Hz), 5.80 (1H, dd, J=2.2, 9.2 Hz), 4.83 (2H, d, J=11.8 Hz), 3.83 (4H,m), 2.47 (3H, s), 2.44 (1H, m), 2.31 (3H, s), 2.00 (2H, m), 1.75 (1H, m), 1.73 (3H, s), 1.58 (2H, m).

Anal. Calcd for $C_{32}H_{35}N_5O_2 \cdot 1.09 H_2O$: C, 71.00; H, 6.92; N, 12.94. Found: C, 71.40; H, 6.89; N, 12.54.

Example 15

2-{3-[2-(4,6-Dimethyl-pyridin-2-yl)-vinyl]-1H-indazol-6-ylamino}-N-(2-methyl-allyl)-benzamide

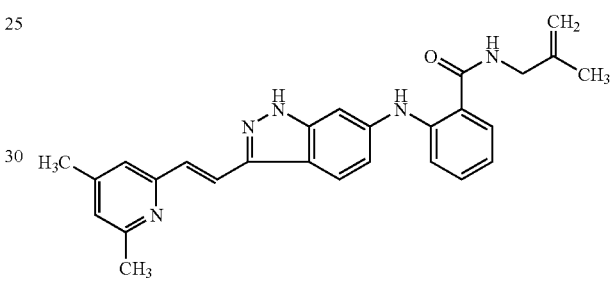

Prepared in a similar manner to that described for Example 7 except using N-(2-Methyl-allyl)-2-[3-[2-(4,6-dimethyl-pyridin-2-yl)-vinyl]-1-(tetrahydro-pyran-2-yl)-1H-indazol-6-ylamino]-benzamide instead of N-[4-(tert-butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-$d_6$) δ 12.89 (1H, s), 9.75 (1H, s), 8.79 (1H, t, J=5.6 Hz), 8.05 (1H, d, J=8.7 Hz), 7.85 (1H, d, J=16.2 Hz), 7.74 (1H, d, J=7.9 Hz), 7.45–7.33 (4H, m), 7.23 (1H, d, J=1.5 Hz), 7.00–6.97 (2H, m), 6.90 (1H, dt, J=7.9, 1.1 Hz), 4.81 (2H, d, J=11.3 Hz), 3.81 (2H, d, J=5.6 Hz), 2.47 (3H, s), 2.30 (3H, s), 1.71 (3H, s).

Alternative Synthetic Scheme

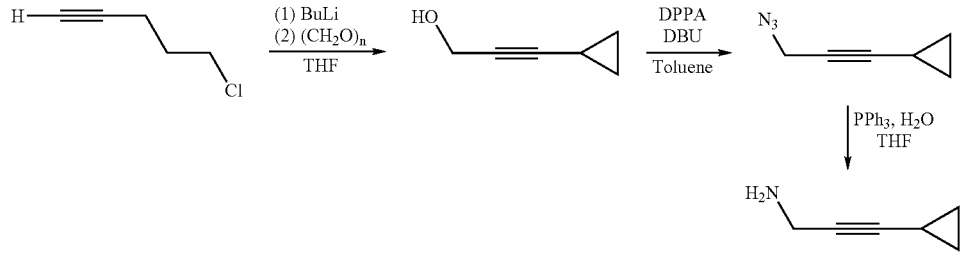

Example 16(a)

Cyclopropyl-prop-2-yn-1-ol

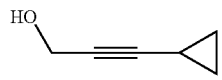

To a round bottom flask containing 70 mL anhydrous THF cooled in −10° C. ice bath was added 65.6 mL 1.6M BuLi in hexanes (105 mmol). 5-Chloro-pent-1-yne (5.13 g, 50 mmol) was introduced slowly while maintaining temperature at −10 to 0° C. The mixture was stirred at 0° C. for two hours under argon. Paraformaldehyde (3 g, 100 mmol) was added as a solid. The mixture was warmed up slowly to room temperature and stirred overnight under argon. The next day, water was added and c.a. 50 mL 1 N aqueous HCl was added. The mixture was extracted with ethyl acetate and the combined organic layers was washed with brine, dried over $Na_2SO_4$, filtered and concentrated. The crude product was purified by column eluting with 20% $Et_2O$ in hexanes to give 3 g 3-cyclopropyl-prop-2-yn-1-ol as an oil (62% yield). $^1$H NMR (CDCl$_3$) δ 4.22 (dd, 2H, J=6.04, 2.01 Hz), 1.46 (t, 1H, J=6.04 Hz), 1.26 (m, 1H), 0.77 (m, 2H), 0.70 (m, 2H).

Example 16(b)

3-Cyclopropyl-prop-2-ynylazide

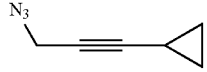

3-Cyclopropyl-prop-2-yn-1-ol (3.28 g, 34.1 mmol) was dissolved in 40 mL toluene, DPPA (11.26 g, 40.9 mmol) was added, followed with DBU (6.24 g, 40.9 mmol) while maintaining temperature with a water bath. The mixture was stirred at room temperature for one hour and was diluted with 100 mL hexane and 15 mL $CH_2Cl_2$. The mixture was washed with water four times and once with brine, dried over $Na_2SO_4$, filtered and concentrated under rotovap with cold water bath to remove most of organic solvent leaving some toluene (product volatile). The residual oil was used for the next step.

$^1$H NMR (CDCl$_3$) δ 3.85 (s, 2H), 1.26 (m, 1H), 0.80 (m, 2H), 0.72 (m, 2H).

Example 16(c)

3-Cyclopropyl-prop-2-ynylamine

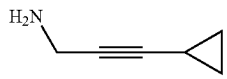

3-Cyclopropyl-prop-2-ynylazide (c.a. 34 mmol) was dissolved in 100 mL THF, 1 mL water was added, followed with addition of PPh$_3$ (13.37 g, 51 mmol) as a solid while maintaining temperature with a water bath. The mixture was stirred at room temperature for one hour. 150 mL 1N aqueous HCl was added to the mixture. The mixture was washed with methylene chloride three times. The aqueous layer was basified with 5 N NaOH to pH 10~12. The mixture was extracted with ethyl acetate. The aqueous layer was checked with TLC staining to monitor progress of extraction of amine to the organic phase. The combined organic layer was dried over $Na_2SO_4$, filtered, and concentrated to give 1.62 g desired product (product volatile, contains residual EtOAc solvent) (50% yield for two steps). $^1$H NMR (CDCl$_3$) δ 3.37 (d, 2H, J=2 Hz), 1.22 (m, 1H), 0.74 (m, 2H): 0.65 (m, 2H).

Example 17

N-(3-Cyclopropyl-prop-2-ynyl)-2-[3-[2-(4,6-dimethyl-pyridin-2-yl)-vinyl]-1-(tetrahydro-pyran-2-yl)-1H-indazol-6-ylamino]-benzamide

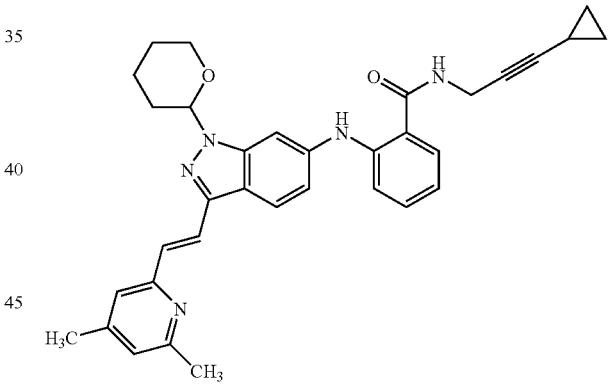

Was prepared in a similar manner to that described for Example 6 above, except using 2-[3-[2-(4,6-dimethyl-pyridin-2-yl)-vinyl]-1-(tetrahydro-pyran-2-yl)-1H-indazol-6-ylamino]-benzoic acid E and 3-Cyclopropyl-prop-2-ynylamine. $^1$H NMR (CDCl$_3$): δ 9.51 (1H, s), 7.97 (1H, d, J=8.7 Hz), 7.81 (1H, d, J=16.6 Hz), 7.51–7.42 (3H, m), 7.34–7.29 (2H, m), 7.16 (1H, s), 7.11 (1H, dd, J=9.0,1.9 Hz), 6.85 (1H, s), 6.81 (1H, dt, J=7.2, 1.1 Hz), 6.23 (1H, t, J=7.2 Hz), 5.61 (1H, dd, J=9.0, 2.6 Hz), 4.17 (2H, dd, J=5.3, 2.3 Hz), 4.07–4.00 (1H, m), 3.75–3.66 (1H, m), 2.63–2.50 (1H, m), 2.54 (3H, s), 2.32 (3H, s), 2.20–2.02 (2H, m), 1.79–1.62 (3H, m), 1.29–1.19 (1H, m), 0.77–0.67 (4H, m).

Example 18

N-(3-Cycloprop-2-ynyl)-2-{3-[(E)-2-(4,6-dimethyl-pyridin-2-yl)-vinyl]-1H-indazol-6-ylamino}-benzamide

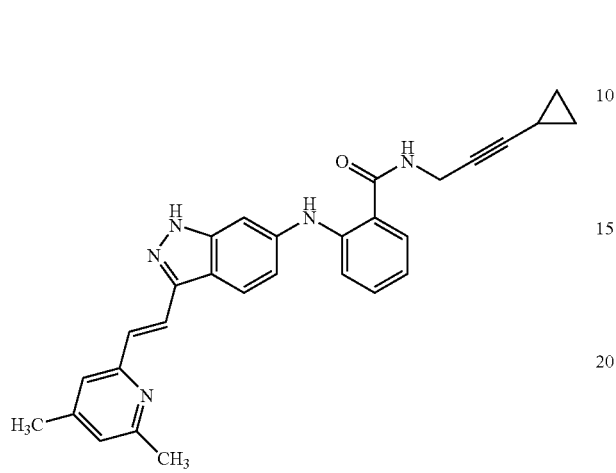

Prepared in a similar manner to that described for Example 7 above, except using 2-[3-[2-(4,6-Dimethyl-pyridin-2-yl)-vinyl]-1-(tetrahydro-pyran-2-yl)-1H-indazol-6-ylamino]-N-prop-2-ynyl-benzamide instead of N-[4-(tert-butyl-dimethyl-silanyloxy)-but-2-ynyl)-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$): 67 12.90 (1H, s), 9.79 (1H, s), 8.91 (1H, t, J=5.6 Hz), 8.06 (1H, d, J=8.7 Hz), 7.83 (1H, d, J=16.2 Hz), 7.68 (1H, dd, J=7.9, 1.1 Hz), 7.49–7.38 (3H, m), 7.29 (1H, s), 7.25 (1H, d, J=1.9 Hz), 6.99 (1H, dd, J=9.0, 2.3 Hz), 6.96 (1H, s), 6.88 (1H, dt, J=7.9, 1.5 Hz), 4.00 (2H, dd, J=5.6, 1.9 Hz), 2.46 (3H, s), 2.29 (3H, s), 1.31–1.23 (1H, m), 0.75–0.70 (2H, m), 0.57–0.52 (2H, m).

Example 19(a)

2-Butyne-1,4-diol, monoacetate

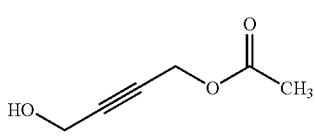

To a solution of butyne-1,4-diol (5 g, 58 mmol) in dry THF at room temperature (RT) was added portion-wise sodium hydride (60% dispersion in oil, 2.32 g, 58 mmol). After 4.3 hr, acetyl chloride (4.12 mL, 58 mmol) was added. After stirring at RT for 22 hr, the mixture was concentrated under reduced pressure. The residue was concentrated twice from toluene before purification on silica gel using ethyl acetate/dichloromethane (1:3) as eluent to give 2-Butyne-1,4-diol, monoacetate as an oil in 49% yield. $^1$H NMR (DMSO-d$_6$) δ 5.23 (1H, bs), 4.70 (2H, t, J=1.8 Hz), 4.09 (2H, s), 2.03 (3H, s).

Example 19(b)

Acetic acid 4-amino-but-2-ynyl ester

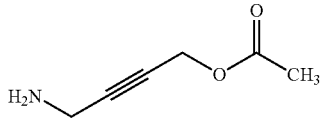

Prepared in a similar manner as described in Example 8 except 2-Butyne-1,4-diol monoacetate was used instead of 4-(tert-Butyl-dimethyl-silanyloxy)-but-2-yn-1-ol. $^1$H NMR (DMSO-d$_6$) δ 4.77 (2H, s), 4.20 (2H, s), 2.04 (3H, s).

Example 20

Acetic acid 4-(2-{3-[(E)-2-(4,6-dimethyl-pyridin-2-yl)-vinyl]-1H-indazol-6-ylamino}-benzoylamino)-but-2-ynyl ester

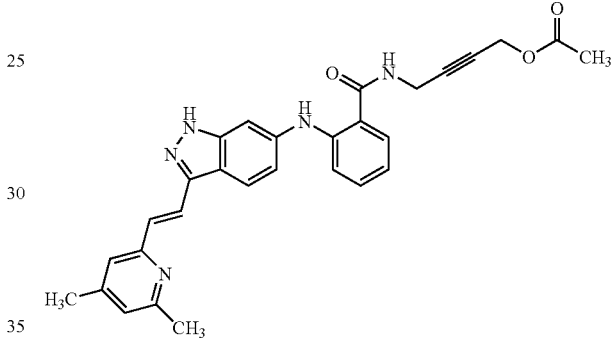

Prepared in a similar manner to that described for Example 6 above, except using 2-[3-[2-(4,6-dimethyl-pyridin-2-yl)-vinyl] 1H-indazol-6-ylamino]-benzoic acid p-toluene sulfonate and Acetic acid 4-amino-but-2-ynyl ester. $^1$H NMR (CD$_3$CN): δ 11.00 (1H, bs), 9.59 (1H, s), 7.99 (1H, d, J=8.6 Hz), 7.86 (1H, d, J=16.4 Hz), 7.58 (1H, d, J=7.8 Hz), 7.49–7.37 (4H, m), 7.32 (1H,s ), 7.21 (1H, s), 7.06 (1H, dd, J=8.8, 1.8 Hz), 6.96 (1H, s), 6.90 (1H, t, J=7.8 Hz), 4.63 (2H, s), 4.16 (2H, d, J=5.6 Hz), 2.49 (3H, s), 2.32 (3H, s), 2.01 (3H, s).

Example 21

2-[3-[(E)-2-(4,6-Dimethyl-pyridin-2-yl)-vinyl]-1-(tetrahydro-pyran-2-yl) -1H-indazol-6-ylamino]-nicotinic acid methyl ester

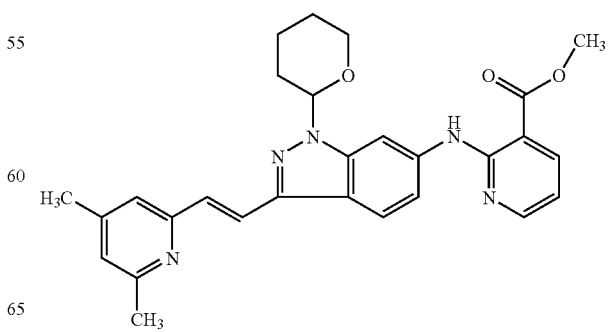

Prepared in a similar manner to that described for Example 3 above except using 2-Bromo-nicotinic acid methyl ester instead of 2-bromo-benzoic acid methyl ester. $^1$H NMR (DMSO-d$_6$): δ 10.36 (1H, s), 8.50 (1H, dd, J=4.7, 1.9 Hz), 8.36 (1H, d, J=1.4 Hz), 8.30 (1H, dd, J=7.8, 2.0 Hz), 8.08 (1H, d, J=8.8 Hz), 7.83 (1H, d, J=16.4 Hz), 7.48 (1H, d, J=7.5 Hz), 7.44 (1H, s), 7.33 (1H, s), 6.98–6.93 (2H, m), 5.80 (1H, d, J=7.0 Hz), 2.93 (3H, s), 3.93–3.90 (1H, m), 3.80–3.75 (1H, m), 2.46 (3H, s), 2.30 (3H, s), 2.10–1.97 (2H, m), 1.89–1.60 (3H, m).

Example 22

2-[3-[(E)-2-(4,6-Dimethyl-pyridin-2-yl)-vinyl]-1-(tetrahydro-pyran-2-yl)-1H-indazol-6-ylamino]-nicotinic acid

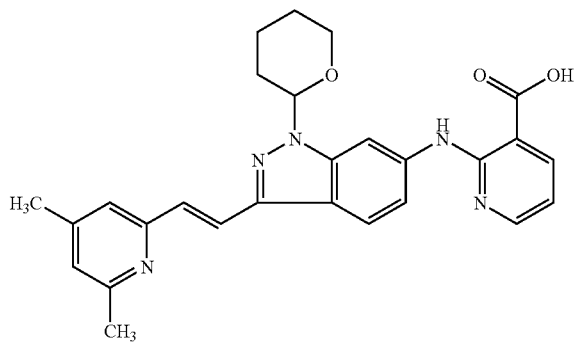

Prepared in a similar manner to that described for Example 4 except using 2-[3-[(E)-2-(4,6-Dimethyl-pyridin-2-yl)-vinyl]-1-(tetrahydro-pyran-2-yl)-1H-indazol-6-ylamino]-nicotinic acid methyl ester instead of 2-[3-[2-(4,6-dim ethyl-pyridin-2-yl)-vinyl]-1-(tetrahydro-pyran-2-yl)-1H-indazol-6-ylamino]-benzoic acid methyl ester. $^1$H NMR (DMSO-d$_6$): δ 10.73 (1H, s), 8.49 (1H, d, J=1.9 Hz), 8.45 (1H, s), 8.31 (1H, dd, J=7.7,1.8 Hz), 8.16–7.97 (3H, m), 7.70 (1H, d, J=16.4 Hz), 7.50 (1H, d, J=8.6 Hz ), 7.37 (1H, s), 6.96 (1H, dd, J=7.7, 4.8 Hz), 5.87 (1H, d, J=8.4 Hz ), 3.95–3.90 (1H, m), 3.79–3.70 (1H, m), 2.63 (3H, s), 2.47 (3H, s), 2.07–1.99 (2H, m), 1.81–1.62 (3H, m).

Example 23

2-{3-[(E)-2-(4,6-Dimethyl-pyridin-2-yl)-vinyl]-1H-indazol-6-ylamino}-N-(4-hydroxy-but-2-ynyl)-nicotinamide

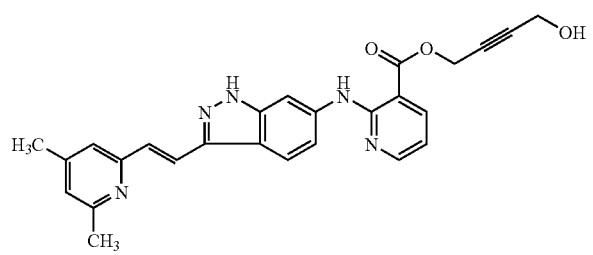

A crude mixture of N-(4-Hydroxy-but-2-ynyl)-2-[3-[2-(4, 6-dimethyl-pyridin-2-yl) -vinyl]-1-(tetrahydro-pyran-2-yl)- 1H-indazol-6-ylamino]-nicotinamide and N-[4-(tert-butyl-dimethyl -silanyloxy)-but-2-ynyl]-2-[3-[2-(4,6-dimethyl-pyrddin-2-yl)-vinyl]-1-(tetrahydro-pyran -2-yl)-1H-indazol-6-ylamino]-nicotinamide was prepared from 2-[3-[(E)-2-(4, 6-Dimethyl-pyridin-2-yl)-vinyl]-1-(tetrahydro-pyran-2-yl)-1H-indazol-6-ylamino]-nicotinic acid and 4-(tert-Butyl-dimethyl-silanyloxy)-but-2-ynylamine in a similar fashion to that described for Example 6 above and subsequently converted to 2-{3-[(E)-2-(4,6-Dimethyl-pyridin-2-yl)-vinyl]-1H-indazol-6-ylamino}-N-(4-hydroxy-but-2-ynyl)-nicotinamide in a similar fashion to that described for Example 7 except using a mixture of N-(4-Hydroxy-but-2-ynyl)-2-[3-[2-(4,6-dimethyl-pyridin-2-yl)-vinyl]-1-(tetrahydro-pyran-2-yl)-1H-indazol-6-ylamino]-nicotinamide and N-[4-(tert-butyl-dimethyl -silanyloxy)-but-2-ynyl]-2-[3-[2-(4,6-dimethyl-pyridin-2-yl)-vinyl]-(tetrahydro-pyran-2-yl)-H-indazol-6-ylamino]-nicotinamide instead of N-[4-(tert-butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$): δ 12.99 (1H, s), 11.21 (1H, s), 9.26 (1H, t, J=5.3 Hz), 8.50 (1H, d, J=1.9 Hz), 8.41 (1H, dd, J=4.9, 1.9 Hz), 8.16 (1H, dd, J=8.3,1.9 Hz), 8.04 (1H, d, J=9.0 Hz), 7.85 (1H, d, J=16.6 Hz), 7.42 (1H, d, J=16.6 Hz), 7.31 (1H,s), 7.06 (1H, dd, J=8.7, 1.5 Hz), 6.96 (1H, s), 6.93 (1H, dd, J=7.5, 4.9 Hz), 5.14 (1H, t, J=5.6 Hz), 4.16 (2H, d, J=5.6 Hz), 4.08 (2H, d, J=7.2 Hz), 2.46 (3H, s), 2.30 (3H, s).

Example 24

2-{3-[2-(4,6-Dimethyl-pyridin-2-yl)-vinyl]-1H-indazol-6-ylamino}-nicotinic acid p-toluene sulfonate

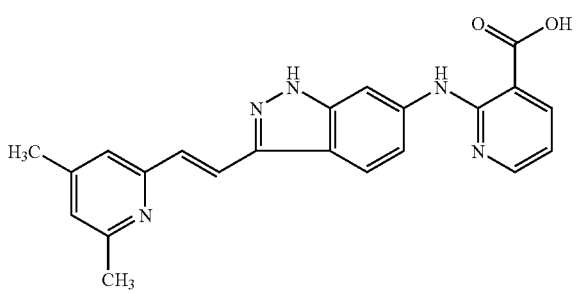

Prepared in a similar manner to that described for Example 5 except using 2-[3-[(E)-2-(4,6-Dimethyl-pyridin-2-yl)-vinyl]-1-(tetrahydro-pyran-2-yl)-1H-indazol-6-ylamino]-nicotinic acid instead of 2-[3-[2-(4,6-Dimethyl-pyridin-2-yl)-vinyl]-1-(tetrahydro-pyran-2-yl)-1H-indazol-6-ylamino]-benzoic acid.

$^1$H NMR (DMSO-d$_6$): δ 13.49 (1H, s), 10.80 (1H, s), 8.63 (1H, d, J=1.5 Hz), 8.49 (1H, dd, J=4.8, 1.9 Hz), 8.31 (1H, dd, J=7.7, 1.9 Hz), 8.24–8.19 (2H, m), 8.06 (1H, d, J=8.8 Hz), 7.60–7.55 (2H, m), 7.46 (2H, d, J=8.1 Hz), 7.22 (1H, dd, J=8.8, 1.7 Hz), 7.09 (2H, d, J=7.9 Hz), 6.95 (1H, dd, J=7.7, 4.7 Hz), 2.66 (3H, s), 2.54 (3H, s), 2.27 (3H, s).

Example 25

N-(3-Cyclopropyl-prop-2-ynyl)-2-{3-[(E)-2-(4,6-dimethyl-pyridin-2-yl)-vinyl]-1H-indazol-6-ylamino}-nicotinamide

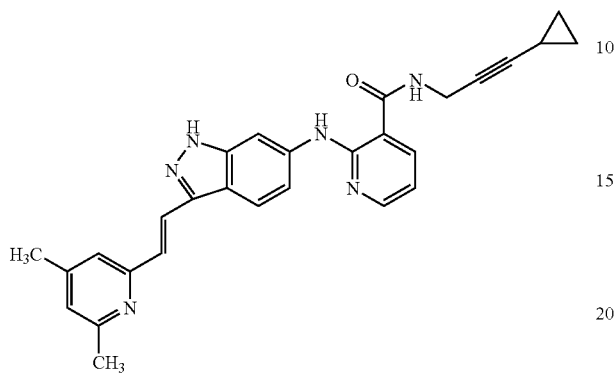

Prepared-in a similar manner to that described for Example 6 above, except using 2-{3-[2-(4,6-Dimethyl-pyridin-2-yl)-vinyl]-1H-indazol-6-ylamino}-nicotinic acid p-toluene sulfonate and 3-Cyclopropyl-prop-2-ynylamine. $^1$H NMR (DMSO-d$_6$): δ 13.01 (1H, s), 11.20 (1H, s), 9.19 (1H, bt), 8.51 (1H, s), 8.40 (1H, d, J=4.9 Hz), 8.15 (1H, d, J=7.5 Hz), 8.05 (1H, d, J=8.7 Hz), 7.83 (1H, d, J=16.4 Hz), 7.42 (1H, d, J=16.4 Hz), 7.31 (1H, s), 7.05 (1H, d, J=8.3 Hz), 6.96 (1H, s), 6.92 (1H, dd, J=7.5, 4.9 Hz), 4.06 (2H, d, J=4.14 Hz), 2.46 (3H, s), 2.29 (3H, s), 1.33–1.28 (1H, m), 0.77–0.72 (2H, m), 0.60–0.55 (2H, m).

Example 26

4-Methyl-2-vinyl-pyridine

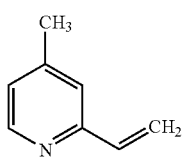

A yellow mixture of 2-bromo-4-methyl-pyridine (Aldrich, 5.2 9, 30.5 mmol, 1.0 eq), 2,6-di-tert-butyl-4-methylphenol (Aldrich, 67 mg, 0.3 mmol, 1 mol %), tributyl-vinyl-stannane (Aldrich, 26.8 mL, 91.5 mmol, 3.0 eq) and tetrakis(triphenylphosphine) palladium (0) (Strem, 1.8 9, 1.5 mmol, 5 mol %) in toluene (100 mL) was degassed and purged with argon. An amber solution was obtained after the mixture was warmed to 100° C. The reaction mixture was quenched after 18 hours by the addition of 1.0 M HCl. The acidic extract was washed with ether, adjusted to pH 9 with solid sodium bicarbonate, and extracted with ethyl acetate. The organic extracts were washed with brine, dried over magnesium sulfate, filtered and concentrated under reduced pressure. The crude product (3.7 g of a brown oil) was purified by flash chromatography (silica) and eluted with 0–5% ethyl acetate-dichloromethane, which gave a clear oil (1.9 g, 53%). $^1$H NMR (DMSO-d$_6$, 300 MHz) δ 8.39 (1H, d, J=4.9 Hz), 7.33 (1H, s), 7.10 (1H, dd, J=5.0, 0.8 Hz), 6.77 (1H, dd, J=17.5, 10.8 Hz), 6.20 (1H, dd, J=17.5, 1.7 Hz), 5.44 (1H, dd, J=10.8, 1.8 Hz), 2.31 (3H, s). ESIMS m/z 120 (M+H)$^+$.

Example 27

3-[2-(4-Methyl-pyridin-2-yl)-vinyl]-nitro-1-(tetrahydro-pyran-2-yl)-1H-indazole

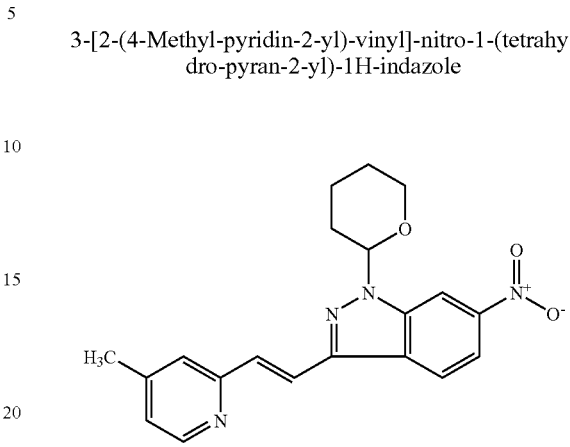

A suspension of 4-Methyl-2-vinyl-pyridine (Example 23) (1.9 g, 15.97 mmol), 6-Nitro-1-(tetrahydro-pyran-2-yl)-3-vinyl-1H-indazole (4.96 g, 13.3 mmol), Pd(OAc)$_2$ (149 mg, 0.66 mmol), P(o-tolyl)$_3$, and DIEA(3.5 ml, 19.96 mmol) in degassed DMF (50 ml) was heated under argon at 100° C. for 18 hr. The reaction mixture was cooled and the solids removed by filtration washing with EtOAc. The filtrate was diluted with EtOAc and washed with brine (2×), dried (MgSO$_4$) and concentrated under reduced pressure. The residue was chromatographed on silica gel eluting Hexanes: EtOAc (3:1) to give 3.409 (70%) of a bright yellow solid.

$^1$H NMR (CDCl$_3$) δ 8.56 (1H, s), 8.50 (1H, d, J=5.0 Hz), 8.11 (2H, m), 7.89 (1H, d, J=16.3 Hz), 7.61 (1H, s), 7.03 (1H, d, J=4.3 Hz), 5.83 (1H, dd, J=2.6, 9.0 Hz), 4.06 (1H, m), 3.82 (1H, m), 2.58 (1H, m), 2.39 (3H, s), 2.18 (2H, m), 1.78 (3H, m). Anal. Calcd for C$_{20}$H$_{20}$N$_4$O$_3$: C, 65.92; H, 5.53; N, 15.38. Found: C, 65.80; H, 5.52; N, 15.15.

Example 28

3-[2-(4-Methyl-pyridin-2-yl)-vinyl]-1-(tetrahydro-pyran-2-yl)-1H-indazol-4-ylamine

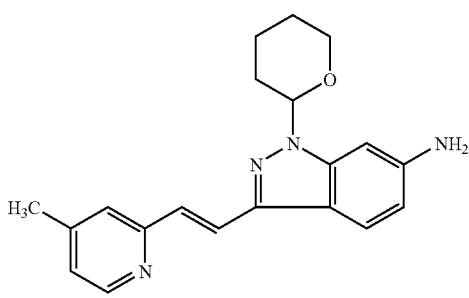

Prepared in a similar manner to that described for Example 2 except using [2-(4-Methyl-pyridin-2-yl)-vinyl]-6-nitro-1-(tetrahydro-pyran-2-yl)-1H-indazole (Example 24) instead of 3-[2-(4,6-Dimethyl-pyridin-2-yl)-vinyl]-6-nitro-1-(tetrahydro-pyran-2-yl)-1H-indazole. $^1$H NMR (DMSO-d$_6$): δ 8.43 (1H, d, J=4.8 Hz), 7.79–7.73 (2H, m), 7.50 (1H, s), 7.39 (1H, d, J=16.4 Hz), 7.09 (1H, d, J=4.8 Hz), 6.64–6.62 (2H, m), 5.57 (1H, dd, J=9.8, 2.5 Hz), 5.48 (2H, bs), 3.92–3.85 (1H, m), 3.72–3.64 (1H, m), 2.43–2.34 (1H, m), 2.33 (3H, s), 2.07–2.00 (1H, m), 1.96–1.90 (1H, m), 1.79–1.66 (1H, m), 1.60–1.53 (2H, m).

Example 29

2-[3-[2-(4-Methyl-pyridin-2-yl)-vinyl]-1-(tetrahydro-pyran-2-yl)-1H-indazol 4-ylamino]-benzoic acid methyl ester

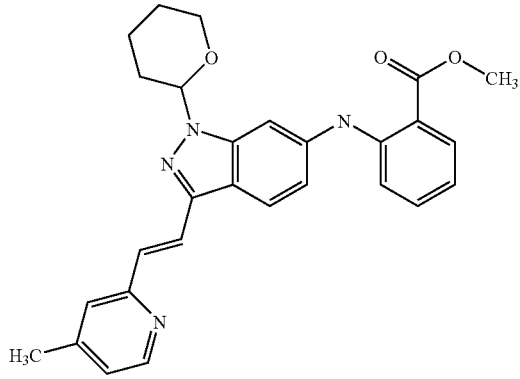

Prepared in a similar manner to that described for Example 3 except using 3-[2-(4-Methyl-pyridin-2-yl)-vinyl]-1-(tetrahydro-pyran-2-yl)-1H-indazol-6-ylamine instead of 3-[2-(4,6-dimethyl-pyridin-2-yl)-vinyl]-1-(tetrahydro-pyran-2-yl)-1H-indazol-6-ylamine. $^1$H NMR (DMSO-d$_6$): δ 9.48 (1H, s), 8.45 (1H, d, J=4.9 Hz), 8.13 (1H, d, J=8.7 Hz), 7.93 (1H, dd, J=8.3, 1.9 Hz), 7.86 (1H, d, J=16.2 Hz), 7.58 (1H, d, J=1.9 Hz), 7.54–7.44 (3H, m), 7.36 (1H, d, J=7.5 Hz), 7.18 (1H, dd, J=8.7, 1.9 Hz), 7.11 (1H, d, J=4.9 Hz), 6.87 (1H, t, J=8.3 Hz), 5.83 (1H, dd, J=9.4, 2.3 Hz), 3.87 (3H, 1H), 3.93–3.84 (1H, m), 3.77–3.69 (1H, m), 2.46–2.37 (1H, m), 2.34 (3H, s), 2.10–1.94 (2H, m), 1.81–1.53 (3H, m).

Example 30

2-[3-[2-(4-Methyl-pyridin-2-yl)-vinyl]-1-(tetrahydro-pyran-2-yl)-1H-indazol-4-ylamino]-benzoic acid

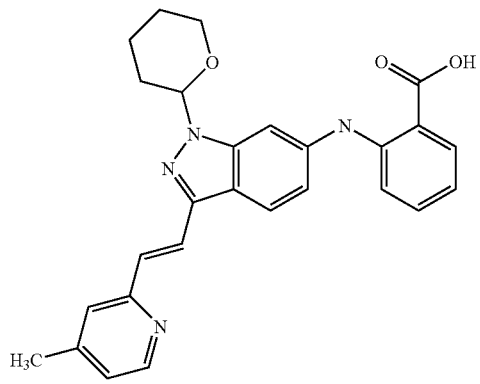

Prepared in a similar manner to that described for Example 4 above except that 2-[3-[2-(4-Methyl-pyridin-2-yl)-vinyl]-1-(tetrahydro-pyran-2-yl)-1H-indazol-6-ylamino]-benzoic acid methyl ester was used instead of 2-[3-[2-(4,6-Dimethyl-pyridin-2-yl)-vinyl]-1-(tetrahydro-pyran-2-yl)-1H-indazol-6-ylamino]-benzoic acid methyl ester (Example 3). $^1$H NMR (DMSO-d$_6$) δ 13.17 (1H, broad s), 9.83 (1H, s), 8.51 (1H, d, J=5.2 Hz), 8.14 (1H, d, J=8.7 Hz), 7.95 (1H, d, J=16.4 Hz), 7.94 (dd, 1H, J=1.5, 8.0 Hz), 7.73 (1H, s), 7.60 (1H, d, J=1.5 Hz), 7.59 (1H, s), 7.54 (1H, s), 7.46 (1H, m), 7.37 (1H, d, J=7.6 Hz), 7.23 (2H, m), 6.86 (1H, t, J=6.9 Hz), 5.87 (1H, d, J=7.6 Hz), 3.90 (1H, m), 3.76 (1H,m), 2.45 (1H,m), 2.41 (3H, s), 2.03 (2H, m), 1.77 (1H, m), 1.59 (2H, m).

Example 31

2-[3-[2-(4-Methyl-pyridin-2-yl)-vinyl]-1-(tetrahydro-pyran-2-yl)-1H-indazol-6-ylamino]-N-prop-2-ynyl-benzamide

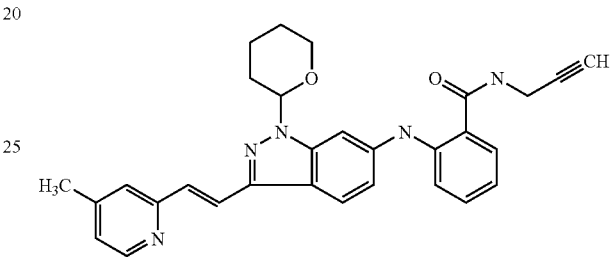

Prepared in a similar manner to that described for Example 6 above, except using propargyl amine and 2-[3-[2-(4-Methyl-pyridin-2-yl)-vinyl]-1-(tetrahydro-pyran-2-yl)-1H-indazol-6-ylamino]-benzoic acid. $^1$H NMR (DMSO-d$_6$) δ 9.87 (1H, s), 9.03 (1H, t, J=5.5 Hz), 8.46 (1H, d, J=4.9 Hz), 8.08 (1H, d, J=8.7 Hz), 7.86 (1H, d, J=16.4 Hz), 7.69 (1H, d, J=7.3 Hz), 7.53 (1H, s), 7.44 (4H, m), 7.13 (2H, m), 6.91 (1H, t, J=7.9 Hz), 5.81 (1H, dd, J=2.2, 9.6 Hz), 4.07 (2H, dd, J=2.5, 5.5 Hz), 3.89 (1H,m), 3.75 (1H, m), 3.12 (1H, t, J=2.5 Hz), 2.42 (1H, m), 2.36 (3H, s), 2.00 (2H, m), 1.75 (1H, m), 1.58 (2H, m).

Anal. Calcd for $C_{30}H_{29}N_5O_2 \cdot 0.25$ TBME: C, 73.07; H, 6.28; N, 13.64. Found: C, 72.95; H, 6.30; N, 13.64.

Example 32

2-{3-[(E)-2-(4-Methyl-pyridin-2-yl)-vinyl]-1H-indazol-6-ylamino}-N-prop-2-ynyl-benzamide

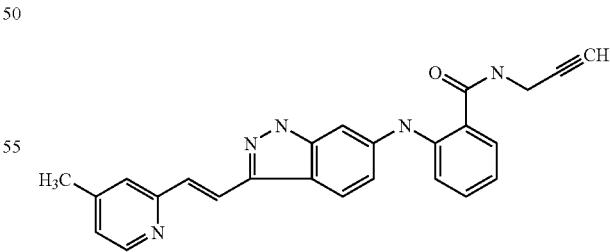

Prepared in a similar manner to that described for Example 7 except that 2-[3-[2-(4-Methyl-pyridin-2-yl)-vinyl]-1-(tetrahydro-pyran-2-yl)-1H-indazol-6-ylamino]-N-prop-2-ynyl-benzamide was used instead of N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$) δ 12.93 s), 9.79 (1H, s), 9.02 (1H, t, J=5.4 Hz), 8.45 (1H, d, J=4.9 Hz), 8.08 (1H, d, J=8.7 Hz), 7.88 (1H, d, J=16.4 Hz), 7.69 (1H, d, J=7.7 Hz), 7.45 (4H, m), 7.27 (1H, s), ), 7.10 (1H, d, J=4.9 Hz), 7.03 (1H, d, J=8.8 Hz), 6.90 (1H, t, J=7.9 Hz), 4.06 (2H, dd, J=2.4, 5.4 Hz), 3.12 (1H, t, J=2.4 Hz), 2.35 (3H, s).

Anal. Calcd for $C_{25}H_{21}N_5O \cdot 0.35\ CH_2Cl_2$: C, 69.64; H, 5.00; N, 16.02. Found: C, 69.65; H, 5.15; N, 15.80.

Example 33

N-(2-Methyl-allyl)-2-[3-[2-(4-methyl-pyridin-2-yl)-vinyl]-1-(tetrahydro-pyran-2-yl)-1H-indazol-6-ylamino]-benzamide

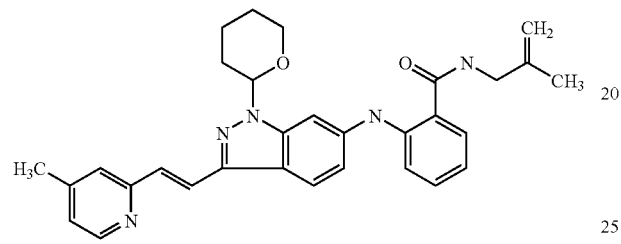

Prepared in a similar manner to that described for Example 6 above, except using 2-Methyl-allylamine and 2-[3-[2-(4-Methyl-pyridin-2-yl)-vinyl]-1-(tetrahydro-pyran-2-yl)-1H-indazol-6-ylamino]-benzoic acid. $^1$H NMR (DMSO-d$_6$) δ 9.86 (1H, s), 8.81 (1H, t, J=5.5 Hz), 8.46 (1H, d, J=4.9 Hz), 8.07 (1H, d, J=8.9 Hz), 7.86 (1H, d, J=16.4 Hz), 7.75 (1H, d, J=7.7 Hz), 7.54 (1H, s),7.50 (1H, d, J=16.4 Hz), 7.43 (3H, m), 7.11 (2H, m), 6.92 (1H, t, J=8.1 Hz), 5.81 (1H, dd, J=2.5, 9.8 Hz), 4.83 (2H, d, J=11.5 Hz), 3.81 (4H, m), 2.41 (1H, m), 2.35 (3H, s), 2.00 (2H, m), 1.76 (1H, m), 1.73 (3H, s), 1.58 (2H, m). Anal. Calcd for $C_{31}H_{33}N_5O_2 \cdot 0.80$ TBME: C, 72.71; H, 7.43; N, 12.11. Found: C, 72.43; H, 7.57; N, 12.02.

Example 34

N-(2-Methyl-allyl)-2-{[(E)-2-(4-methyl-pyridin-2-yl)-vinyl]-1H-indazol-6-ylamino}-benzamide

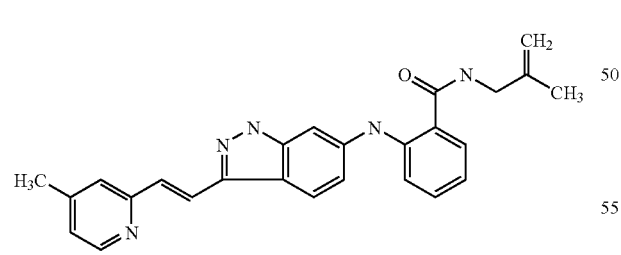

Prepared in a similar manner to that described for Example 7 except that N-(2-Methyl-allyl)-2-[3-[2-(4-methyl-pyridin-2-yl)-vinyl]-1-(tetrahydro-pyran-2-yl)-1H-indazol-6-ylamino]-benzamide was used instead of N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$) δ 12.90 (1H, s), 9.76 (1H, s), 8.80 (1H, t, J=5.5 Hz), 8.45 (1H, d, J=5.1 Hz), 8.07 (1H, d, J=8.9 Hz), 7.88 (1H, d, J=16.4 Hz), 7.75 (1H, d, J=7.9 Hz), 7.51 (1H, s), 7.48 (1H, d, J=16.4 Hz), 7.43 (2H, m), 7.24 (1H, s), 7.10 (1H, d, J=4.9 Hz), 7.00 (1H, dd, J=1.9, 8.9 Hz), 6.91 (1H, t, J=8.1 Hz), 4.82 (2H, d, J=11.3 Hz), 3.83 (2H, d, J=5.8 Hz), 2.35 (3H, s), 1.73 (3H, s).

Anal. Calcd for $C_{26}H_{25}N_5O \cdot 0.20\ H_2O$: C, 73.11; H, 5.99; N, 16.40. Found: C, 73.13; H, 6.03; N, 16.13.

Example 35

N-(3-Cyclopropyl-prop-2-ynyl)-2-[3-[2-(4-methyl-pyridin-2-yl)-vinyl]-1-(tetrahydro-pyran-2-yl)-1H-indazol-6-ylamino]-benzamide

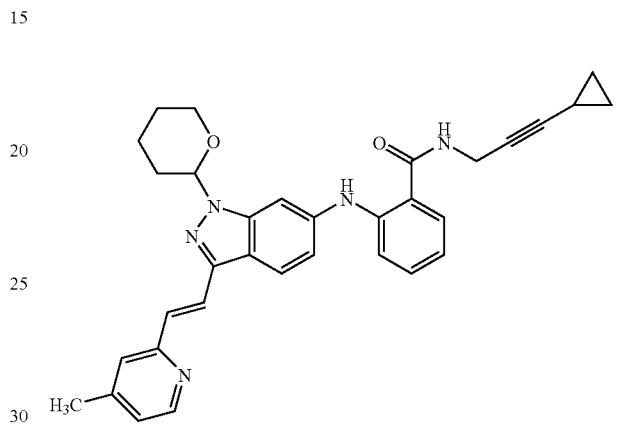

Prepared in a similar manner to that described for Example 6 above, except using 2-[3-[2-(4-methyl-pyridin-2-yl)-vinyl]-1-(tetrahydro-pyran-2-yl)-1H-indazol-6-ylamino]-benzoic acid and 3-Cyclopropyl-prop-2-ynylamine. $^1$H NMR (DMSO-d$_6$): δ 9.88 (1H, bs), 8.93 (1H, bt), 8.46 (1H, d, J=4.9 Hz), 8.08 (1H, d, J=8.7 Hz), 7.85 (1H, d, J=16.4 Hz), 7.69 (1H, d, J=7.6 Hz), 7.54–7.40 (5H, m), 7.14–7.11 (2H, m), 6.90 (1H, t, J=6.1 Hz), 5.81 (1H, d, J=7.5 Hz), 4.02 (2H, d, J=3.6 Hz), 3.95–3.85 (1H, m), 3.79–3.72 (1H, m), 2.49–2.35 (1H, m), 2.35 (3H, s), 2.15–2.01 (2H, m), 1.87–1.55 (3H, m), 1.30–1.25 (1H, m), 0.77–0.70 (2H, m), 0.59–0.54 (2H, m).

Example 36

N-(3Cycloprop-2-ynyl)-2-{3-[(E)-2-(4-methyl-pyridin-2-yl)-vinyl]-1H-indazol-6-ylamino}-benzamide

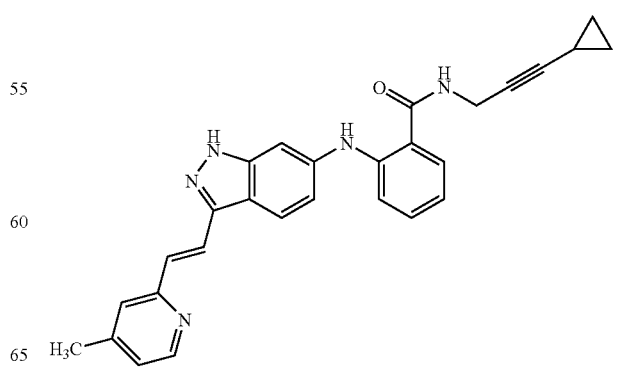

Prepared in a similar manner to that described for Example 7 above except using N-(3-cycloprop-2-ynyl)-2-[3-[2-(4-methyl-pyridin-2-yl)-vinyl]-1-(tetrahydro-pyran-2-yl)-1H-indazol-6-ylamino]-benzamide instead of N-[4-(tert-butyl-dimethyl-silanyloxy)-but-2-ynyl)-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$): δ 12.91 (1H, s), 9.79 (1H, s), 8.91 (1H, t, J=5.6 Hz), 8.44 (1H, d, J=4.9 Hz), 8.06 (1H, d, J=8.7 Hz), 7.87 (1H, d, J=16.6 Hz), 7.67 (1H, dd, J=7.9, 1.5 Hz), 7.50–7.35 (4H, m), 7.24 (1H, d, J=1.9 Hz), 7.09 (1H, d, J=4.9 Hz), 7.00 (1H, dd, J=8.7,1.5 Hz), 6.88 (1H, dt, J=4.1, 1.5 Hz), 4.00 (2H, dd, J=5.3, 1.9 Hz), 2.34 (3H, s), 1.31–1.23 (1H, m), 0.75–0.69 (2H, m), 0.56–0.52 (2H, m).

Example 37

2-{3-[2-(4-Methyl-pyridin-2-yl)-vinyl]-1H-indazol6-ylamino}-N-pyridin-2-ylmethyl-benzamide

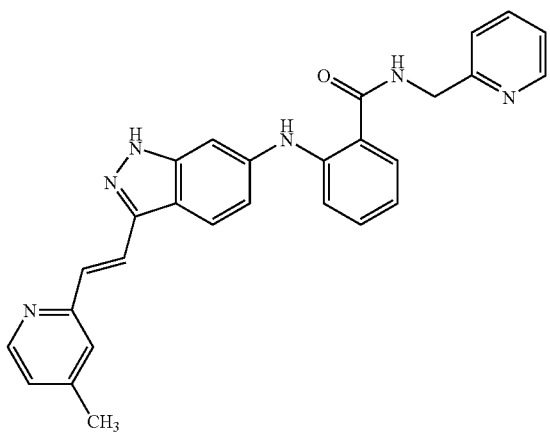

Prepared in a similar manner to that described for Example 6 and Example 7 above using 2-[3-[2-(4-methyl-pyridin-2-yl)-vinyl]-1-(tetrahydro-pyran-2-yl)-1H-indazol -6-ylamino]-benzoic acid and C-Pyridin-2-yl-methylamine. $^1$H NMR (DMSO-d$_6$, 300 MHz) δ 12.91 (1H, s), 9.77 (1H, s), 9.19 (1H, t, J=5.8 Hz), 8.50 (1H, d, J=4.1 Hz), 8.45 (1H, d, J=5.0 Hz), 8.06 (1H, d, J=8.8 Hz), 7.88 (1H, d, J=16.4 Hz), 7.82–7.70 (2H, m), 7.51–7.25 (7H, m), 7.10 (1H, d, J=4.6 Hz), 6.98 (1H, dd, J=8.8, 1.8 Hz), 6.96–6.91 (1H, m), 4.58 (2H, d, J=5.9 Hz), 2.35 (3H, s). ESIMS m/z 461 (M+H)$^+$. Anal. Calcd. for C$_{28}$H$_{24}$N$_6$O×0.3 MTBE: C, 72.71; H, 5.77; N, 17.25. Found: C, 72.38; H, 5.80; N, 16.88.

Example 38

2-{3-[2-(4-Methyl-pyridin-2-yl)-vinyl]-1H-indazol6-ylamino}-N-pyridin-4-ylmethyl-benzamide

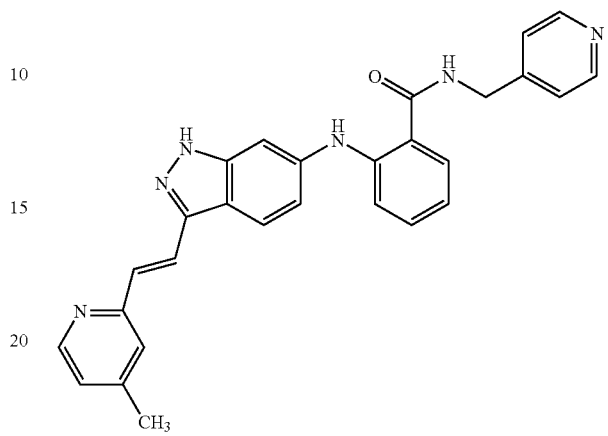

Prepared in a similar manner to that described for Examples 6 and 7 above except using 2-[3-[2-(4-methyl-pyridin-2-yl)-vinyl]-1-(tetrahydro-pyran-2-yl)-1H-indazol-6-ylamino]-benzoic acid and C-Pyridin-4-yl-methylamine.
$^1$H NMR (DMSO-d$_6$, 300 MHz) δ 12.90 (1H, s), 9.73 (1H, s), 9.21 (1H, t, J=5.9 Hz), 8.49–8.44 (3H, m), 8.06 (1H, d, J=8.7 Hz), 7.88 (1H, d, J=16.4 Hz), 7.81 (1H, d, J=7.5 Hz), 7.51–7.40 (4H, m), 7.31 (2H, d, J=5.9 Hz), 7.24 (1H, s), 7.11 (1H, d, J=4.4 Hz), 7.00 (1H, dd, J=8.7, 1.7 Hz), 6.97–6.92 (1H, m), 4.50 (2H, d, J=5.9 Hz), 2.35 (3H, s). ESIMS m/z 461 (M+H)$^+$.
Anal. Calcd. for C$_{28}$H$_{24}$N$_6$O×0.4 H$_2$O×0.7 MTBE: C, 71.36; H, 6.45; N, 15.85. Found: C, 71.27; H, 6.29; N, 15.53.

Example 39

N-(6-Methyl-pyridin-2-ylmethyl)-2-{3-[2-(4-methyl-pyridin-2-yl)-vinyl]-1H-indazol-6-ylamino}-benzamide

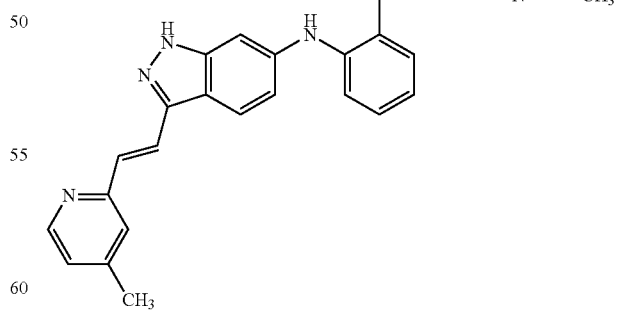

Prepared in a similar manner to that described for Examples 6 and 7 above except using 2-[3-[2-(4-methyl-pyridin-2-yl)-vinyl]-1-(tetrahydro-pyran-2-yl)-1H-indazol-6-ylamino]-benzoic acid and C-(6-Methyl-pyridin-2-yl)-methylamine.

¹H NMR (DMSO-d₆, 300 MHz) δ 12.92 (1H, s), 9.76 (1H, s), 9.20 (1H, t, J=5.8 Hz), 8.44 (1H, d, J=4.9 Hz), 8.05 (1H, d, J=8.6 Hz), 7.86 (1H, d, J=16.4 Hz), 7.81 (1H, d, J=7.7 Hz), 7.59 (1H, t, J=7.7 Hz), 7.49–7.37 (4H, m), 7.23 (1H, s), 7.11–7.08 (3H, m), 6.99 (1H, dd, J=8.7, 1.6 Hz), 6.95–6.90 (1H, m), 4.51 (2H, d, J=5.9 Hz), 2.42 (3H, s), 2.33 (3H, s). ESIMS m/z 475 (M+H)⁺. Anal. Calcd. for C₂₉H₂₆N₆O×0.4 DCM: C, 68.98; H, 5.29; N, 16.39. Found: C, 68.84; H, 5.42; N, 16.20.

Example 40

N-2,6-Dimethyl-2H-pyrazol-3-ylmethyl)-2-[(E)-3-[2-(4-methyl-pyridin-2-yl)-vinyl]-1-(tetrahydro-pyran-2-yl)-1H-indazol6-ylamino]-benzamide

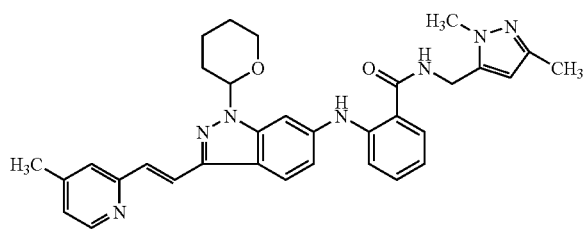

Prepared in a similar manner to that described for Example 6 above, except using 2-{3-[2-(4-methyl-pyridin-2-yl-vinyl)-1-(tetrahydro-pyran-2-yl)-1H-indazol-6-ylamino]-benzoic acid and C-(2,5-Dimethyl-2H-pyrazol-3-yl)-methylamine. ¹H NMR (DMSO-d₆) δ 9.81(1H, s), 9.05 (1H, bt), 8.46 8.7 Hz), 7.85 (1H, d, J=16.4 Hz), 7.71 (1H, d, J=7.5 Hz), 7.54–7.40 (5H, m), 7.11–7.09 (2H, m), 6.91 (1H, t, J=6.9 Hz), 5.94 (1H, s), 5.80 (1H, d, J=7.3 Hz), 4.45 (2H, d, J=5.5 Hz), 3.93–3.85 (1H, m), 3.78–3.69 (1H, m), 3.73 (3H,s), 2.45–2.35 (1H, m), 2.35 (3H, s), 2.07 (3H, s), 2.06–1.95 (2H, m), 1.85–1.53 (m, 3H).

Example 41

N-(2,5-Dimethyl-2H-pyrazol-3-ylmethyl)-2-{3-[(E)-2-(4-methyl-pyridin-2-yl)-vinyl]-1H-indazol-6-ylamino}-benzamide

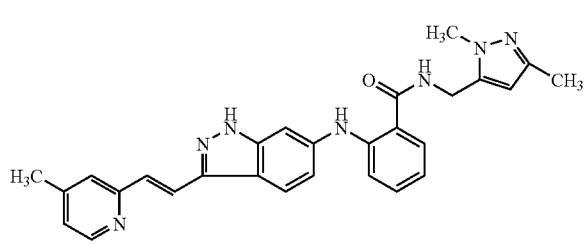

Prepared in a similar manner to that described for Example 7 except using N-(2,5-Dimethyl-2H-pyrazol-3-ylmethyl)-2-[(E)-3-[2-(4-methyl-pyridin-2-yl)-vinyl]-1-(tetrahydro-pyran-2-yl)-1H-indazol-6-ylamino]-benzamide instead of N-[4-(tert-butyl-dimethyl-silanyloxy)-but-2-ynyl)-2-[3-[2-(4,6-dimethyl-pyridin-2-yl)-vinyl]-1-(tetrahydro-pyran-2-yl)-1H-indazol-6-ylamino]-benzamide. ¹H NMR (DMSO-d₆) δ 12.90 (1H, s), 9.70 (1H, s), 9.03 (1H, t, J=6.0 Hz), 8.44 (1H, d, J=4.9 Hz), 8.06 (1H, d, J=9.0 Hz), 7.87 (1H, d, J=16.2 Hz), 7.70 (1H, d, J=7.5 Hz), 7.50–7.38 (4H, m), 7.22 (1H, s), 7.1 (1H, d, J=5.6 Hz), 6.99 (1H, dd, J=8.7, 1.5 Hz), 6.90 (1H, dt, J=7.9, 1.9 Hz), 5.91 (1H, s), 4.43 (2H, d, J=5.6 Hz), 3.72 (3H, s), 2.34 (3H, s), 2.05 (3H, s).

Example 42

1-Methyl-1H-benzoimidazole-2-carbaldehyde oxime

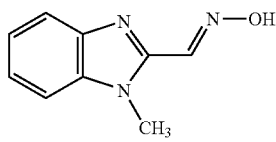

To a stirred suspension of 1-Methyl-1H-benzoimidazole-2-carbaldehyde (980 mg, 6.61 mmol) in H₂O (10 ml) was added a solution of Sodium Acetate (3.25 g, 39.68 mmol) and Hydroxylamine hydrochloride (1.38 g, 19.84 mmol) in 10 ml of H₂O. The reaction was stirred at rt for 2 hr and the thick precipitate was collected by filtration, washed with water and dried under vacuum to give 1.02 g (94%) of a white solid. ¹H NMR (DMSO-d₆) δ 12.06 (1H, s), 8.28 (1H, s), 7.65 (1H, d, J=7.5 Hz), 7.60 (1H, d, J=6.8 Hz), 7.32 (1H, t, J=7.2 Hz), 7.23 (1H, t, J=6.8 Hz), 4.00 (3H, s).
Anal. Calcd for C₉H₉N₃O: C, 61.70; H, 5.18; N, 23.99. Found: C, 61.80; H, 5.23; N, 23.98.

Example 43

C-(1-Methyl-1H-benzoimidazol-2-yl)-methylamine dihydrochloride

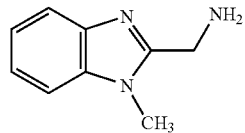

A Parr pressure bottle was charged with 1-Methyl-1H-benzoimidazole-2-carbaldehyde oxime (267 mg, 1.6 mmol), 10% Palladium on Carbon (75 mg), concentrated HCl (2 drops) and EtOH (25 ml). The reaction mixture was shaken under 45 psi H₂ for 2 hr before the catalyst was removed by filtration. The filtrate was concentrated under reduced pressure and the residue was triturated with Et₂O to give 340 mg (90%) of a white solid as the dihydrochloride salt and was used without further purification. ¹H NMR (DMSO-d₆): δ 8.87 (2H, broad s), 7.72 (2H, m), 7.38 (2H, m), 4.50 (2H, s), 3.89 (3H, s).

Example 44

N-(1-Methyl-1H-benzoimidazol-2-ylmethyl)-2-[3-[2-(4-methyl-pyridin-2-yl)-vinyl]-1-(tetrahydro-pyran-2-yl)-1H-indazol-6-ylamino]-benzamide

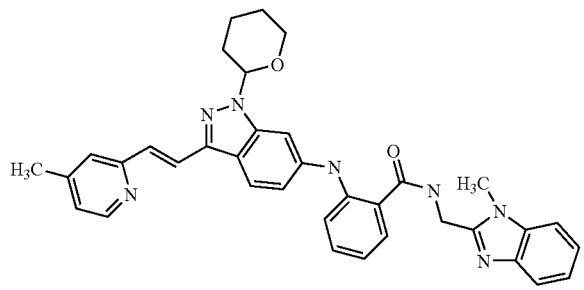

Prepared in a similar manner to that described for Example 6 above, except using C-(1-Methyl-1H-benzoimidazol-2-yl)-methylamine hydrochloride N and 2-[3-[2-(4-Methyl-pyridin-2-yl)-vinyl]-1-(tetrahydro-pyran-2-yl)-1H-indazol-6-ylamino]-benzoic acid. $^1$H NMR (DMSO-d$_6$) δ 9.82 (1H, s), 9.20 (1H, t, J=5.3 Hz), 8.46 (1H, d, J=4.9 Hz), 8.07 (1H, d, J=8.9 Hz), 7.85 (1H, d, J=16.4 Hz), 7.74 (1H, d, J=7.3 Hz), 7.58 (1H, d, J=7.2 Hz), 7.50 (6H, m), 7.19 (4H, m), 6.92 (1H, t, J=8.1 Hz), 5.78 (1H, dd, J=2.5, 9.5 Hz), 4.79 (2H, d, J=5.5 Hz), 3.89 (1H,m), 3.83 (3H, s), 3.71 (1H, m), 2.41 (1H, m), 2.35 (3H, s), 2.00 (2H, m), 1.74 (1H, m), 1.57 (2H, m).

Anal. Calcd for C$_{36}$H$_{35}$N$_7$O$_2$.0.65 Hexanes: C, 73.31; H, 6.80; N, 15.00. Found: C, 72.92; H, 6.90; N, 14.71.

Example 45

N-(1-Methyl-1H-benzoimidazol-2-ylmethyl)-2-{3-[(E)2-(4-methyl-pyridin-2-yl)-vinyl]-1H-indazol-6-ylamino}-benzamide

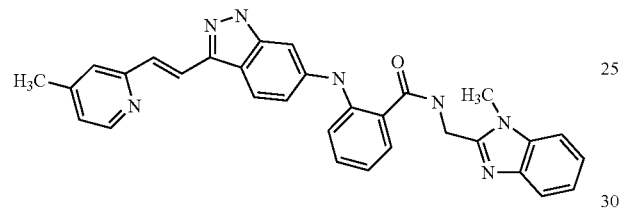

Prepared in a similar manner to that described for Example 7 except that N-(1-Methyl-1H-benzoimidazol-2-ylmethyl)-2-[3-[2-(4-methyl-pyridin-2-yl)-vinyl]-1-(tetrahydro-pyran-2-yl)-1H-indazol-6-ylamino]-benzamide was used instead of N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO-d$_6$) δ 12.93 (1H, s), 9.73 (1H, s), 9.19 (1H, t, J=5.3 Hz), 8.45 (1H, d, J=4.9 Hz), 8.06 (1H, d, J=8.5 Hz), 7.88 (1H, d, J=16.4 Hz), 7.74 (1H, d, J=7.9 Hz), 7.60–7.36 (6H, m), 7.29–7.14 (3H, m), 7.10 (1H, d, J=4.7 Hz), 7.04 (1H, dd, J=1.8, 8.9 Hz), 6.91 (1H, t, J=7.3 Hz), 4.79 (2H, d, J=5.3 Hz), 3.83 (3H, s), 2.35 (3H, s).

Anal. Calcd for C$_{31}$H$_{27}$N$_7$O. 1.80H$_2$O. 0.40CH$_2$Cl$_2$: C, 65.02; H, 5.46; N, 16.91. Found: C, 64.97; H, 5.82; N, 17.09.

Example 46

1-Methyl-1H-imidazole-2-carbaldehyde oxime

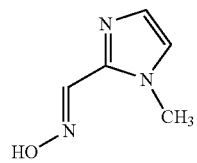

Prepared in a similar manner to that described for Example 39 except that 1-Methyl-1H-imidazole-2-carbaldehyde was used instead of 1-Methyl-1H-benzoimidazole-2-carbaldehyde.

$^1$H NMR (DMSO-d$_6$): δ 11.50 (1H, s), 8.05 (1H, s), 7.28 (1H, s), 6.95 (1H, s), 3.80 (3H, s). Anal. Calcd for C$_5$H$_7$N$_3$O: C, 47.99; H, 5.64; N, 33.58. Found: C, 48.22; H, 5.58; N, 33.45.

Example 47

C-(1-Methyl-1H-imidazol-2-yl)-methylamine dihydrochloride

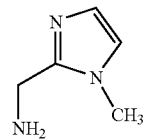

Prepared in a similar manner to that described for Example 40 except that 1-Methyl-1H-imidazole-2-carbaldehyde oxime was used instead of 1-Methyl-1H-benzoimidazole-2-carbaldehyde oxime. $^1$H NMR (DMSO-d$_6$): δ 7.45 (1H, s), 7.29 (1H, s), 4.25 (21H, s), 3.79 (3H, s).

Example 48

N-(1-Methyl-1H-imidazol-2-ylmethyl)-2-[3-[2-(4-methyl-pyridin-2-yl)-vinyl]-1-(tetrahydro-pyran-2-yl)-1H-indazol-6-ylamino]-benzamide

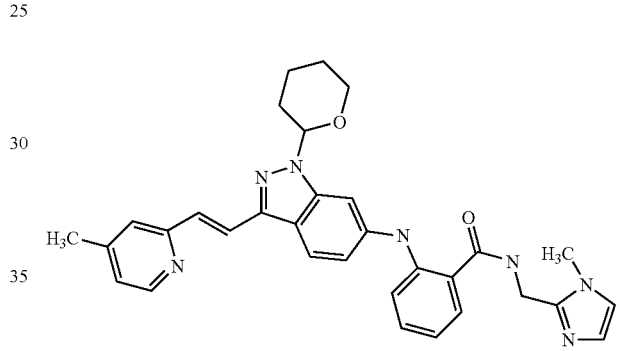

Prepared in a similar manner to that described for Example 6 above except using C-(1-Methyl-1H-imidazol-2-yl)-methylamine hydrochloride and 2-[3-[2-(4-Methyl-pyridin-2-yl) -vinyl]-1-(tetrahydro-pyran-2-yl)-1H-indazol-6-ylamino]-benzoic acid. $^1$H NMR (DMSO-d$_6$) δ 9.83 (1H, s 9.03 (1H, t, J=5.5 Hz), 8.45 (1H, d, J=4.7 Hz), 8.09 (1H, d, J=8.5 Hz), 7.85 (1H, d , J=16.5 Hz), 8.67 (1H, d , J=7.3 Hz), 7.53–7.39 (4H, m), 7.11 (3H, m), 6.90 (1H, d, J=6.9 Hz), 6.86 (1H, s), 5.79 (1H, d , J=8.9 Hz), 5.75 (1H, s), 4.54 (1H, d , J=5.5 Hz), 3.85–3.70 (2H, m), 3.66 (3H, s), 2.35 (3H, s), 2.10 (2H, m), 1.70 (2H, m), 1.60 (3H, m). Anal. Calcd for C$_{32}$H$_{33}$N$_7$O$_2$.0.8 CH$_2$Cl$_2$: C, 63.99; H, 5.672; N, 15.93. Found: C, 63.95; H, 5.72; N, 16.01.

Example 49

N-(1-Methyl-1H-imidazol-2-ylmethyl)-2-{3-[2-(4-methyl-pyridin-2-yl)-vinyl]-1H-indazol-6-ylamino}-benzamide

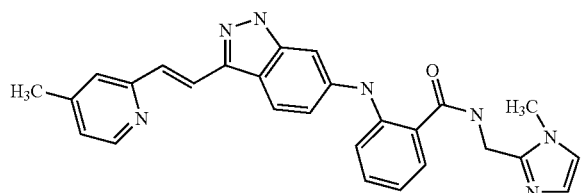

Prepared in a similar manner to that described for Example 7 except that N-(1-Methyl-1H-imidazol-2-ylmethyl)-2-[3-[2-(4-methyl-pyridin-2-yl)-vinyl]-1-(tetrahydro-pyran-2-yl)-1H-indazol-6-ylamino]-benzamide was used instead of N-[4-(tert-Butyl-dimethyl-silanyloxy)-but-2-ynyl]-2-[3-[2-(4,6-dimethyl-pyridin-2-yl)-vinyl]-1-(tetrahydro-pyran-2-yl)- 1H-indazol-6-ylamino]-benzamide. $^1$H NMR (DMSO-d$_6$) δ 12.89 (1H, s 9.72 (1H, s 8.99 (1H, t, J=5.6 Hz), 8.44 (1H, d, J=4.9 Hz), 8.05 (1H, d, J=8.7 H), 7.86 (1H, d , J=16.4 Hz), 7.66 (1H, d , J=6.7 Hz), 7.49–7.36 (4H, m), 7.24 (1H, m), 7.09 (2H, d, J=8.1 Hz), 7.02 (1H, d, J=8.8 Hz), 6.88 (1H, t, J=6.9 Hz), 6.81 (1H, s), 4.52 (2H, d , J=5.5 Hz), 3.29 (3H, s), 2.34 (3H, s). Anal. Calcd for C$_{27}$H$_{25}$N$_7$O. 0.35CH$_2$Cl$_2$: C, 66.59; H, 5.25; N, 19.88. Found: C, 66.48; H, 5.65; N, 19.56.

Example 50

N-(4-Hydroxy-but-2-ynyl)-2-[3-[2-(4-methyl-pyridin-2-yl)-vinyl]-1-(tetrahydro-pyran-2-yl)-1H-indazol-6-ylamino]-benzamide

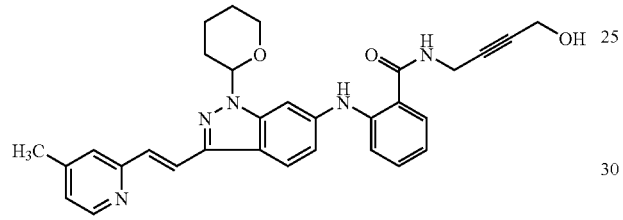

Prepared in a similar manner to that described for Example 6 except using 2-[3-[2-(4-methyl-pyridin-2-yl)-vinyl]-1-(tetrahydro-pyran-2-yl)-1H-indazol-6-ylamino]-benzoic acid and 4-(tert-Butyl-dimethyl -silanyloxy)-but-2-ynylamine. $^1$H NMR (CDCl$_3$): δ 9.48 (H, s), 8.46 (1H, d, J=5.3 Hz), 7.92 (1H, d, J=9.0 Hz), 7.83 (1H, d, J=16.2 Hz), 7.52 (1H, d, J=16.6 Hz), 7.46–7.41 (2H, m), 7.34–7.31 (3H, m), 7.12 (1H, dd, J=8.7, 1.9 Hz), 6.99 (1H, d, J=4.9 Hz), 6.81 (1H, t, J=6.8 Hz), 6.40 (1H, t, J=4.9 Hz), 5.62 (1H, dd, J=9.4, 3.0 Hz), 4.28–4.23 (4H, m), 4.08–4.01 (1H, m), 3.76–3.67 (1H, m), 2.63–2.49 (1H, m), 2.38 (3H, s), 2.22–2.06 (2H, m), 1.80–1.60 (3H, m).

Example 51

2-{3-[(E)-2-(4-Methyl-pyridin-2-yl)-vinyl]-1H-indazol6-ylamino}-N-(4-hydroxy-but-2-ynyl)-benzamide

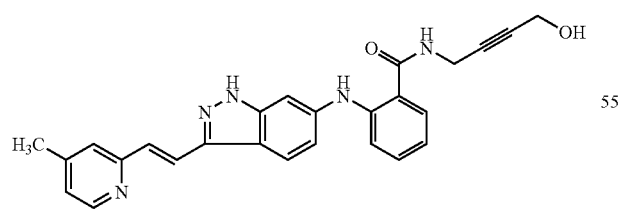

Prepared in a similar manner to that described for Example 7 except using a mixture of N-(4-Hydroxy-but-2-ynyl)-2-[3-[2-(4-methyl-pyridin-2-yl)-vinyl]-1-(tetrahydro-pyran-2-yl)-1H-indazol-6-ylamino]-benzamide and N-[4-(tert-butyl-dimethyl-silanyloxy)-but-2-ynyl]-2-[3-[2-(4-methyl-pyridin-2-yl)-vinyl]-1-(tetrahydro-pyran-2-yl)-1H-indazol-6-ylamino]-benzamide instead of N-[4-(tert-butyl-dimethyl-silanyloxy)-but-2-ynyl)-2-[3-[2-(4,6-dimethyl-pyridin-2-yl)-vinyl]-1-(tetrahydro-pyran-2-yl)-1H-indazol-6-ylamino]-benzamide. $^1$H NMR (DMSO -d$_6$): δ 12.92 (1H, s), 9.83 (1H, s), 9.00 (1H, t, J=5.3 Hz), 8.44 (1H, d, J=4.9 Hz), 8.06 (1H, d, J=9.0 Hz), 7.87 (1H, d, J=16.6 Hz), 7.68 (1H, d, J=7.9 Hz), 7.50–7.38 (4H, m), 7.26 (1H, s), 7.09 (1H, d, J=5.3 Hz), 7.01 (1H, dd, J=8.7, 1.5 Hz), 6.88 (1H,dt, J=6.8, 1.5 Hz), 5.11 (1H, t, J=3.0 Hz), 4.10–4.04 (4H, m), 2.34 (3H, s).

Example 52

2-[3-(Pyrrol-1-yliminomethyl)-1-(2-trimethylsilanyl-thoxymethyl)-1H-indazol4-ylamino]-benzoic acid methyl ester

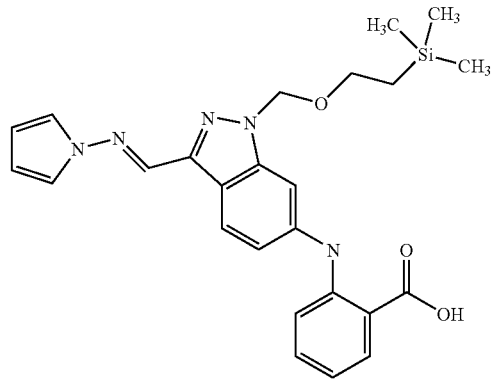

Prepared in a similar manner to that described for Examples 2 and 3 above except starting with 6-Nitro-3-styryl-1-(2-trimethylsilanyl-ethoxymethyl)-1H-indazole instead of 6-Iodo-3-styryl-1-(2-trimethylsilanyl-ethoxymethyl)-1H-indazole.

This material was taken on as a crude mixture of product and 2-Amino-benzoic acid methyl ester in the next step.

Example 53

2-[3-(Pyrrol-1-yliminomethyl)-1-(2-trimethylsilanyl-ethoxymethyl)-1H-indazol6-ylamino]-benzoic acid

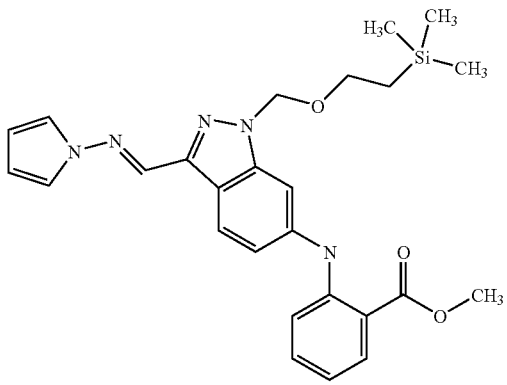

Isolated as a byproduct from reaction of N-[4-(tert-Butyl-dimethyl-silanyloxy)-but-2-ynyl]-2-[3-(pyrrol-1-yliminomethyl)-1-(2-trimethylsilanyl-ethoxymethyl)-1H-indazol-6-ylamino]-benzamide and TBAF using a procedure similar to Example 11 in U.S. Pat. No. 6,534,524, issued Mar. 18, 2003, hereby incorporated in its entirety for all purposes. ¹H NMR (DMSO-d₆) δ 13.19 (1H, broad s 10.00 (1H, s,9.13 (1H, s),8.37 (1H, d, J=8.7 Hz), 8.06 (1H, d, J=7.5 Hz), 7.75 (1H, s), 7.64 (2H, t, J=2.3 Hz), 7.54 (2 H, m), 7.35 (1H, dd, J=1.9, 8.7 Hz), 6.99 (1H, m), 6.33 (2H, t, J=2.3 Hz), 5.89 (2H, s), 3.68 (2H, t, J=8.1 Hz), 0.94 (2H, t, J=8.1 Hz), 0.00 (9H, s).

Example 54

N-(3-Cyclopropyl-prop-2-ynyl)-2-[3-(pyrrol- -ylimi-nomethyl)-1-(2-trimethylsilanyl-ethoxymethyl)-1H-indazol-6-ylamino]-benzamide

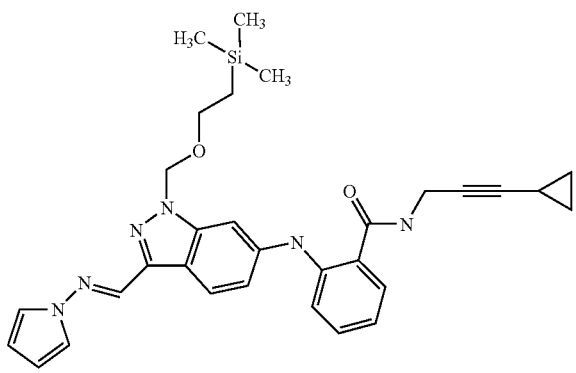

Prepared in a similar manner to that described for Example 6 above, except using 2-[3-(Pyrrol-1-yliminom-ethyl)-1-(2-trimethylsilanyl-ethoxymethyl)-1H-indazol-6-ylamino]-benzoic acid and 3-Cyclopropyl-prop-2-yny-lamine. ¹H NMR (DMSO-d₆) δ 9.93 (1H, s 8.99 (1H,s), 8.95 (1H, d, J=5.6 Hz), 8.20 (1H, d, J=8.9 Hz), 7.68 (1H, d, J=8.1 Hz), 7.51 (4H, m), 7.37 (1H, t , J=6.8 Hz), 7.14 (1H, d, J=9.0 Hz), 6.91 (1 H, t, J=7.5 Hz), 6.21 (2H, t, J=2.3 Hz), 5.74 (2H, s), 4.00 (2H, dd, J=2.0, 5.6 Hz), 3.55 (2H, t, J=7.9 Hz), 1.26 (1H, m), 0.82 (2H, t, J=7.9 Hz), 0.72 (2H, m) 0.54 (2H, m), −0.12 (9H, s).

Example 55

N-(3-Cyclopropyl-prop-2-ynyl)-2-[3-(pyrrol-1-yliminomethyl)-1H-indazol-6-ylamino]-benzamide

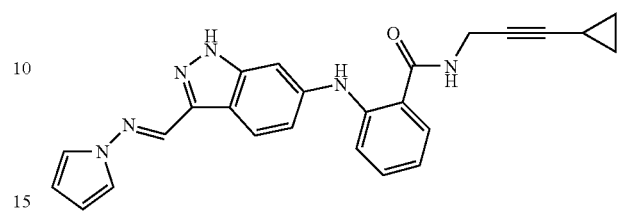

Prepared in a similar manner to that described for Example 11 in U.S. Pat. No. 6,534,524, issued Mar. 18, 2003, herein incorporated by reference in its entirety for all purposes, except that N-(3-Cyclopropyl-prop-2-ynyl)-2-[3-(pyrrol-1-yliminomethyl)-1-(2-trimethylsilanyl-ethoxym-ethyl)-1H-indazol-6-ylamino]-benzamide was used instead of N-methyl-N-{3-styryl-1-[2-trimethyl-silanyl)-ethoxym-ethyl]-1H-indazol-6-yl}-benzene-1,3-diamine. ¹H NMR (DMSO-d₆) δ 13.29 (1H, s), 9.83 (1H, s 8.98 (1H, s), 8.95 (1H, t, J=5.5 Hz), 8.19 (1H, d, J=8.9 Hz), 7.68 (1H, d, J=7.5 Hz), 7.52 (2H, t, J=2.3 Hz), 7.43 (2H, m), 7.29 (1H, s), 7.07 (1H, dd, J=1.9, 8.7 Hz), 6.91 (1H, t, J=7.4 Hz), 6.21 (2H, t, J=2.3 Hz), 4.01 (2H, dd, J=1.7, 5.5 Hz), 1.27 (1H, m), 0.73 (2H, m), 0.55 (2H, m). Anal. Calcd for C₂₅H₂₂N₆O. 0.05Hexanes. 0.30 H₂O: C, 70.31; H, 5.43; N, 19.45. Found: C, 70.63; H, 5.38; N, 19.18.

Example 56

N-[4-(tert-Butyl-dimethyl-silanyloxy)-but-2-ynyl]-2-[3-(pyrrol-1-yliminomethyl)-1-(2-trimethylsilanyl-ethoxymethyl)-1H-indazol-6-ylamino]-benzamide

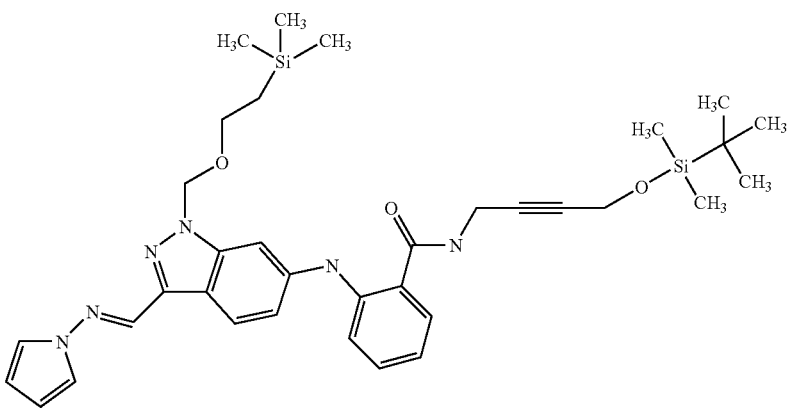

Example 57

N-(4-Hydroxy-but-2-ynyl)-2-[3-(pyrrol-1-yliminomethyl)-1H-indazol-6-ylamino]-benzamide

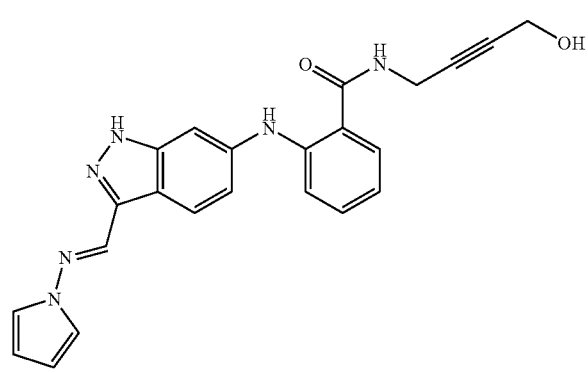

Prepared in a similar manner to that described for Example 6 above except using 2-[3-(Pyrrol-1-yliminomethyl)-1-(2-trimethylsilanyl-ethoxymethyl)-1H-indazol-6-ylamino]-benzoic acid and 4-(tert-Butyl-dimethyl-silanyloxy)-but-2-ynylamine. $^1$H NMR (DMSO-$d_6$) δ 10.04 (1H, s 9.16 (1H, t, J=5.3 Hz), 9.10 (1H,s), 8.31 (1H, d, J=8.7 Hz), 7.78 (1H, d, J=7.9 Hz), 7.67 (4H, m), 7.49 (1H, t, J=8.5 Hz), 7.24 (1H, dd, J=1.7, 8.7 Hz), 7.03 (1H, t, J=7.4 Hz), 6.33 (2H, t, J=2.3 Hz), 5.85 (2H, s), 4.83 (2H, s), 4.19 (2H, d, J=5.5 Hz), 3.66 (2H, t, J=7.9 Hz), 0.94 (2H, m), 0.89 (9H, s), 0.13 (6H, s), 0.00 (9H, s).

Prepared in a similar manner to that described for Example 11, in U.S. Pat. No. 6,534,524, issued Mar. 18, 2003, herein incorporated by reference in its entirety for all purposes, except that N-[4-(tert-Butyl-dimethyl-silanyloxy)-but-2-ynyl]-2-[3-(pyrrol-1-yliminomethyl)-1-(2-trimethylsilanyl-ethoxymethyl)-1H-indazol-6-ylamino]-benzamide was used instead of N-methyl-N-{3-styryl-1-[2-trimethyl-silanyl)-ethoxymethyl]-1H-indazol-6-yl}-benzene-1,3-diamine. $^1$H NMR (DMSO-$d_6$) δ 13.30 (1H, s), 9.87 (1H, .s 9.04 (1H, t, J=5.3 Hz), 8.99 (1H, s), 8.19 (1H, d, J=8.5 Hz), 7.70 (1H, d, J=7.3 Hz), 7.46 (4H, m), 7.31 (1H, s), 7.08 (1H, dd, J=1.7, 8.7 Hz), 6.91 (1H, t, J=7.3 Hz), 6.21 (2H, t, J=2.1 Hz), 5.14 (1H, t, J=5.8 Hz), 4.10 (2H, d, J=5.5 Hz), 4.06 (2H, d, J=5.8 Hz). Anal. Calcd for $C_{23}H_{20}N_6O_2$·0.35Hexanes·0.20 H$_2$O: C, 67.45; H, 5.86; N, 18.81. Found: C, 67.70; H, 5.73; N, 18.56.

Example 58

2,5-Dimethyl-2H-pyrazole-3-carbonitrile

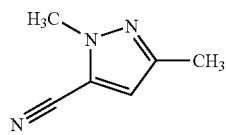

2,5-Dimethyl-2H-pyrazole-3-carbonitrile was prepared from ethyl 1,3-dimethylpyrazole-5-carboxiate according to procedures published for 1-methyl-pyrazol-5-carbonitrile by Castellanos, Maria and Montserrat, Llinas; JCS Perkins Trans I(1985) 1209–1215. $^1$H NMR (CDCl$_3$) δ 6.52 (1H, s), 3.96 (3H, s), 2.27 (3H, s).

Example 59

C-(2,5-Dimethyl-2H-pyrazol-3-yl)-methylamine

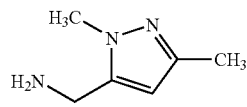

A suspension of 2,5-Dimethyl-2H-pyrazole-3-carbonitrile (654 mg, 5.4 mmol) and 10% palladium on carbon (200 mg) in ethanol (15 mL) was shaken in a Parr hydrogenation apparatus under 45 psi H$_2$ for 17 hr. The mixture was filtered through celite and the filtrate was concentrated under reduced pressure to give 608 mg of an oil which was used without any further purification. $^1$H NMR (CDCl$_3$) δ 5.91 (1H, s), 3.81, 3.73 (2H,2s), 3.75 (3H, s), 2.21 (3H, s).

Example 60

N-(2,5-Dimethyl-2H-pyrazol-3-ylmethyl)-2-[3-(pyrrol-1-yliminomethyl)-1-(2-trimethylsilanyl-ethoxymethyl)-1H-indazol-6-ylamino]-benzamide

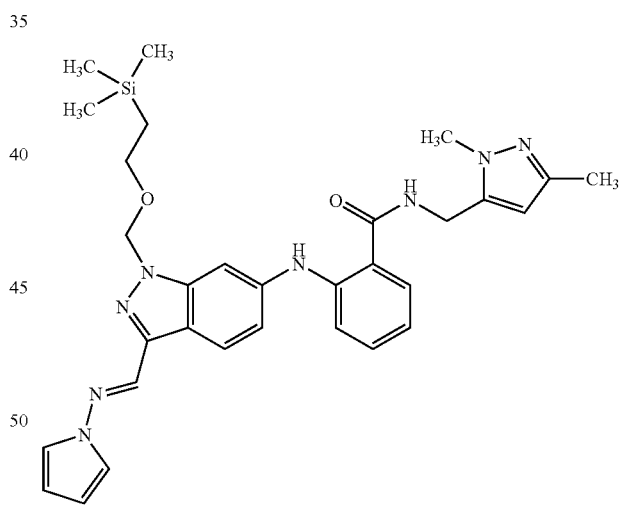

Prepared in a similar manner to that described for Example 6 above except using 2-[3-(Pyrrol-1-yliminomethyl)-1-(2-trimethylsilanyl-ethoxymethyl)-1H-indazol-6-ylamino]-benzoic acid and C-(2,5-Dimethyl-2H-pyrazol-3-yl)-methylamine. $^1$H NMR (CDCl$_3$) δ 9.56 (1H, s), 8.68 (1H, s), 8.30 (1H, d, J=8.7 Hz), 7.49 (1H, d, J=8.3 Hz), 7.43 (1H, dd, J=7.9, 1.5 Hz), 7.36–7.31 (2H, m), 7.23 (2H, t, J=2.6 Hz), 7.17 (1H, dd, J=8.7, 1.9 Hz), 6.83 (1H, t, J=7.2 Hz), 6.32 (1H, bt), 6.29 (2H, t, J=2.3 Hz), 6.01 (1H, s), 5.67 (2H, s), 4.61 (2H, d, J=5.6 Hz), 3.60 (3H, s), 3.58 (2H, t, J=8.3 Hz), 2.22 (3H, s), 0.90 (2H, t, J=8.7 Hz), 0.06 (9H, s).

Example 61

N-(2,5-Dimethyl-2H-pyrazol-3-ylmethyl)-2-[3-(pyrrol-1-yliminomethyl)-1H-indazol-6-ylamino]-benzamide

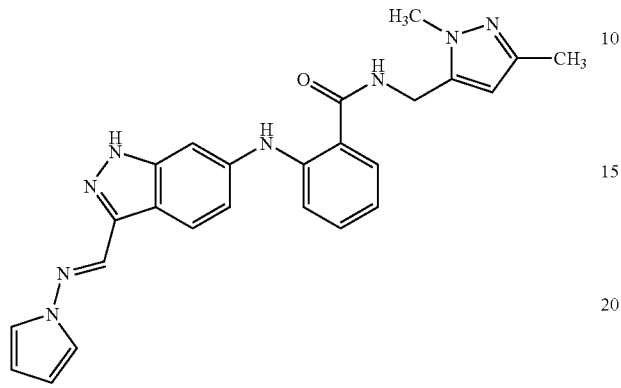

Prepared in a similar manner to that described for Example 11 in U.S. Pat. No. 6,534,524, issued Mar. 18, 2003, herein incorporated by reference in its entirety for all purposes, except that N-(2,5-Dimethyl-2H-pyrazol-3-ylmethyl)-2-[3-(pyrrol-1-yliminomethyl)-1-(2-trimethylsilanyl-ethoxymethyl)-1H-indazol-6-ylamino]-benzamide was used instead of N-methyl-N-{3-styryl-1-[2-trimethyl-silanyl)-ethoxymethyl]-1H-indazol-6-yl}-benzene-1,3-diamine. $^1$H NMR (DMSO-d$_6$) δ 13.27 (1H, s), 9.72 (1H, s), 9.05 (1H, t, J=5.3 Hz), 8.97 (1H, s), 8.16 (1H, d, J=8.7 Hz), 7.68 (1H, dd, J=8.3, 1.9 Hz), 7.50 (2H, t, J=2.6 Hz), 7.46–7.38 (2H, m), 7.25 (1H, s), 7.05 (1H, dd, J=8.7, 1.9 Hz), 6.91 (1H, t, J=6.80 Hz), 6.20 (2H, t, J=2.3 Hz), 5.91 (1H, s), 4.43 (2H, d, J=5.6 Hz), 3.71 (3H, s), 2.04 (3H, s).

Example 62

2-[3-(Pyrrol-1-yliminomethyl)-1H-indazol-6-ylamino]-benzoic acid

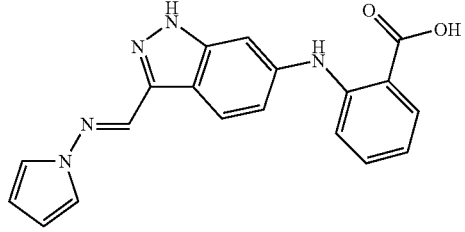

Prepared in a similar manner to that described for Example 11 in U.S. Pat. No. 6,534,524, issued Mar. 18, 2003, herein incorporated by reference in its entirety for all purposes, except using 2-[3-(Pyrrol-1-yliminomethyl)-1-(2-trimethylsilanyl-ethoxymethyl)-1H-indazol-6-ylamino]-benzoic acid instead of N-methyl-N-{3-styryl-1-[2-trimethyl-silanyl)-ethoxymethyl]-1H-indazol-6-yl}-benzene-1,3-diamine. $^1$H NMR (DMSO-d$_6$) δ 13.12 (1H, s), 12.70 (1H, s), 8.94 (1H, s), 8.10 (1H, d, J=8.7 Hz), 7.91 (1H, dd, J=1.7, 7.7 Hz), 7.50 (2H, t, J=2.3 Hz), 7.36 (1H, d, J=7.9 Hz), 7.27 (1H, d, J=1.5 Hz), 7.16 (1H, t, J=7.5 Hz), 6.94 (1H, dd, J=1.7, 8.7 Hz), 6.68 (1H, t, J=7.5 Hz), 6.19(2H, t, J=2.3 Hz).

Example 63

N-Prop-2-ynyl-2-[3-(pyrrol-1-yliminomethyl)-1H-indazol-6-ylamino]-benzamide

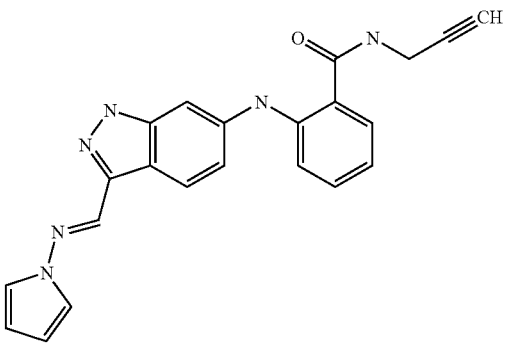

Prepared in a similar manner to that described for Example 6 above, except using 2-[3-(Pyrrol-1-yliminomethyl)-1H-indazol-6-ylamino]-benzoic acid and propargylamine. $^1$H NMR (DMSO-d$_6$) δ 13.30 (1H, s), 9.82 (1H, s), 9.04 (1H, t, J=5.6 Hz), 8.98 (1H, s), 8.19 (1H, d, J=8.6 Hz), 7.69 (1H, d, J=7.9 Hz), 7.45(4H, m), 7.31 (1H, s), 7.08 (1H, d, J=8.6 Hz), 6.91 (1H, t, J=7.6 Hz), 6.21 (2H, s), 4.05 (2H, s), 3.13 (1H, s). Anal. Calcd for C$_{22}$H$_{18}$N$_6$O. 0.40H$_2$O. 0.05 Hexanes: C, 67.97; H, 5.01; N, 21.33. Found: C, 67.91; H, 4.78; N, 21.00.

Example 64

N-(4-Hydroxy-but-2-ynyl)-2-[3-(2-pyridin-2-yl-vinyl)-1H-indazol-6-ylamino]-benzamide

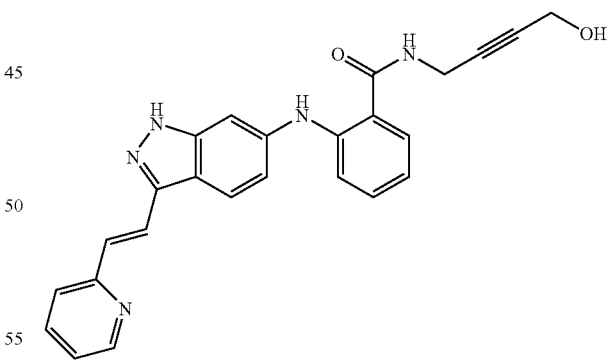

Prepared in a similar manner to that described for Example 6 above, except using tetrabutyl ammonimum 2-[3-(2-Pyridin-2-yl-vinyl)-1H-indazol-6-ylamino]-benzoate and 4-Amino-but-2-yn-1-ol. $^1$H NMR (DMSO-d$_6$): δ 12.95 (1H, s), 9.84 (1H, s), 9.02 (1H, t, J=5.6 Hz), 8.59 (1H, d, J=4.9 Hz), 8.08 (1H, d, J=8.7 Hz), 7.90 (1H, d, J=16.2 Hz), 7.80 (1H, t, J=7.2 Hz), 7.70–7.64 (2H, m), 7.51 (1H, d, J=16.2 Hz), 7.45–7.36 (2H, m), 7.27–7.24 (2H, m), 7.02 (1H, d, J=9.0 Hz), 6.88 (1H, t, J=7.2 Hz), 5.13 (1H, t, J=5.6 Hz), 4.10–4.04 (4H, m).

Example 65

N-(2,5-Dimethyl-2H-pyrazol-3-ylmethyl)-2-[3-(2-pyridin-2-yl-vinyl)-1H-indazol-6-ylamino]-benzamide

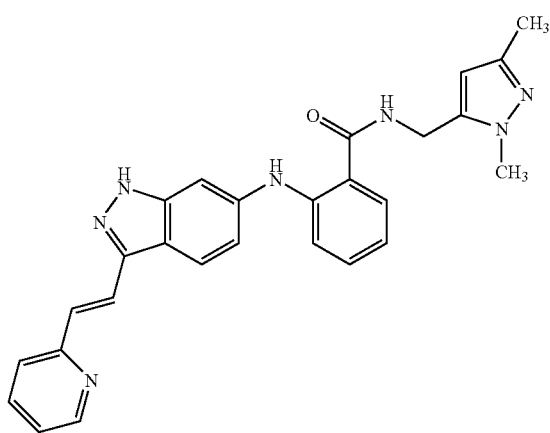

Prepared in a similar manner to that described for Example 6 above, except using tetrabutyl ammonimum 2-[3-(2-Pyridin-2-yl-vinyl)-1H-indazol-6-ylamino]-benzoate and C-(2,5-Dimethyl-2H-pyrazol-3-yl)-methylamine. $^1$H NMR (DMSO-$d_6$) δ 12.93 (1H, s), 9.70 (1H, s), 9.04 (1H,bt), 8.58 (1H, d, J=4.0 Hz), 8.07 (1H, d, J=8.8 Hz), 7.88 (1H, d, J=16.4 Hz), 7.79 (1H, t, J=8.6 Hz), 7.71–7.64 (2H, m), 7.50 (1H, d, J=16.4 Hz), 7.44–7.39 (2H, m), 7.28–7.23 (2H, m), 7.00 (1H, d, J=8.8 Hz), 6.90 (1H, t, J=8.0 Hz), 5.91 (1H, s), 4.43 (2H, d, J=5.5 Hz), 3.71 (3H, s), 2.04 (3H, s).

The exemplary compounds described above may be tested for their activity using the tests described below.

BIOLOGICAL TESTING: ENZYME ASSAYS

The stimulation of cell proliferation by growth factors such as VEFG, FGF, and others is dependent upon their induction of autophosphorylation of each of their respective receptor's tyrosine kinases. Therefore, the ability of a protein kinase inhibitor to block autophosphorylation can be measured by inhibition of the peptide substrates. To measure the protein kinase inhibition activity of the compounds, the following constructs were devised.

VEGF-R2 Construct for Assay

This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E99OV) within the kinase insert domain relative to wild-type VEGF-R2. Autophosphorylation of the purified construct was performed by incubation of the enzyme at a concentration of 4 μM in the presence of 3 mM ATP and 40 mM MgCl$_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., Biochemistry, 37,16788–16801 (1998).

FGF-R1 Construct for Assay

The intracellular kinase domain of human FGF-R1 was expressed using the baculovirus vector expression system starting from the endogenous methionine residue 456 to glutamate 766, according to the residue numbering system of Mohammadi et al., Mol. Cell. Biol., 16, 977–989 (1996). In addition, the construct also has the following 3 amino acid substitutions: L457V, C488A, and C584S.

LCK Construct for Assay

The LCK tyrosine kinase was expressed in insect cells as an N-terminal deletion starting from amino acid residue 223 to the end of the protein at residue 509, with the following two amino acid substitutions at the N-terminus: P233M and C224D.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 (indicated as FLVK-P in the tables below) were the following: 1 mM PEP; 250 μM NADH; 50 units of LDH/mL; 20 units of PK/mL; 5 mM DTT; 5.1 mM poly($E_4Y_1$); 1 mM ATP; and 25 mM MgCl$_2$ in 200 mM HEPES, pH 7.5. Assay conditions for unphosphorylated VEGF-R2Δ50 (indicated as FLVK in the tables) were the following: 1 mM PEP; 250 μM NADH; 50 units of LDH/mL; 20 units of PK/mL; 5 mM DTT; 20 mM poly($E_4Y_1$); 3 mM ATP; and 60 mM MgCl$_2$ and 2 mM MnCl$_2$ in 200 mM HEPES, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azino-di-[3-ethylbenzathiazoline sulfonate(6)] diammonium salt (ABTS). Typical assay solutions contained: 2 μM biotinylated gastrin peptide; 5 mM DTT; 20 μM ATP; 26 mM MgCl$_2$; and 2 mM MnCl$_2$ in 200 mM HEPES, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid (H$_2$SO$_4$), followed by absorbance reading at 405 nm. $K_i$ values were determined by measuring enzyme activity in the presence of varying concentrations of test compounds. The data were analyzed using Enzyme Kinetic and Kaleidagraph software.

Fibroblast Growth Factor (FGF-R) Assay

The spectrophotometric assay was carried out as described above for VEGF-R2, except for the following changes in concentration: FGF-R=50 nM, ATP=2 mM, and poly(E4Y1)=15 mM.

Lymphocyte-Specific Protein-Tyrosine Kinase (LCK) Assay

The spectrophotometric assay was carried out as described above for VEGF-R2, except for the following changes in concentration: LCK=60 nM, $MgCl_2$=0 mM, poly(E4Y1)=20 mM.

Focal Adhesion Kinase (FAK) Assay

FAK High Throughput Screening (HTS) utilizes the fluorescence polarization assay provided by LJL Biosystems. The kinase reaction contained: 100 mM Hepes pH 7.5, 10 mM $MgCl_2$, 1 mM DTT, 1 mM ATP, and 1 mg/ml poly Glu-Tyr (4:1). The reaction is initiated by the addition of 5 nM FAKcd409. The reaction is terminated by the addition of EDTA followed by addition of fluor-labelled peptide and anti-phosphotyrosine antibody, both provided by LJL Biosystems. Inhibition results are read on a Analyst (LJL) detector.

TIE-2 Spectrophotometric Assay

The kinase-catalyzed production of ADP from ATP that accompanies phosphoryl transfer to the random copolymer poly($Glu_4Tyr$) was coupled to the oxidation of NADH through the activities of pyruvate kinase (PK) and lactate dehydrogenase (LDH). NADH conversion to $NAD^+$ was monitored by the decrease in absorbance at 340 nm ($\epsilon$=6.22 $cm^{-1}$ $mM^{-1}$) using a Beckman DU650 spectrophotometer. Typical reaction solutions contained 1 mM phosphoenolpyruvate, 0.24 mM NADH, 40 mM $MgCl_2$, 5 mM DTT, 2.9 mg/mL poly($Glu_4Tyr$), 0.5 mM ATP, 15 units/mL PK, 15 units/mL LDH in 100 mM HEPES, pH 7.5. Assays were initiated with the addition of 4 to 12 nM phosphorylated Tie-2 (aa 775–1122). Percent inhibition was determined in triplicate at a 1 μM level of inhibitor.

TIE-2 DELFIA Assay

Formation of phosphotyrosine was monitored using biotinylated p34cdc2 (aa6–20=KVEKIGEGTYGVVYK) peptide as substrate. Biotinylated peptide was immobilized using NeutrAvidin™ coated 96-well microtiter plates followed by detection using anti-phosphotyrosine-antibody (PY20) conjugated to europium N1 chelate. Typical assay solutions contained: 1 gM biotinylated p34cdc2 peptide, 150 μM ATP, 5 mM $MgCl_2$, 1 mM DTT, 0.01% BSA, 5% glycerol, 2% DMSO, 25 mM HEPES pH 7.5. The assay was initiated in the NeutrAvidin plate with 50 nM of TIE2 intracellular domain. The kinase reaction was terminated with 50 mM EDTA. Plates were then washed, and europium antibody added. After incubation, they were again washed, and DELFIA™ Enhancement Solution added. Plates were read at standard Europium time-resolved settings (ex 340 nm, em 615 nm, delay 400 μsec, window 400 μsec). Percent inhibition was calculated with reference to intraplate wells which had added DMSO rather than compound in DMSO, with background subtracted from both experimental and control with reference to an intraplate well which had EDTA added prior to addition of enzyme.

HUVEC Proliferation Assay

This assay determines the ability of a test compound to inhibit the growth factor-stimulated proliferation of human umbilical vein endothelial cells ("HUVEC"). HUVEC cells (passage 3–4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 μg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 μl of rich, culture medium (described above). The cells were allowed to attach for 24 hours in this medium. The medium was then removed by aspiration and 105 μl of starvation media (F12K+1% FBS) was added to each well. After 24 hours, 15 μl of test agent dissolved in 1% DMSO in starvation medium or this vehicle alone was added into each treatment well; the final DMSO concentration was 0.1%. One hour later, 30 μl of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595λ was determined on a 96-well spectrophotometer plate reader.

$IC_{50}$ values were calculated by curve-fitting the response of $A^{595}$ to various concentrations of the test agent; typically, seven concentrations separated by 0.5 log were employed, with triplicate wells at each concentration. For screening compound library plates, one or two concentrations (one well per concentration) were employed, and the % inhibition was calculated by the following formula:

% inhibition=(control−test)÷(control−starvation)

where
control=$A^{595}$ when VEGF is present without test agent
test=$A^{595}$ when VEGF is present with test agent
starvation=$A^{595}$ when VEGF and test agent are both absent.

Mouse PK Assay

The pharmacokinetics (e.g., absorption and elimination) of drugs in mice were analyzed using the following experiment. Test compounds were formulated as a solution or suspension in a 30:70 (PEG 400: acidified $H_2O$) vehicle or as a suspension in 0.5% CMC. This was administered orally (p.o.) and intraperitoneally (i.p.) at variable doses to two distinct groups (n=4) of B6 female mice. Blood samples were collected via an orbital bleed at time points: 0 hour (pre-dose), 0.5 h, 1.0 h, 2.0 h, and 4.0 h, and 7.0 h post dose. Plasma was obtained from each sample by centrifugation at 2500 rpm for 5 min. Test compound was extracted from the plasma by an organic protein precipitation method. For each time bleed 50 μL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of $N_2$ gas. To each tube containing the dried test compound extract 125 μL of mobile phase (60:40, 0.025 M $NH_4H_2PO_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection. From each sample, 95 μL was injected onto a Phenomenex-Prodigy reverse phase C-18, 150×3.2 mm column and eluted with a 45–50% acetonitrile gradient run over 10 min. Test-compound plasma concentrations (μg/mL) were determined by a comparison to standard curve (peak area vs. conc. μg/mL) using known concentrations of test compound extracted from plasma samples in the manner described above. Along with the standards and unknowns, three groups (n=4) of quality controls (0.25

μg/mL, 1.5 μg/mL, and 7.5 μg/mL) were run to insure the consistency of the analysis. The standard curve had an R2>0.99 and the quality controls were all within 10% of their expected values. The quantitated test samples were plotted for visual display using Kalidagraph software and their pharmacokinetic parameters were determined using WIN NONLIN software. Example 1(a) provided the following results: 0.69 (Mouse pK, AUC, ip, μg-h/ml); 0.33 (Mouse pK, AUC, po, μg-h/ml).

KDR (VEGFR2) Phosphorylation in PAE-KDR Cells Assay

This assay determines the ability of a test compound to inhibit the autophosphorylation of KDR in porcine aorta endothelial (PAE)-KDR cells. PAE cells that overexpress human KDR were used in this assay. The cells were cultured in Ham's F12 media supplemented with 10% fetal bovine serum (FBS) and 400 μg/mL G418. Thirty thousands cells were seeded into each well of a 96-well plate in 75 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37 μC for 1 hour and the cells were then stimulated with 500 ng/ml VEGF (commercially available from R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (commercially available from Pierce) which was pre-coated with Rabbit anti Human Anti-flk-1 C-20 antibody (commercially available from Santa Cruz). The plates were incubated at room temperature for 2 hours and washed seven times with 1% Tween 20 in PBS. HRP-PY20 (commercially available from Santa Cruz) was diluted and added to the plate for a 30-minute incubation. Plates were then washed again and TMB peroxidase substrate (commercially available from Kirkegaard & Perry) was added for a 10-minute incubation. One hundred μL of 0.09 N $H_2SO_4$ was added to each well of the 96-well plates to stop the reaction. Phosphorylation status was assessed by spectrophotometer reading at 450 nm. $IC_{50}$ values were calculated by curve fitting using a four-parameter analysis.

PAE-PDGFRβ Phosphorylation in PAE-PDGFRB Cells Assay

This assay determines the ability of a test compound to inhibit the autophosphorylation of PDGFRβ in porcine aorta endothelial (PAE)-PDGFRβ cells. PAE cells that overexpress human PDGFRβ were used in this assay. The cells were cultured in Ham's F12 media supplemented with 10% fetal bovine serum (FBS) and 400 ug/ml G418. Twenty thousands cells were seeded in each well of a 96-well plate in 50 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37° C. for 1 hour and the cells were then stimulated with 1 μg/mL PDGF-BB (R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (Pierce), which was pre-coated with Rabbit anti Human PDGFRβ antibody (Santa Cruz). The plates were incubated at room temperature for 2 hours and washed seven times with 1% Tween 20 in PBS. HRP-PY20 (Santa Cruz) was diluted and added to the plate for a 30-minute incubation. Plates were then washed again and TMB peroxidase substrate (Kirkegaard & Perry) was added for a 10-minute incubation. One hundred μL of 0.09 N $H_2SO_4$ was added into each well of the 96-well plate to stop the reaction. Phosphorylation status was assessed by spectrophotometer reading at 450 nm. $IC_{50}$ values were calculated by curve fitting using a four-parameter analysis.

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate (KPO4) buffer. Appropriate amounts of KPO4 buffer, NADPH-regenerating solution (containing B-NADP, glucose-6-phosphate, glucose-6-phosphate dehydrogenase, and $MgCl_2$), and HLM were preincubated in 13×100 mm glass tubes at 37 C. for 10 min. (3 tubes per test compound—triplicate). Test compound (5 □M final) was added to each tube to initiate reaction and was mixed by gentle vortexing, followed by incubation at 37° C. At t=0, 2 h, a 250 μL sample was removed from each incubation tube to separate 12×75 mm glass tubes containing 1 mL ice-cold acetonitrile with 0.05 μM reserpine. Samples were centrifuged at 4000 rpm for 20 min. to precipitate proteins and salt (Beckman Allegra 6KR, S/N ALK98DO6, #634). Supernatant was transferred to new 12×75 mm glass tubes and evaporated by Speed-Vac centrifugal vacuum evaporator. Samples were reconstituted in 200 μL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1–3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP 1100 diode array HPLC and a Micromass Quattro II triple quadruple mass spectrometer operating in positive electrospray SIR mode (programmed to scan specifically for the molecular ion of each test compound. Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

The results of the testing of the compounds using various assays are summarized in the table below, where a notation of "% @" indicates the percent inhibition at the stated concentration, "*" values represent Ki (nM) or % inhibition at a compound concentration of 1 μM for * or 50 nM for **, unless otherwise indicated. "NT" indicates no significant inhibition or not tested.

TABLE 1

| Example # | FLVK Ki % inh @ 50 nM | FLVK-P** | LckP* % inhibit @1 μM | FGF-P % inhibit @1 μM | HUVEC IC50 (nM) | HUVEC + albumin IC50 (nM) | % remaining (HLM) | PAE PDGFR autophos IC50 (nM) | PAE KDR IC50 nM AVG | bFGF Huvec IC50 (nM) AVG |
|---|---|---|---|---|---|---|---|---|---|---|
| 3(a) | 98 | NT | 30 | 99 | 12.7 | NT | NT | NT | NT | NT |
| 3(b) | 98 | NT | 27 | 96 | 5.7 | NT | 84@2 h | NT | NT | NT |
| 3(c) | 91 | NT | 9 | 83 | 0.43 | 9.2 | 46@0.5 h | NT | NT | NT |
| 3(d) | 89 | NT | 11 | 80 | 0.4 | 7.5 | 68@2 h | 3.5 | NT | 147 |
| 3(f) | 95 | NT | 41 | 60 | NT | >100 | NT | NT | NT | NT |
| 3(g) | 95 | NT | 28 | 72 | 1.1 | NT | 72@0.5 h | NT | NT | NT |
| 3(h) | 96 | NT | 37 | 85 | 1.6 | NT | 75@0.5 h | 0.63 | NT | NT |
| 3(i) | 88 | NT | 22 | 45 | 0.2 | NT | NT | 1.9 | NT | 1000 |
| 3(j) | 80 | NT | 17 | 43 | 1.7 | NT | 65@0.5 h | 4.7 | NT | NT |
| 3(k) | 74 | NT | 19 | 36 | 0.8 | NT | 75@0.5 h | 5 | NT | 1000 |
| 3(q) | 47 | NT | 7 | 31 | 5 | NT | 82@0.5 h | 5.2 | NT | NT |
| 2(h) | 84 | NT | NT | 75 | 1.6 | NT | 74@0.5 h | 2.8 | NT | 70 |
| 1(k) | 27 | NT | NT | 12 | >10 | NT | NT | NT | NT | NT |
| 2(g) | 83 | NT | NT | 79 | 0.71 | NT | 85@0.5 h | 10.5 | NT | 173 |
| 64 | 94 | NT | NT | 39 | 0.15 | NT | 66@0.5 h | 5.5 | NT | 1250 |
| 65 | 3.11 nM | NT | NT | NT | 3.4 | NT | 86@0.5 h | 5.8 | NT | NT |
| 61 | 65 | NT | NT | 14 | 6.5 | NT | NT | NT | NT | 662 |
| 41 | 45 | NT | NT | 11 | 6.4 | NT | NT | NT | NT | 3775 |
| 51 | 82 | NT | NT | 52 | NT | NT | NT | NT | NT | NT |
| 15 | 64 | NT | NT | 29 | 1.5 | NT | NT | 12.3 | NT | 1613 |
| 36 | 95 | 0.3 nM | NT | 69 | 1.67 | NT | NT | NT | 1.62 | 935 |
| 13 | 80 | NT | NT | 63 | NT | NT | NT | 6 | NT | NT |
| 18 | 94 | NT | NT | 59% | NT | NT | NT | NT | NT | 1882 |
| 20 | 91 | NT | NT | 35% | 0.084 | NT | NT | NT | NT | NT |
| 37 | 90 | NT | NT | 45 | NT | NT | NT | NT | 0.76 | NT |
| 38 | 75 | NT | NT | NT | NT | 0.68 | NT | 2 | NT | NT |
| 39 | 96 | NT | NT | 76% | NT | NT | NT | 4.7 | NT | NT |
| 32 | 78 | NT | NT | 70% | 0.61 | NT | 97@0.5 h | 0.5 | NT | NT |
| 55 | 97 | NT | NT | 67% | 0.2 | NT | NT | 3.7 | NT | NT |
| 57 | 91 | NT | NT | 52% | <1.8 | NT | NT | 1.3 | NT | NT |
| 63 | 85 | NT | NT | 63% | 0.1 | NT | NT | 2.4 | NT | NT |
| 34 | 72 | NT | NT | NT | NT | NT | NT | 4.5 | NT | NT |
| 10 | 76 | 6.07 | NT | 38, 197 nM | 0.67 | NT | 80@0.5 h | 21 | NT | NT |
| 45 | 28 | NT | NT | 24 | NT | NT | NT | NT | NT | NT |
| 49 | 11 | NT | NT | 36 | NT | NT | NT | NT | NT | NT |
| 23 | 23 | NT | NT | 56 | NT | NT | NT | 40 | NT | NT |
| 25 | 64 | NT | NT | 13 | 3 | NT | NT | NT | NT | NT |

In Vivo Assay of Retinal Vascular Development in Neonatal Rats

The development of the retinal vascular in rats occurs from postnatal day 1 to postnatal day 14 (P1–P14). This process is dependent on the activity of VEGF (J. Stone, et al, *J. Neurosci.*, 15, 4738 (1995)). Previous work has demonstrated that VEGF also acts as a survival factor for the vessels of the retina during early vascular development (Alon, et. al, *Nat. Med.*, 1, 1024 (1995)). To assess the ability of specific compounds to inhibit the activity of VEGF in vivo, compounds were formulated in an appropriate vehicle, usually 50% polyethylene glycol, average molecular weight 400 daltons, and 50% solution of 300 mM sucrose in deionized water. Typically, two microliters (2 μl) of the drug solution was injected into the midvitreous of the eye of rat pups on postnatal day 8 or 9. Six days after the intravitreal injection, the animals were sacrificed and the retinas dissected free from the remaining ocular tissue. The isolated retinas were then subjected to a histochemical staining protocol that stains endothelial cells specifically (Lutty and McLeod, *Arch. Ophthalmol.*, 110, 267 (1992)), revealing the extent of vascularization within the tissue sample. The individual retinas are then flat-mount onto glass slides and examined to determine the extent of vascularization. Effective compounds inhibit the further development of the retinal vasculature and induce a regression of all but the largest vessels within the retina. The amount of vessel regression was used to assess the relative potency of the compounds after in vivo administration. Vessel regression is graded on subjective scale of one to three pluses, with one plus being detectable regression judged to be approximately 25 percent or less, two pluses being judged to be approximately 25–75% regression and three pluses give to retinas with near total regression (approximately 75% or greater).

For more quantitative analysis of regression, images of ADPase-stained, flat-mounted retinas were captured with a digital camera attached to a dissecting microscope. Retinal images were then imported into an image analysis software (Image Pro Plus 4.0, Media Cybernetics, Silver Spring, Md.). The software was employed to determine the percentage of the area of the retina that contained stained vessels. This value for the experimental eye was compared to that measured for the vehicle injected, contralateral eye from the same animal. The reduction in the vascular area seen in the eye that received compound as compared to the vehicle-injected eye was then expressed as the "percent regression" for that sample. Percent regression values were averaged for groups of 5–8 animals.

In samples in which observation through the microscope indicated near total regression, a percent regression value of 65–70% was routinely measured. This was due to stain deposits within folds of retina, folds that were induced by the vehicle used for drug injection. The image analysis software interpreted these stain-containing folds as vessels. No attempt was made to correct for these folds since they varied from eye to eye. Thus, it should be noted that the percent regression values reported result from a conservative measurement that accurately rank orders compounds, but underestimates their absolute potency.

In Vivo Assay of Retinal Vascular Development in Neonatal Rat Model of Retinopathy of Prematurity A second model of VEGF dependent retinal neovascularization was employed to evaluate the activities of this series of compounds. In this model (Penn et. al, *Invest. Ophthalmol. Vis. Sci.*, 36, 2063, (1995)), rats pups (n=16) with their mother are placed in a computer controlled chamber that regulates the concentration of oxygen. The animals are exposed for 24 hours to a concentration of 50% oxygen followed by 24 hours at a concentration of 10% oxygen. This alternating cycle of hyperoxia followed by hypoxia is repeated 7 times after which the animals are removed to room air (P14). Compounds are administered via intravitreal injection upon removal to room air and the animals are sacrificed 6 days later (P20). The isolated retinas are then isolated, stained mounted and analyzed as detail above in the development model. The effectiveness was also graded as is described for the development model.

The exemplary compounds described above may be formulated into pharmaceutical compositions according to the following general examples.

EXAMPLE A

Parenteral Composition

To prepare a parenteral pharmaceutical composition suitable for administration by injection, 100 mg of a water-soluble salt of a compound of Formula I is dissolved in dimethylsulfoxide and then mixed with 10 mL of 0.9% sterile saline. The mixture is incorporated into a dosage unit form suitable for administration by injection.

EXAMPLE B

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

EXAMPLE C

Intraocular Composition

To prepare a sustained-release pharmaceutical composition for intraocular delivery, a compound of Formula I is suspended in a neutral, isotonic solution of hyaluronic acid (1.5% conc.) in phosphate buffer (pH 7.4) to form a 1% suspension.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound, pharmaceutically acceptable salt, or pharmaceutically acceptable solvate, selected from the group consisting of:

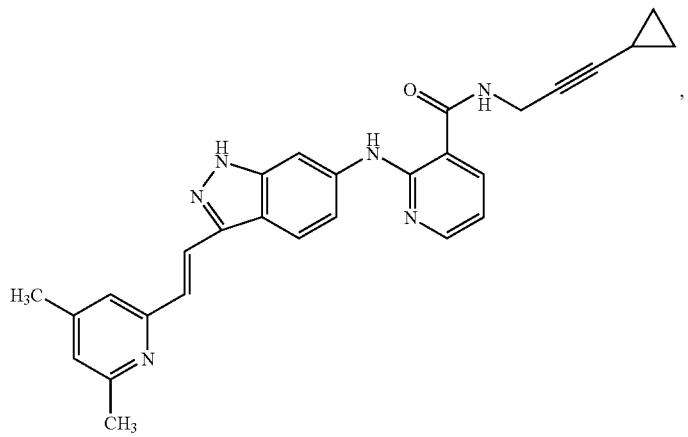

-continued
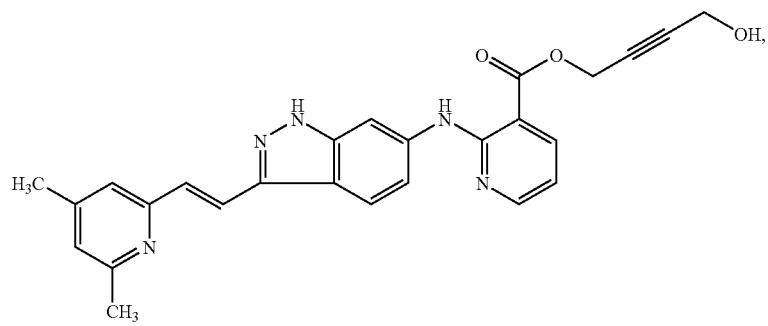
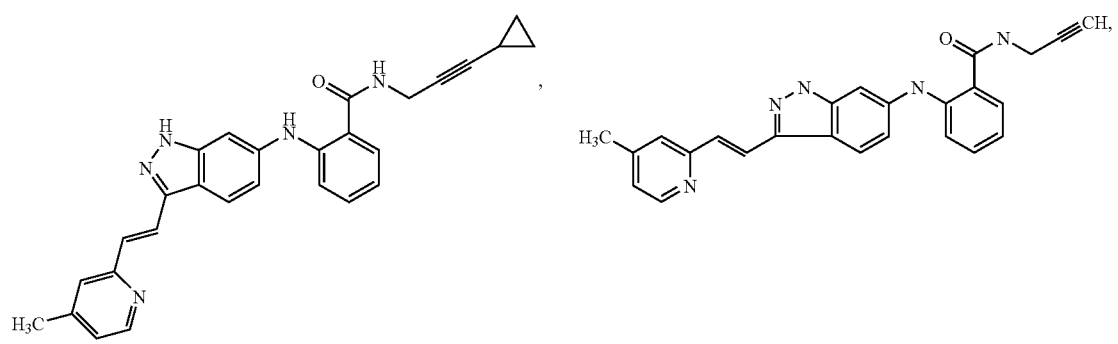
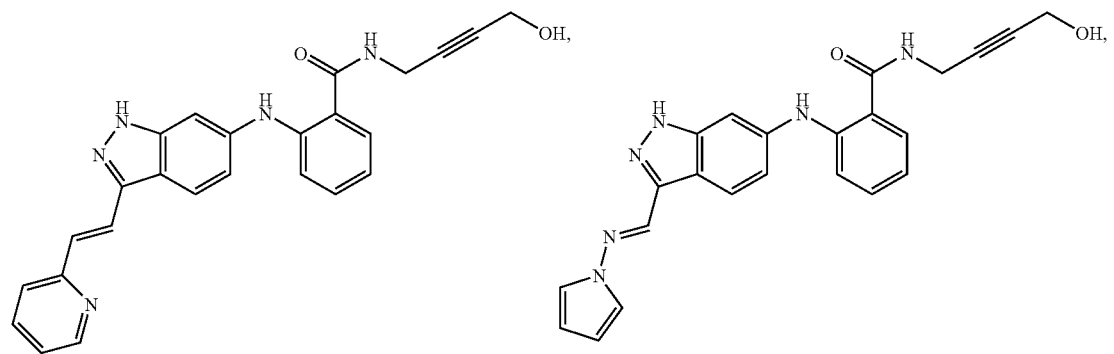
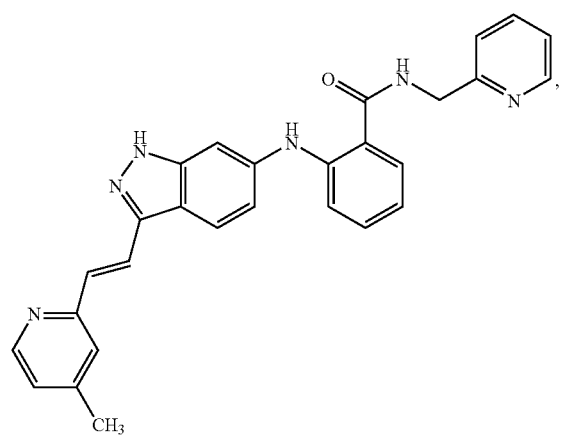

-continued
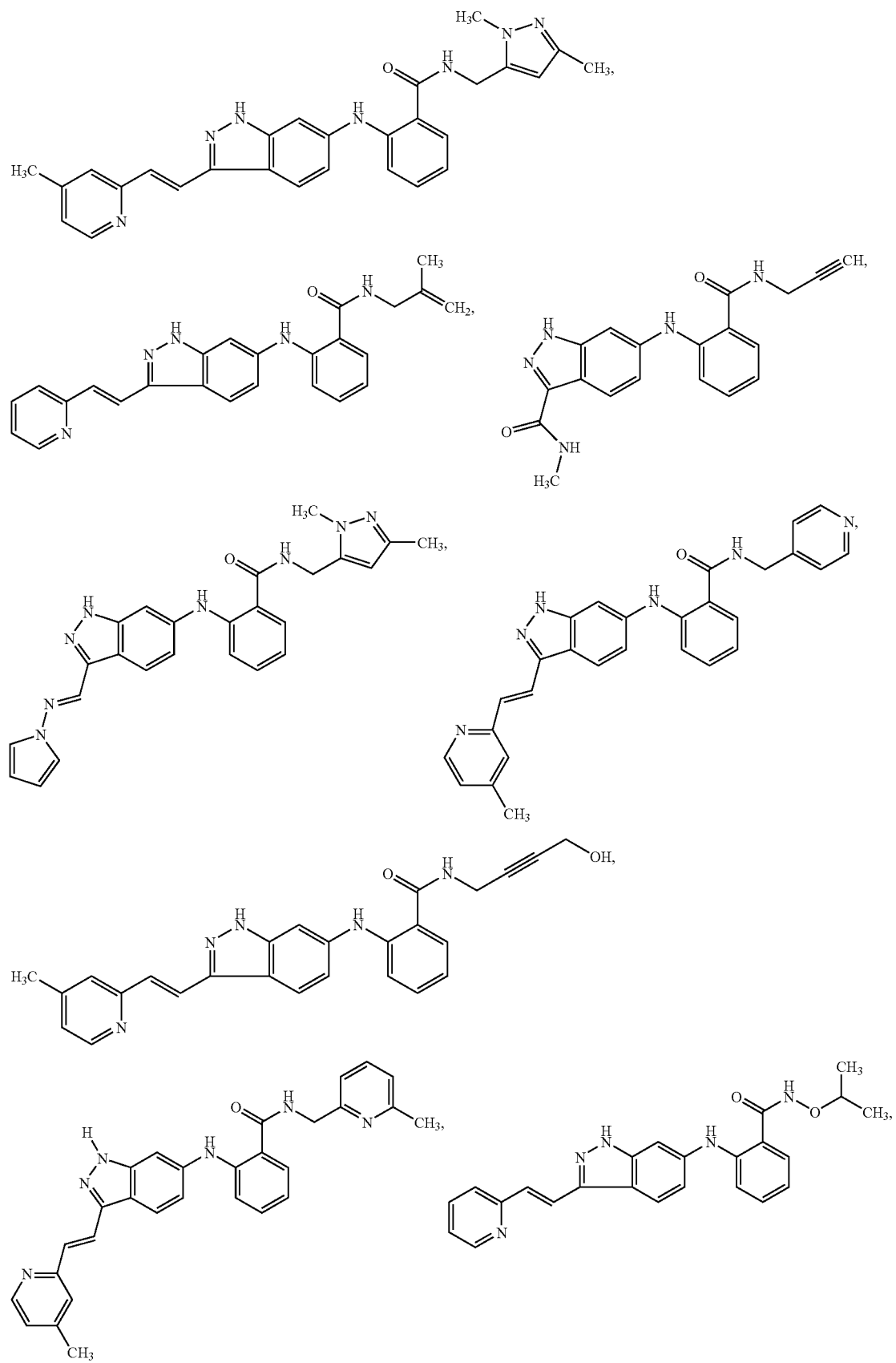

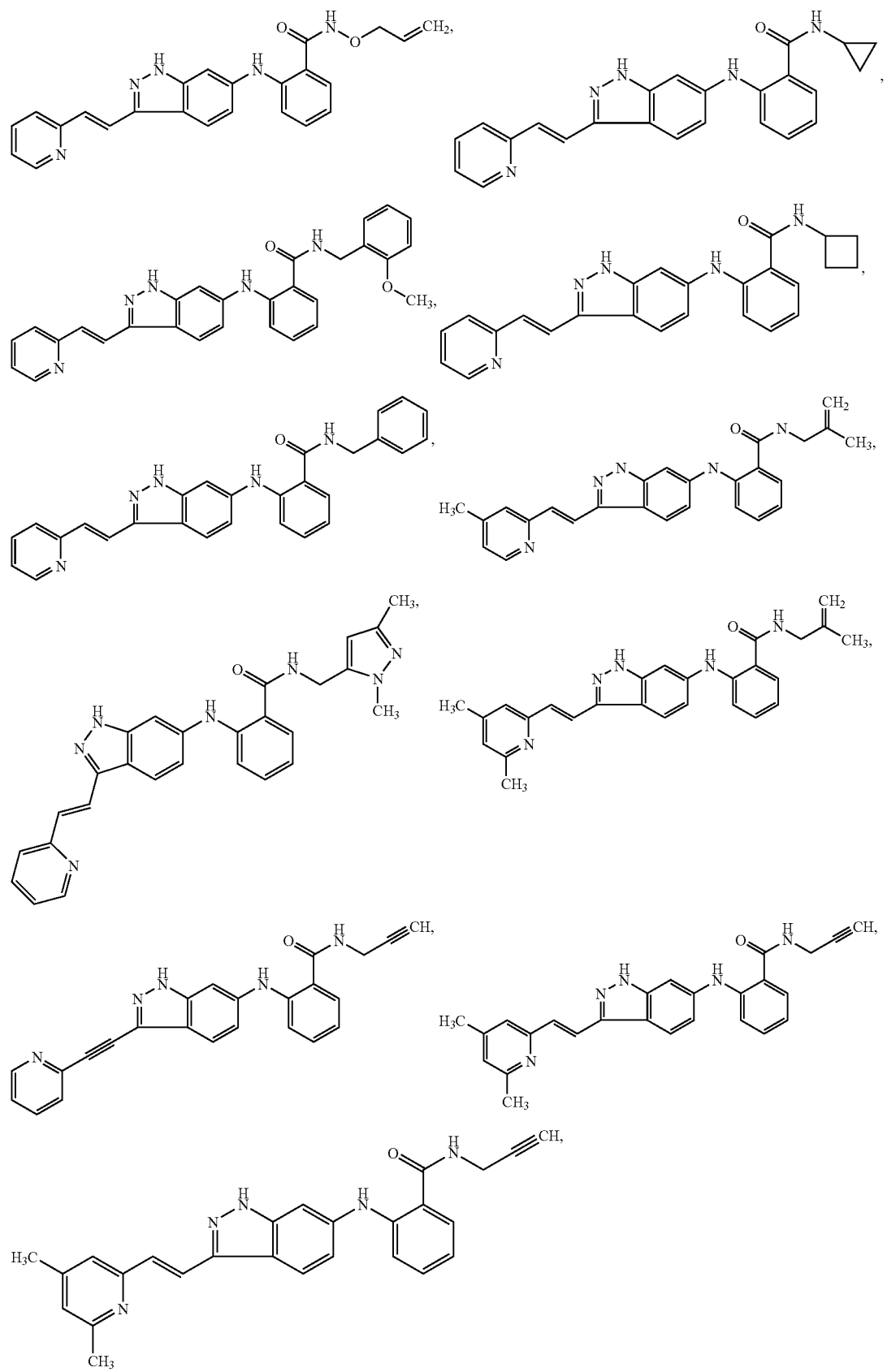

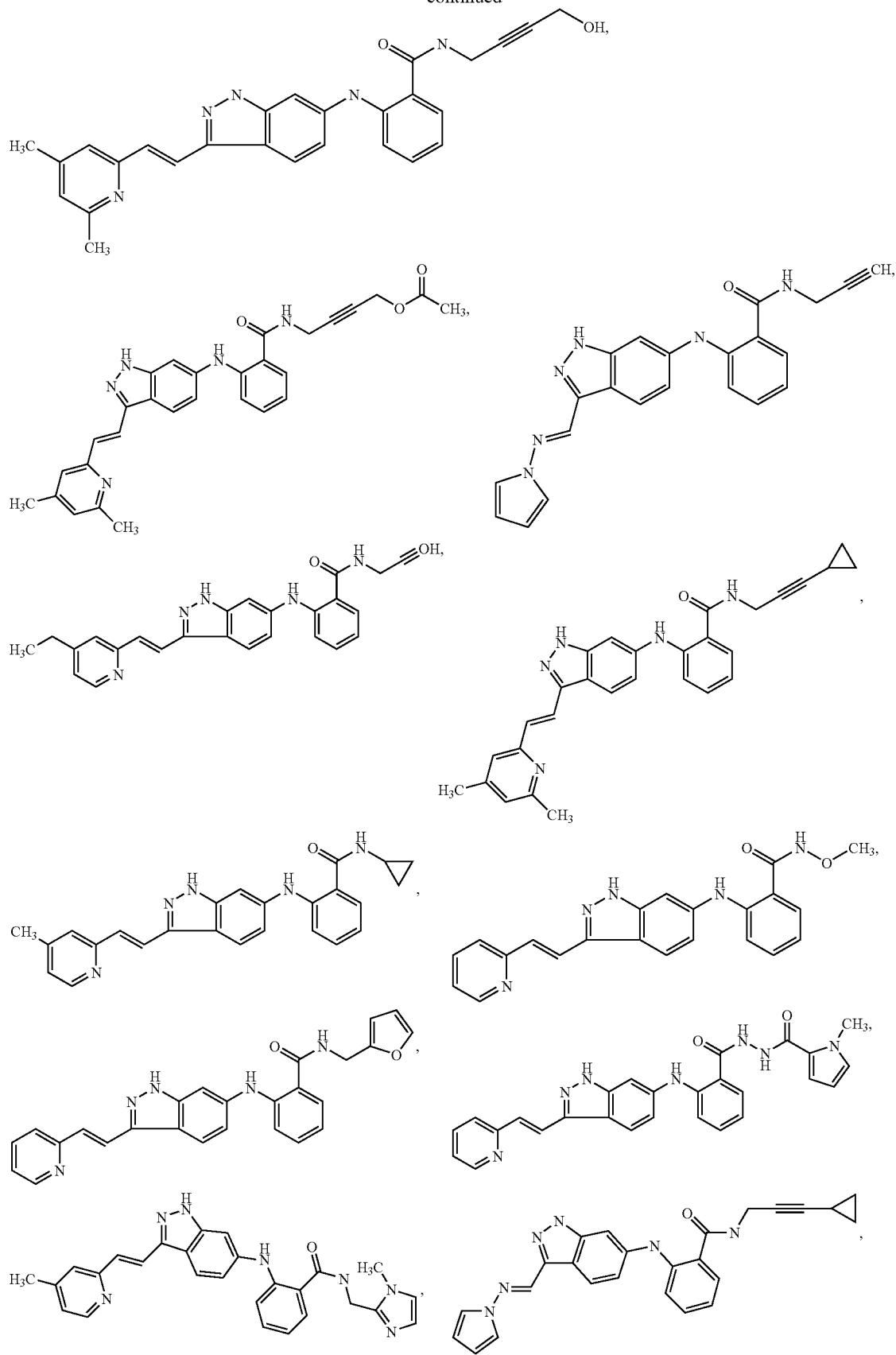

-continued

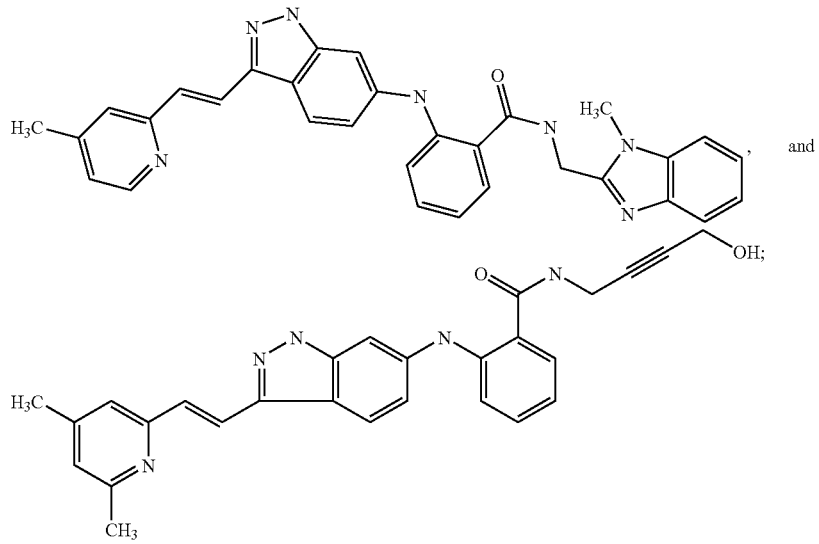

or a pharmaceutically acceptable salt or pharmaceutically acceptable solvate thereof.

2. A compound represented by the formula

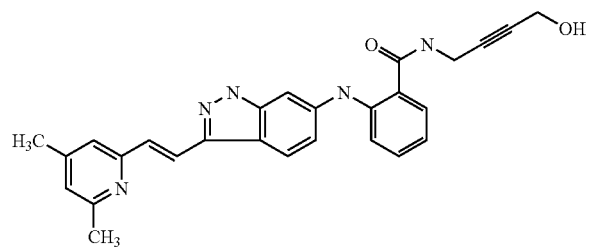

or a pharmaceutically acceptable salt or a pharmaceutically acceptable solvate thereof.

3. A pharmaceutical composition comprising:
  (a) a therapeutically effective amount of a compound, pharmaceutically acceptable solvate, or pharmaceutically acceptable salt of claim 1; and
  (b) a pharmaceutically acceptable carrier, diluent, or vehicle therefor.

4. A pharmaceutical composition comprising:
  (c) a therapeutically effective amount of a compound, pharmaceutically acceptable solvate, or pharmaceutically acceptable salt of claim 2; and
  (d) a pharmaceutically acceptable carrier, diluent, or vehicle therefor.

* * * * *